United States Patent
Pastan et al.

(10) Patent No.: US 7,470,775 B2
(45) Date of Patent: Dec. 30, 2008

(54) ANTI-CD30 STALK AND ANTI-CD30 ANTIBODIES SUITABLE FOR USE IN IMMUNOTOXINS

(75) Inventors: Ira H. Pastan, Potomac, MD (US); Satoshi Nagata, Rockville, MD (US); Masanori Onda, Rockville, MD (US); Yoshito Numata, Osaka (JP); Kenneth Santora, Kensington, MD (US); Richard Beers, Rockville, MD (US); Robert Kreitman, Potomac, MD (US); Abhishek Sinha, San Diego, CA (US)

(73) Assignee: The United States of America as represented by the Department of Health and Human Services, Washington, DC (US)

(*) Notice: Subject to any disclaimer, the term of this patent is extended or adjusted under 35 U.S.C. 154(b) by 466 days.

(21) Appl. No.: 10/516,766

(22) PCT Filed: Jun. 9, 2003

(86) PCT No.: PCT/US03/18373

§ 371 (c)(1),
(2), (4) Date: Dec. 3, 2004

(87) PCT Pub. No.: WO03/104432

PCT Pub. Date: Dec. 18, 2003

(65) Prior Publication Data

US 2006/0193771 A1    Aug. 31, 2006

Related U.S. Application Data

(60) Provisional application No. 60/387,293, filed on Jun. 7, 2002, provisional application No. 60/411,032, filed on Sep. 16, 2002.

(51) Int. Cl.
*C12P 21/08* (2006.01)
*C07K 16/00* (2006.01)
*A61K 39/395* (2006.01)
*G01N 33/574* (2006.01)
*C07H 21/04* (2006.01)
*C12P 21/04* (2006.01)

(52) U.S. Cl. ............... 530/388.22; 530/387.3; 530/388.8; 530/391.3; 530/391.7; 424/133.1; 424/135.1; 424/143.1; 424/155.1; 424/181.1; 424/183.1; 435/7.23; 435/69.6; 435/70.21; 435/320.1; 536/23.53

(58) Field of Classification Search .................. None
See application file for complete search history.

(56) References Cited

FOREIGN PATENT DOCUMENTS

WO    WO 9622384 A1 *  7/1996

OTHER PUBLICATIONS

Nagata et al. Clinical Cancer Research, 8(7):2345-2355, Jul. 2002.*
William E. Paul. Fundamental Immunology, 3rd Edition, pp. 292-295, 1993.*
Rudikoff et al. Proc. Natl. Acad. Sci. USA, 79:1979-1983, Mar. 1982.*
Colman P. M. Research in Immunology, 145:33-36, 1994.*
Bendig M. M. Methods: A Companion to Methods in Enzymology, 1995; 8:83-93.*

* cited by examiner

*Primary Examiner*—David J. Blanchard
(74) *Attorney, Agent, or Firm*—Townsend and Townsend and Crew LLP

(57) ABSTRACT

CD30 is a receptor expressed on cells of Hodgkin's disease and certain leukemias. The extracellular portion of CD30 is cleaved, releasing a form known as sCD30. The invention relates in part to the discovery that a residual, extracellular "stalk" of CD30 remains after cleavage of sCD30. The stalk provides an advantageous and previously unrecognized target for immunotoxins. The invention provides antibodies that bind to the CD30 stalk or to epitopes destroyed upon the cleavage of CD30 which results in the stalk. The invention further provides new anti-CD30 antibodies that form effective immunotoxins and are particularly suitable for making disulfide stabilized Fv ("dsFv")-immunoconjugates. The dsFv immunoconjugates can be used as reagents to label CD30-expressing cancer cells or to inhibit the growth of CD30-expressing cancer cells. Moreover, the invention provides anti-CD30 antibodies that activate complement-dependent cytotoxicity.

37 Claims, 9 Drawing Sheets

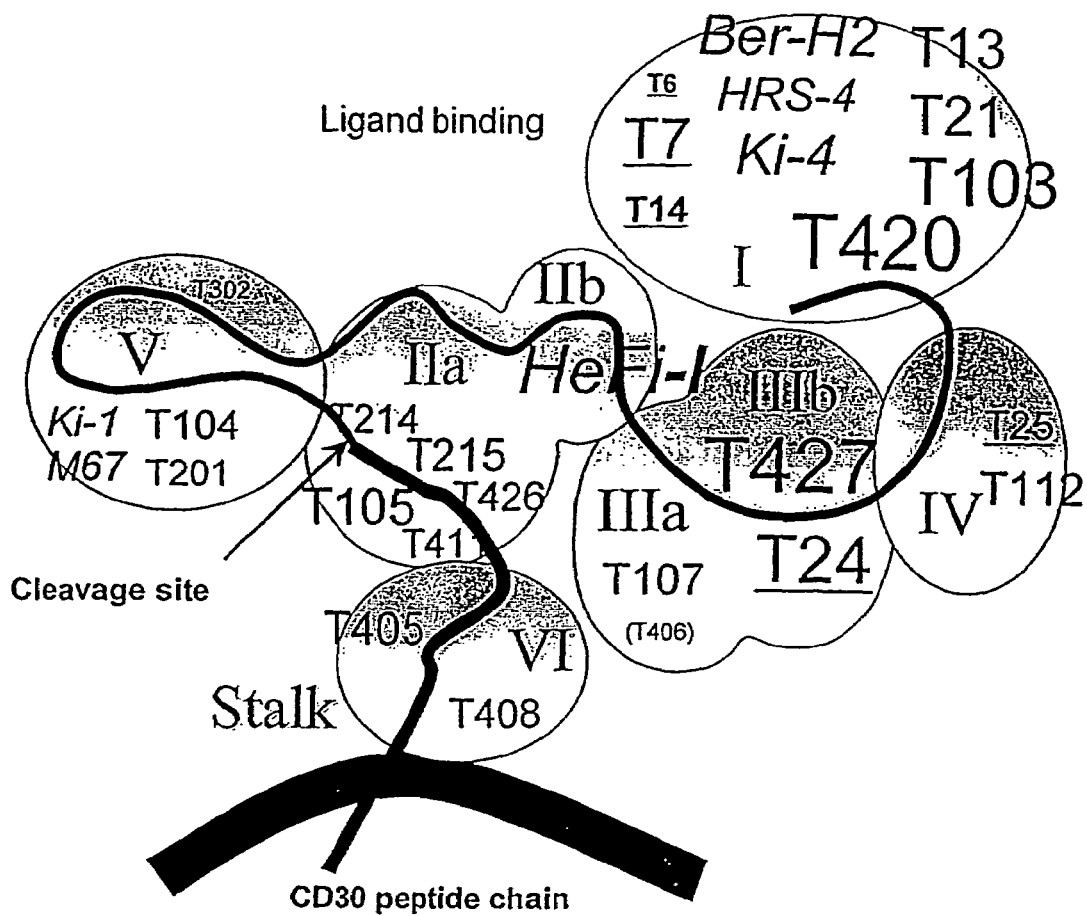
Fig.1. Location of topographical epitopes on CD30 molecule

Fig 2a. Amino acid sequences of the variable regions of anti-CD30 MAbs

| VH | SEQ ID NO: | FR1 | CDR1 | FR2 | CDR2 | FR3 | CDR3 | FR4 |
|---|---|---|---|---|---|---|---|---|
| T6 | 2 | QVQLKESGPGLVTPSQSLSITCTVSGFSLS | KYSIH | WVRQPPGRGLEWLG | MIW---GVENTDYNSALKS | RLSISKDNSKSQVFLKMNSLQSDDTAMYYCAR | KDLGLYGM-------NY | WGQGISVTVSA |
| T7 | 3 | QVQLQQSGAELVRPGSSVKISCKASGYTFS | SYWMN | WMKQRPGQGLEWIG | QIYP--GDDDTNYNGKFKG | KATLTADKSSSTAYMQLSSLTSEDSAVYFCAR | RETGRGAWF------TY | WGQGTLVTVSA |
| T13 | 4 | QVQLQQSGAELAKPGASVKMSCKASGYTFT | TYWMH | WVKQRPGQGLEWIG | YINP--STGYTDYNEKFKD | KATLTADKSSSTAYMQLSSLTSEDSAVYYCVR | RGSYDGNPF------AY | WGQGTLVSVSA |
| T14 | 5 | EVQLVESGGGLVKPKGGSLKLSCGVSGFTFS | DYYMY | WVRQTPEKRLEWVA | SISS--GGSYTYYSDSVKG | RLTISRDNTKNNLYLQMSSLKSEDTAVYYCVR | GPGGVL---------DY | WGQGTLTLTVSS |
| T24 | 6 | QVQLQQPGAELVRPGASVKLSCKASGYSFT | SYWID | WVKQRPGQGLEWIG | NIYP--SNAYTNYNQKFKD | KATLTVDKSSSTAYMQLSSPTSEDSAVYYCTS | VLDYFYAM-------DY | WGQGTSVTVSS |
| T25 | 7 | QVTLKESGPGILQPSQTLSLTCSFSGFSLN | TSGVGVG | WIRQPSGKGLEWLA | HIW---WDDDERYNPVLKS | RLTISKDTSSNQVFLKIANVDTADSATYYCVR | SMVAWF---------PY | WGRGTLVTVSA |
| HeFi-I | 8 | EVKLVESGGGLVQPGGSLRLSCATSGFTFS | DYYMN | WVRQPPGKALEWLG | FIRNKANGYTTEFSASVMG | RFTISRDDSQSILYLQMNTLRAEDSATYYCAR | DPPYGNPHYAM----DY | WGQGTLVTVSS |
| CL2 | 9 | EVQLKQSGTELVKPGASVKLSCKASGYTFT | SYWMH | WVKQRPGQGLEWIG | NINP--SNGGTNYNEKFKS | KATLTADKSSSTAYMQLSSLTSEDSAVYYCAR | RTETAQASPF-----AY | WGQGTLVTVSS |
| K1-4 | 10 | EVQLVQSGAELAKPGRAVKMSCKASGYTFT | DYWMH | WVKQRPGQDLEWIG | YINP--NTAYTDYNQKFKD | KATLTADKSSSTAYMQLSSLTSEDSAVYYCAK | KTTQTTWGF------PF | WGQGTLVTVSA |
| T420 | 11 | QVQLQQSGAELAKPGASVKMSCKASGFSFT | SYWMN | WVKQRPGQGLEWIG | YINP--STDYTDYNQKFKD | KATLTADKSSSTAYMQLSSPTSEDSAVYYCAT | RHYGSSYGF------AY | WGQGTSVTVSS |
| T427 | 12 | QVQLQQPGTELVRPGASVKLSCKASGFSFT | GYWMN | WVKQRPGQGLEWIG | MIHP--SDSETRLNQKFKD | RATLTVDKPSSTAYMQLSSPTSEDSAVYYCAS | EMDYYFAM-------DY | WGQGTSVTVSS |
| T405 | 13 | QVQLQQIGAELVRPGASVKLSCKASGYTFN | NYWIN | WVKQRPGQGLEWIG | NIYP--SDSRSNYNQKFKD | KATLTVDKPSSTAYMQLSSPTSEDSAVYYCTL | GS-------------Y | WGAGTLVTVSS |
| T105 | 14 | QVTLKESGPGILQPSQTLSLTCSFSGFSLS | TSGMGVS | WIRQPSGKDLEWLA | HIY---WDDDKRYNPSLKS | RLTISKDTSSNQVFLKITSVDTADTATYYCAR | RADGLYFYL------DV | WGAGTVTVSS |
| T201 | 38 | QVQLKESGPGLVAPSQSLSITCTVSGFSLI | DYGVS | WVRQPPGKGLEWLG | MIW---GDGNTDYNSGLKS | RLSISKDNSKSQVFLKVNSLQTDDTARYYCAR | PSTGTLF--------AY | WGQGTLVTVSA |
| T408 | 40 | QVQLQQPGAELVRPGASVKLSCKASGYTFT | SYWIN | WVKQRPGQGLEWIG | NIYP--SDSYSNYNQKFKD | KATLTVDKSSSTAYMQLSSPTSEDSAVYYCTL | GS-------------Y | WGQGTLVTVSA |

Fig 2b. Amino acid sequences of the variable regions of anti-CD30 MAbs

| VL | SEQ ID NO: | FR1 | CDR1 | FR2 | CDR2 | FR3 | CDR3 | FR4 |
|---|---|---|---|---|---|---|---|---|
| T6 | 15 | DIVMTQSQKFMSTSVGDRVSVTC | KASQ-----NVGTNVA | WYQQKPGQSPKALFY | SASYRYS | GVPDRFIGSGSGTVFTLTISNVQSEDLAEYFC | QQYNTYP-----LT | FGSGTKLEIERA |
| T7 | 16 | DIVLTQSPASLAVSLGQRATISC | RASESLEY-YGTTLMQ | WYQQKPGQPPKLLIY | AASNVES | GVPARFSGSGSGTDFSLNIHPVEEDDIAMYFC | HQSRKVP-----ST | FGGGTKLEIKRAD |
| T13 | 17 | DIVMTQSHKFMSTSVGDRVTITC | KASQ-----DVSTAVA | WYQQKPGHSPKLLIY | WASTRHT | GVPDRFTGSGSGTDYTLTISSVQVEDLALYYC | QQHYSTP-----FT | FGSGTKLEIKRA |
| T14-A | 18 | DVVMTQTPLSLPVSLGDQASISC | RSSQNLIHS-NGNAYLQ | WYLQKPGQSPKLLIY | KVSNRFS | GVPDRFSGSGSGTDFALKIIRVEAEDLGVYFC | SQTHVP-----YT | FGGGTKLEIKRAD |
| T14-B | 19 | DIVLTQSPASLAVSLGQRATISC | RASESLEY-YGTTLMQ | WYQQKPGQPPKLLIY | AASNVES | GVPARFSGSGSGTDFSLNIHPVEEDDIAMYFC | HQSRKVP-----ST | FGGGTKLEIKRAD |
| T21 | 20 | DIQMNQSPSSLSASLGDTITITC | HASQ-----NINVWLT | WYQQKPGNIPQLLIY | KASNLHT | GVPSRFSGSGSGTGFTLTISSLQPEDIATYYC | QQGQSYP-----LI | FGAGTKLELKRA |
| T24 | 21 | DIQMTQTTSSLSASLGDRVTISC | RASQ-----DISNYLN | WYQQKPDGTVKLLIY | YTSRLHS | GVPSRFSGSGSGTDYSLTISNLEQEDIATYFC | QQVNTLP-----RT | FGGGTKLEIKRA |
| T25 | 22 | DIVMSQSPSSLAVSVGEKFTVNC | KSSQSLLYSSNQKNFLA | WYQQKPGQSPKLLIY | WASTRES | GVPDRFIGSGSGTDFTLTISSVKAEDLAVYYC | QQHYRYP-----WT | FGGGTKLEIKRAR |
| HeF1-I | 23 | DIVLTQSPASLAVSLGQRATISC | RASKSVSA--SGYNYMH | WYQQKAGQPPKLLIH | LASNLES | GVPARFSGSGSGTDFTLNIHPVEEEDASTYYC | QHSGELP-----FT | FGSGTKLEIKRA |
| CL2 | 24 | DIVMTQSHKFMSTSVGDRVSVTC | KASQ-----NVGTNYA | WYQQKPGQSPKALIY | SASTRYS | GVPDRFTGSGSGTDFTLTISNVQSEDLAEYFC | QQYNSYP-----FT | FGSGTKLEIK |
| K1-4 | 25 | DIVLTQSHKSMAMSVGERVTLSC | KASE-----NVDSFVS | WYQQKPGQSPKALLY | GASNRHS | GVPDRFAGSGSGRDFTLTISSVQAEDLADYHC | QQNYRYP-----LI | FGAGTKLEIK |
| T420 | 26 | DIVMTQSHKFMSTSVGDRVSITC | KASQ-----DVSTAVA | WYQQKPGQSPKLLIY | WASTRHT | GVPDRFTGSGSGTDYSLTISSVQAEDLAVYYC | QQHYRTP-----FT | FGSGTKLEIKR |
| T427 | 27 | DIVLTQSPTSLAVSLGQRATISC | RASESVDS-YGNSFMH | WFQQKPGQPPKLLIY | RASNLES | GIPARFSGSGSGSWTDFTLTINPVEADDVATYYC | QQSNEDP-----RT | FGGGTKLEIKR |
| T405 | 28 | DVVMTQTPLTLSVTIGQPASISC | KSSQSLSDS-DGKTYLN | WLLQRPGQSPKRLIY | LVSKLDS | GVPDRFTGSGSGTDFTLKISRVEAEDLGVYYC | WQGAHFP-----RT | FGGGTKLEIKR |
| T105 | 29 | DIVMTQSQKFMSTSVGDRVSVTL | KASQ-----NVNTNVA | WYQQKPGQSPEALIY | SASYRYS | GVPDRFTGSGSGTDFTLTISNVQSEDLAEYFC | QQYNSYP-----LT | FGSGTKLEIKR |
| T201 | 39 | EIVLTQSPFTMAASPGERITFTC | SASSG-----ISSIYLH | WYQQKPGFSPKLLIY | RTSNLAS | GVPRFSGSGSGTSYSLTIGTMEABDVATYYC | QQGSSIP-----LI | FGAGTKLELKRA |
| T408 | 41 | DVVMTQTPLTLSVTIGQPASISC | KSSQSLSDS-DGKTYLN | WLLQRPGQSPKRLIY | LVSKLDS | GVPDRFTGSGSGTDFTLKISRVEAEDLGVYYC | WQGAHFP-----RT | FGGGTKLEIKRA |

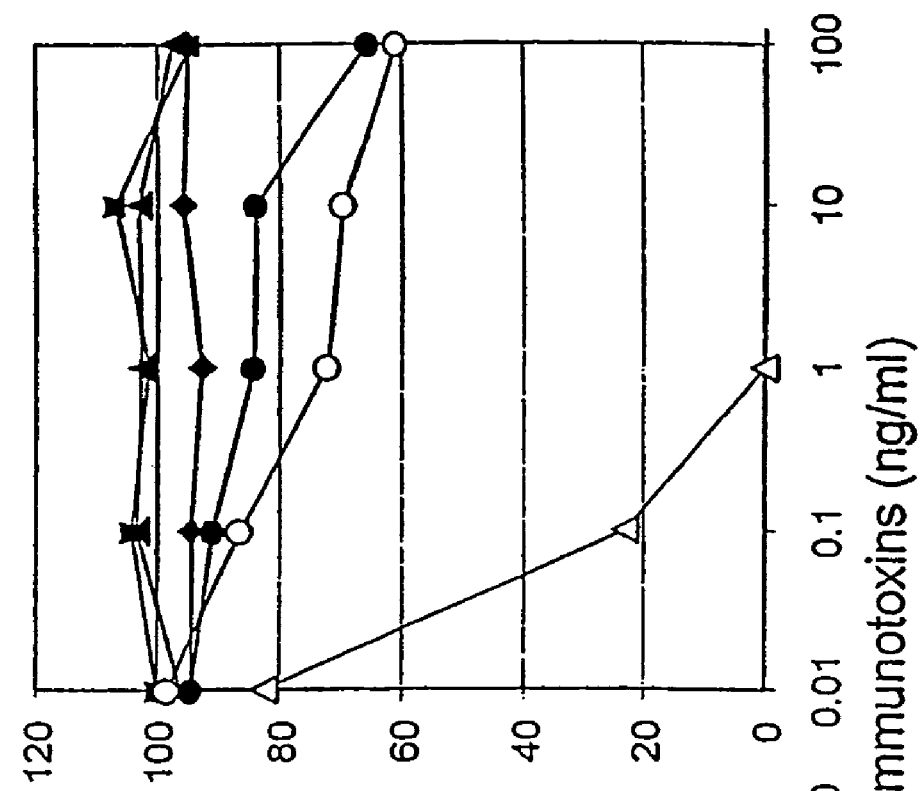
FIG. 4
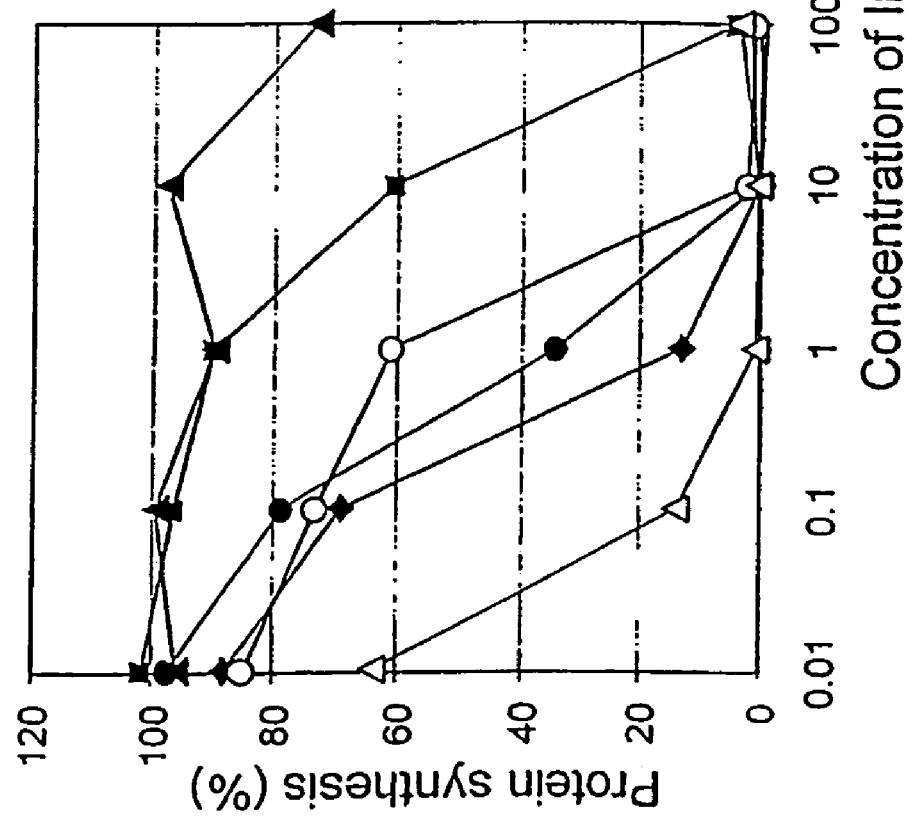
FIG. 4A
FIG. 4B

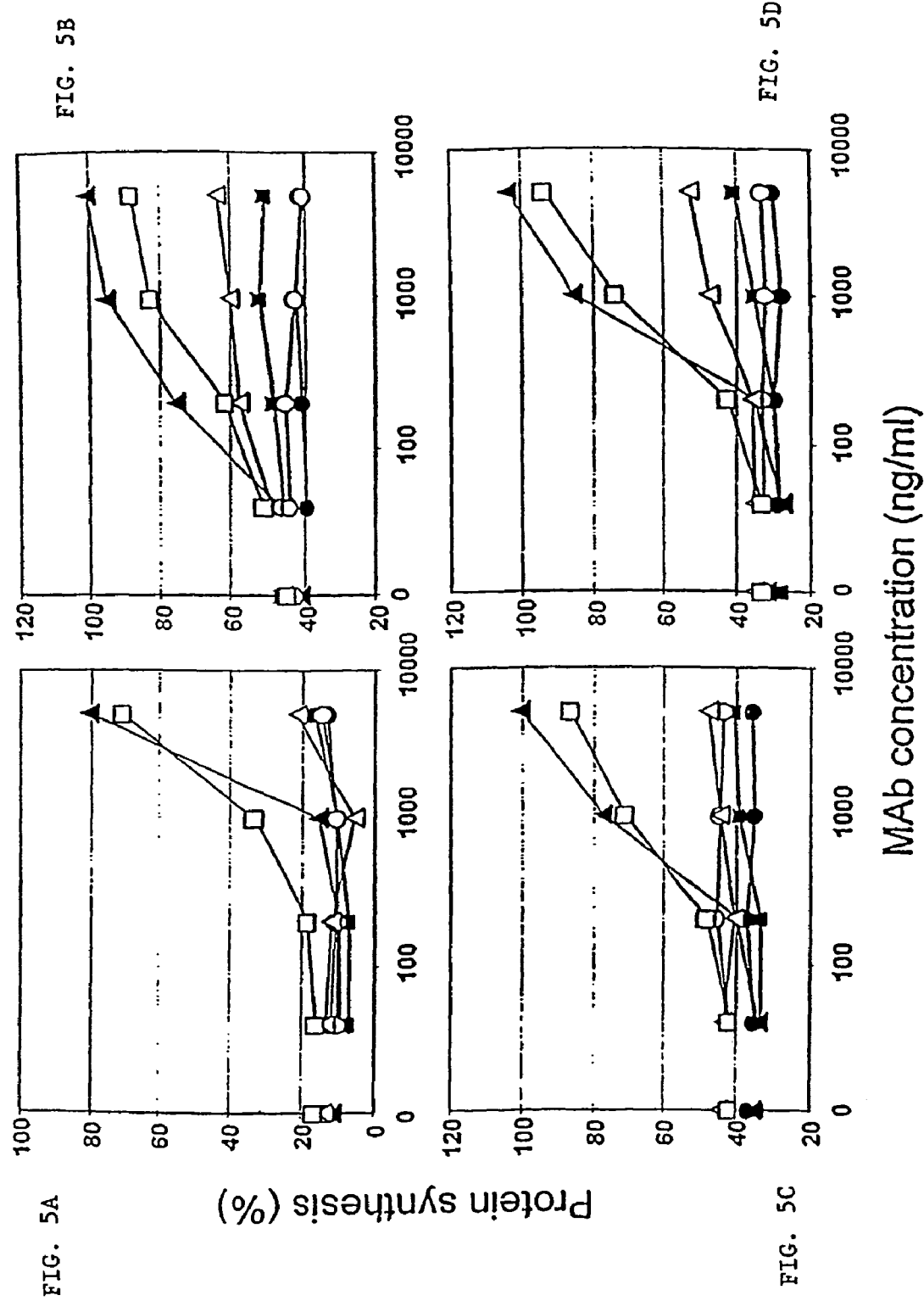

Fig. 6A  Karpas299 (CD30 positive)
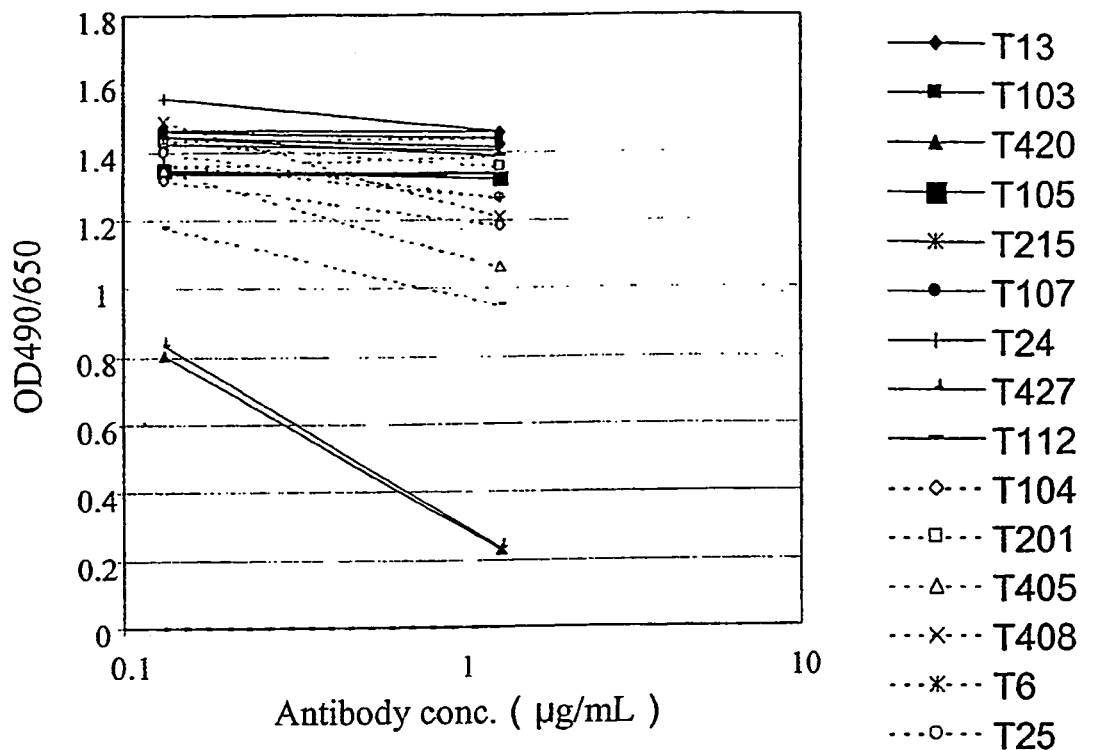
Fig. 6B  L540 (CD30 positive)
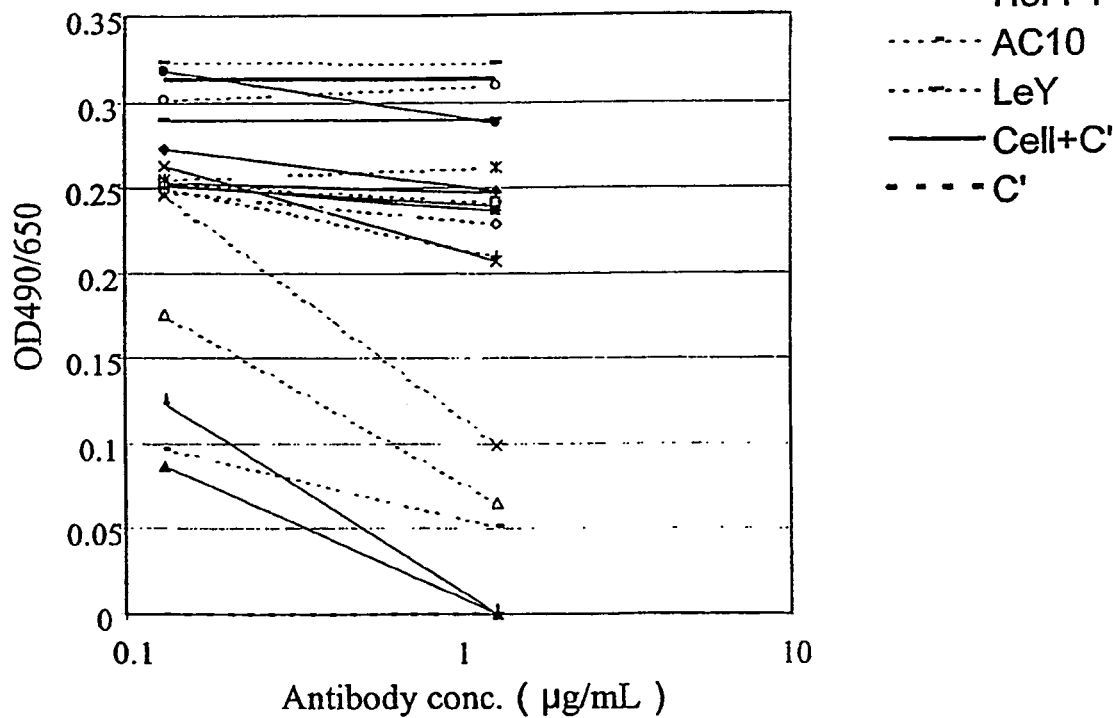

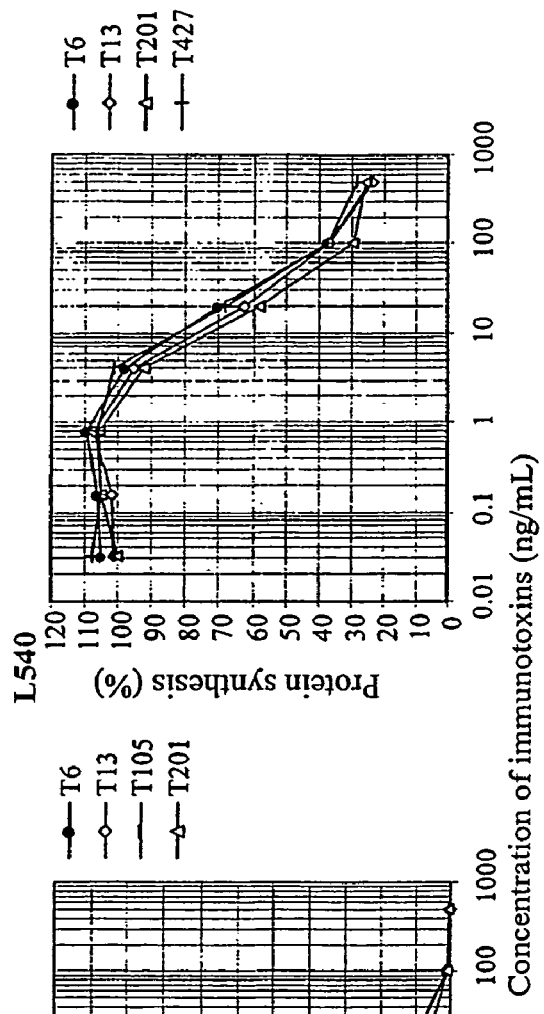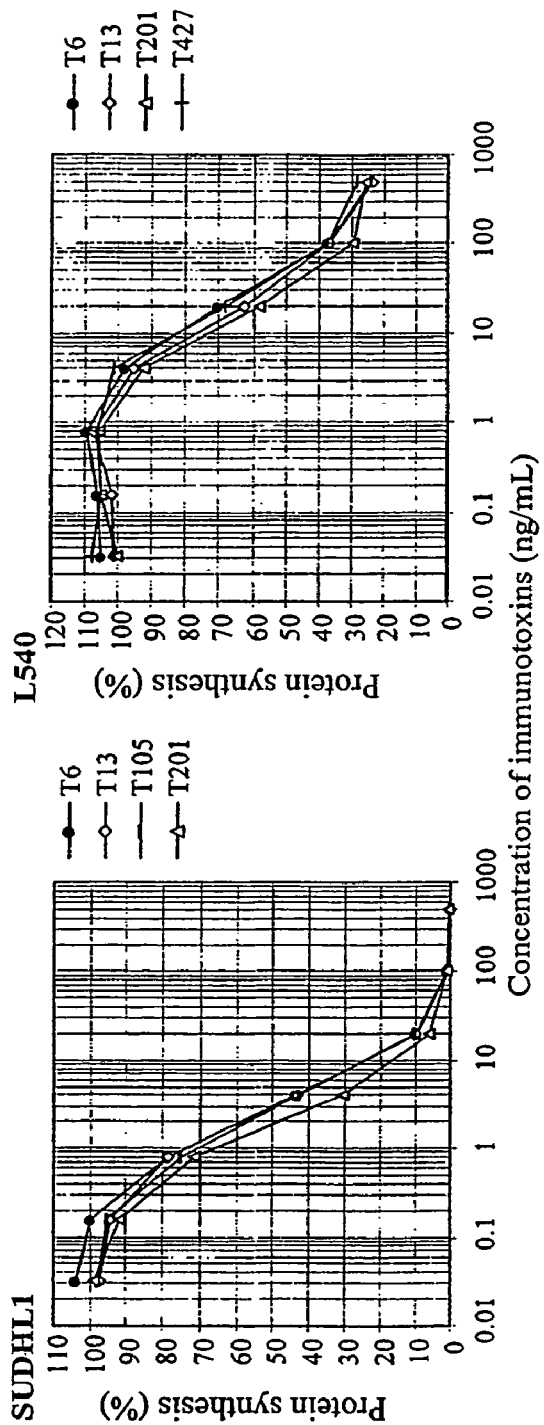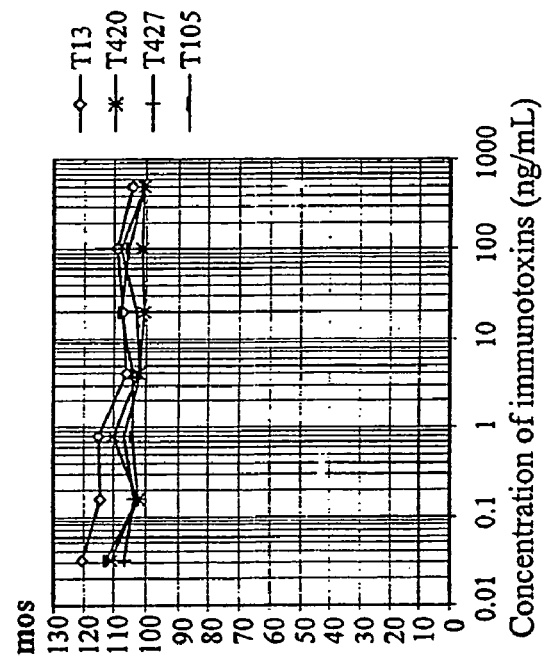

ANTI-CD30 STALK AND ANTI-CD30 ANTIBODIES SUITABLE FOR USE IN IMMUNOTOXINS

CROSS-REFERENCES TO RELATED APPLICATIONS

This application is a national stage filing under 35 U.S.C. §371 of PCT/US2003/018373, filed Jun. 9, 2003. This application also claims priority from and benefit of U.S. Provisional Application No. 60/387,293, filed Jun. 7, 2002, and U.S. Provisional Application No. 60/411,032, filed Sep. 16, 2002. The contents of both of these applications are incorporated herein for all purposes.

STATEMENT AS TO RIGHTS TO INVENTIONS MADE UNDER FEDERALLY SPONSORED RESEARCH AND DEVELOPMENT

Not applicable

REFERENCE TO A "SEQUENCE LISTING," A TABLE, OR A COMPUTER PROGRAM LISTING APPENDIX SUBMITTED ON A COMPACT DISK.

Not applicable

FIELD OF THE INVENTION

This invention relates to improved agents for detecting the presence of CD30-expressing cells ("CD30+ cells"), especially of CD30+ cancer cells, and for inhibiting their growth.

BACKGROUND OF THE INVENTION

Recombinant immunotoxins are chimeric proteins in which a truncated toxin is fused to an Fv portion of an antibody. The binding activity of the Fv moiety targets the immunotoxins to antigen-positive cells, which are killed by the cytotoxic activity of the toxin moiety (Pastan I., *Biochim. Biophys. Acta*, 1333:C1-C6 (1997); Kreitman R. J., *Curr. Opin. Immunol.*, 11:570-578 (1999)). For cancer therapy, a number of different recombinant immunotoxins have been produced using Fvs that bind to tumor-related antigens and differentiation antigens such as CD22 and CD25 and a 38-kDa mutant form of *Pseudomonas* exotoxin A ("PE38") that lacks its cell binding domain (Chaudhary et al., *Nature*, 339:394-397 (1989); Brinkmann et al., *Proc. Natl. Acad. Sci. U.S.A*, 88:8616-8620 (1991); Kreitman et al., *Blood*, 83:426-434 (1994); Mansfield et al., *Blood*, 90:2020-2026 (1997); Kreitman et al., *Int. J. Cancer*, 81:148-155 (1999)). The therapeutic potency of such immunotoxins has also been improved by protein engineering and chemical modification (Reiter et al., *Nat. Biotechnol.*, 14:1239-1245 (1996); Chowdhury et al., *Nat. Biotechnol.*, 17:568-572 (1999); Onda et al., *J. Immunol.*, 163:6072-6077 (1999); Tsutsumi et al., *Proc. Natl. Acad. Sci. U.S.A*, 97:8548-8553 (2000)). These efforts have been directed at making immunotoxins that are smaller for better tumor penetration, that are less immunogenic and less toxic to animals, that bind antigen with higher affinity, that are more stable, and that are suitable for large scale production (Kreitman R. J., *Curr. Opin. Immunol.*, 11:570-578 (1999); Brinkmann U., *In Vivo*, 14:21-27 (2000)).

One of the important advances is the development of disulfide-stabilized Fv fragments (dsFv) in which one of the variable chains genetically fused with PE38 is linked with the other chain by a disulfide bond between two cysteine residues engineered in the frame work region of each chain. These immunotoxins showed greater stability in vivo and in vitro than the widely used single-chain Fv (scFv) forms (Reiter et al., supra); Brinkmann et al., *Proc. Natl. Acad. Sci. USA*, 90:7538-7542 (1993); Reiter et al., *J. Biol. Chem.*, 269:18327-18331 (1994); Reiter et al., *Int. J. Cancer*, 67:113-123 (1996)).

Recent clinical trials indicate that targeted therapy by recombinant immunotoxins shows great promise especially for some types of hematologic malignancies. The anti-CD25 scFv immunotoxin, LMB-2, produced major clinical responses in various types of leukemia and lymphoma (Kreitman et al., *J. Clin. Oncol.*, 18:1622-1636 (2000)), and the anti-CD22 immunotoxin, RFB4(dsFv)-PE38, gave a remarkably high rate of complete remissions in patients with Hairy cell leukemia (Kreitman et al., *Clin. Cancer Res.*, 6:1476-1487 (2000); Kreitman et al., *N. Engl. J. Med.*, 345:241-247 (2001).

To extend the usefulness of immunotoxin therapy, it is important to develop immunotoxins against different targets. CD30 is a member of the tumor necrosis factor receptor super family. CD30 is an excellent target because it is usually highly expressed on malignant Reed Sternberg cells of Hodgkin's lymphoma (HL) and in anaplastic large cell lymphomas (ALCL), whereas it is only expressed in a small subset of normal lymphocytes and these can be resupplied from stem cells (Koon et al., *Curr. Opin. Oncol.*, 12:588-593 (2000)). Although its function is largely unknown, CD30 has been implicated both in cell death and proliferation (Lee et al., *J. Exp. Med*, 183:669-674 (1996); Wiley et al., *J. Immunol.*, 157:3635-3639 (1996); Mir et al., *Blood*, 96:4307-4312 (2000)). The possibility of using CD30 as a target for immunotoxin therapy has been investigated in earlier studies using anti-CD30 monoclonal antibodies (MAbs) chemically conjugated with toxins (Engert et al., *Cancer Res.*, 50:2929-2935 (1990); Terenzi et al., *Br. J. Haematol.*, 92:872-879 (1996); Engert et al., *Int. J. Cancer*, 63:304-309 (1995); Pasqualucci et al., *Blood*, 85:2139-2146 (1995)).

To obtain an anti-CD30 immunotoxin with better properties, recombinant immunotoxins have been produced. Klimka et al. reported the production of a recombinant immunotoxin derived from the anti-CD30 MAb Ki-4 by fusing its scFv to truncated PE (Klimka et al., *Br. J. Cancer*, 80:1214-1222 (1999)). Recently, the anti-tumor activity of this immunotoxin was reported in a SCID mouse model (Barth et al., *Blood*, 95:3909-3914 (2000)). The isolation of a new anti-CD30 scFv using the phage display technique and the properties of immunotoxins containing the scFv was also reported in Rozemuller et al., *Int. J. Cancer*, 92:861-870 (2001). All these recombinant immunotoxins showed specific binding to CD30-positive lymphoma cell lines and killed target cells as assessed by inhibition of protein synthesis with a 50% inhibition concentration ($IC_{50}$) of 40-50 pM. The cytotoxic activities were, however, much less than an immunotoxin that targets CD25 on these cells, which has an $IC_{50}$ of 0.2 pM (Reiter et al., *Clin. Cancer Res.*, 2:245-252 (1996)). Only a limited number of anti-CD30 Fvs have been suitable for making recombinant immunotoxins, and even with respect to these, the cytotoxic activities of the immunotoxins was only moderate.

The ability of an immunotoxin to kill a target cell is dependent on internalization. Although improving the affinity of the targeting portion of the immunotoxin is helpful, since this tends to increase the time the immunotoxin binds to the cell and therefore improves its opportunity to be internalized, affinity of the targeting portion of the immunotoxin, by itself, does not necessarily correlate with the immunotoxins' cell-killing ability. For example, the immunotoxin can be directed to a lysosome, where it is degraded, rather than to the cytosol, where the toxin can be released. Unfortunately, the state of the art does not yet permit predicting which antibodies will make good immunotoxins. Further, CD30 undergoes proteolytic cleavage, resulting in the release of a soluble portion of the protein, known as "sCD30." Immunotoxins which bind to sCD30 cleaved from intact CD30 are not available to be internalized into a target cell. Immunotoxins whose targeting portion binds to sCD30 must therefore be administered in larger quantities than might otherwise be desirable to compensate for loss of some of the immunotoxin by binding by free sCD30 in the extracellular fluids, such as the serum. This problem also extends to other immunoconjugates, such as a radioisotope attached to an antibody, to the extent that their cell killing or labeling abilities are reduced by binding to free sCD30 in the circulation. There remains a need in the art for immunotoxins directed against the CD30 antigen which have high cytotoxicity to target cells or which bind to intact CD30 but not to sCD30.

BRIEF SUMMARY OF THE INVENTION

It has now been discovered that a residual, extracellular "stalk" of CD30 (SEQ ID NO:1) remains after cleavage of sCD30. The stalk provides an advantageous and previously unrecognized target for immunotoxins. The invention provides antibodies that bind to the CD30 stalk or to epitopes destroyed upon the cleavage of CD30 which results in the stalk. The invention further relates to the discovery of new anti-CD30 antibodies that form effective immunotoxins and are particularly suitable for making disulfide stabilized Fv ("dsFv")-immunoconjugates.

In particular, this invention provides antibodies that bind specifically to a stalk of CD30 (SEQ ID NO:1) of a cell, or to an epitope destroyed upon cleavage of sCD30 from intact CD30. The antibody fragment can be an Fab, a recombinant single chain variable region, or a disulfide stabilized recombinant variable region ("dsFv"). In particularly preferred embodiments, the antibody or fragment thereof is a dsFv. In some embodiments, the antibody binds to a peptide consisting of residues 329 to 379 of CD30 (SEQ ID NO:1). In other embodiments, the antibody binds to a peptide consisting of residues 339 to 379 of CD30 (SEQ ID NO:1). In yet other embodiments, the antibody binds to a peptide consisting of residues 349 to 379 of CD30 (SEQ ID NO:1). In still other embodiments, the antibody binds to a peptide consisting of residues 359 to 379 of CD30 (SEQ ID NO:1). In still other embodiments, the antibody binds to a peptide consisting of residues 369 to 379 of CD30 (SEQ ID NO:1). In still other embodiments, the antibody binds to an epitope of CD30 mapping to residues 329 to 379 of CD30 (SEQ ID NO:1). In still other embodiments, the antibody binds to an epitope of CD30 mapping to residues 339 to 379 of CD30 (SEQ ID NO:1). In still other embodiments, the antibody binds an epitope of CD30 mapping to residues 349 to 379 of CD30 (SEQ ID NO:1). In still other embodiments, the antibody binds to an epitope of CD30 mapping to residues 359 to 379 of CD30 (SEQ ID NO:1). In still other embodiments, the antibody binds to an epitope of CD30 mapping to residues 369 to 379 of CD30 (SEQ ID NO:1). If the antibody binds an epitope that spans the cleavage site or is discontinuous but binds to both sCD30 and to the stalk, it is preferable that the antibody does not increase the rate of cleavage of sCD30 from the intact CD30. Preferably, the antibody binds to an epitope mapping to Epitopes IIa or VI of CD30. In preferred forms, the antibody has one or more complementarity determining regions as shown in FIGS. 2a and 2b for antibody T105 or of T201.

In another group of embodiments, the invention provides composition comprising any of the antibodies described above, attached to a therapeutic moiety. Typically, the antibody is attached to the therapeutic moiety by conjugation or by fusion (that is, the antibody-therapeutic moiety is expressed as a recombinant protein). In some embodiments, the therapeutic moiety is selected from the group consisting of a cytotoxin, a drug, a radioisotope, or a liposome loaded with a drug or a cytotoxin. In some embodiments, where the therapeutic moiety is a cytotoxin, the cytotoxin is selected from the group consisting of ricin A, abrin, ribotoxin, ribonuclease, saporin, calicheamycin, diphtheria toxin, a *Pseudomonas* exotoxin ("PE"), and botulinum toxins A through F. In some embodiments in which the cytotoxin is a PE, the PE can be selected from the group consisting of PE35, PE38, PE38 KDEL, PE40, PE4E, and PE38QQR. The compositions described above can further comprise a pharmaceutically acceptable carrier.

In another group of embodiments, the invention provides for the use of anti-CD30 antibody that binds specifically to a stalk of CD30 (SEQ ID NO:1) of a cell, on to an epitope destroyed upon cleavage of sCD30 from intact CD30, for the manufacture of a medicament to inhibit the growth of a CD30+ cancer cell. In some embodiments, the antibody can be selected from the group consisting of an scFv, dsFv, a Fab, or a F(ab')$_2$. In preferred embodiments, the antibody is a dsFv. The invention further provides for the use of a composition for the manufacture of a medicament for inhibiting growth of a CD30+ cancer cell, which composition comprises an antibody as just described conjugated or fused to a therapeutic moiety. In some embodiments, the therapeutic moiety is selected from the group consisting of a cytotoxin, a drug, a radioisotope, or a liposome loaded with a drug or a cytotoxin. In some embodiments where the therapeutic moiety is a cytotoxin, the cytotoxin can be ricin A, abrin, ribotoxin, ribonuclease, saporin, calicheamycin, diphtheria toxin, a *Pseudomonas* exotoxin ("PE"), or a botulinum toxin selected from A through F. In some embodiments, the cytotoxin is a PE. In some embodiments where the cytotoxin is a PE, the PE is PE35, PE38, PE38 KDEL, PE40, PE4E, or PE38QQR In some preferred embodiments, the PE is PE38.

In yet another group of embodiments, the invention provides nucleic acids encoding an antibody that binds specifically to a stalk of CD30 (SEQ ID NO:1) of a cell, or to an epitope destroyed upon cleavage of sCD30 from intact CD30. The antibody can be, for example, an scFv, a dsFv, a Fab, or a F(ab')$_2$. In particularly preferred embodiments, the antibody is a dsFv. The nucleic acid can further encode a polypeptide which is a therapeutic moiety. The therapeutic moiety can be a drug or a cytotoxin. In some embodiments, the cytotoxin can be ricin A, abrin, ribotoxin, ribonuclease, saporin, calicheamycin, diphtheria toxin, a *Pseudomonas* exotoxin ("PE"), or a botulinum toxin selected from A through F. In some preferred embodiments, the cytotoxin is a PE. In some embodiments where the cytotoxin is a PE, the PE is PE35, PE38, PE38 KDEL, PE40, PE4E, or PE38QQR In some preferred embodiments, the PE is PE38.

The invention further provides expression vectors comprising any of the nucleic acids described above operably linked to a promoter.

In another set of embodiments, the invention provides methods of inhibiting growth of a CD30+ cancer cell by contacting said cell with an antibody that binds specifically to a stalk of CD30 (SEQ ID NO:1) of a cell, or to an epitope destroyed upon cleavage of sCD30 from intact CD30, which antibody is fused or conjugated to a therapeutic moiety, which therapeutic moiety inhibits growth of said cell. The antibody can be, for example, an scFv, a dsFv, a Fab, or a F(ab')$_2$. In particularly preferred embodiments, the antibody is a dsFv. The therapeutic moiety can be a cytotoxin, a drug, a radioisotope, or a liposome loaded with a drug or a cytotoxin. In some embodiments where the therapeutic moiety is a cytotoxin, the cytotoxin can be ricin A, abrin, ribotoxin, ribonuclease, saporin, calicheamycin, diphtheria toxin, a *Pseudomonas* exotoxin ("PE"), or a botulinum toxin selected from A through F. In some preferred embodiments, the cytotoxin is a PE. In some embodiments where the cytotoxin is a PE, the PE is PE35, PE38, PE38 KDEL, PE40, PE4E, or PE38QQR. In some preferred embodiments, the PE is PE38.

In yet another group of embodiments, the invention provides anti-CD30 antibodies, wherein said antibodies comprise a sequence of at least one complementarity determining region ("CDR") shown in FIGS. 2a and b, of a sequence selected from the group consisting of SEQ ID NO:2, SEQ ID NO:4, SEQ ID NO:7, SEQ ID NO:14, SEQ ID NO:15, SEQ ID NO:17, SEQ ID NO:22, SEQ ID NO:29, SEQ ID NO:38, and SEQ ID NO:39. The invention further provides anti-CD30 antibodies, wherein the antibody has a variable heavy chain and a variable light chain, which chains have sequences selected from the group consisting of: a variable heavy chain of SEQ ID NO:2 and a variable light chain of SEQ ID NO:15 (antibody T6); a variable heavy chain having the sequence of SEQ ID NO:4 and a variable light chain having the sequence of SEQ ID NO:17 (antibody T13); a variable heavy chain of SEQ ID NO:7 and a variable light chain of SEQ ID NO:22 (antibody T25), and a variable heavy chain of SEQ ID NO:38 and a variable light chain of SEQ ID NO:39 (antibody T201). The antibodies can be disulfide stabilized recombinant variable regions ("dsFvs"). The invention further provides for compositions comprising any of the above-described antibodies conjugated or fused to a therapeutic moiety. The therapeutic moiety can be a cytotoxin, a drug, a radioisotope, or a liposome loaded with a drug or a cytotoxin. The cytotoxin can be selected from ricin A, abrin, ribotoxin, ribonuclease, saporin, calicheamycin, diphtheria toxin, a *Pseudomonas* exotoxin, and botulinum toxins A through F. In some embodiments, the cytotoxin is a *Pseudomonas* exotoxin ("PE"). In some embodiments, the PE is selected from the group consisting of PE35, PE38, PE38SKDEL, PE40, PE4E, and PE38QQR.

The invention further provides uses of anti-CD30 antibodies, wherein the antibodies comprise of at least one complementarity determining region ("CDR") shown in FIG. 2, of a sequence selected from the group consisting of SEQ ID NO:2, SEQ ID NO:4, SEQ ID NO:7, SEQ ID NO:14, SEQ ID NO:15, SEQ ID NO:17, SEQ ID NO:22, SEQ ID NO:29, SEQ ID NO:38, and SEQ ID NO:39 for the manufacture of a medicament to inhibit the growth of a CD30+ cancer cell. In some embodiments, the antibody is a dsFv.

Additionally, the invention provides the use of a composition for the manufacture of a medicament for inhibiting growth of a CD30+ cancer cell, which composition comprises any of the just-described antibodies conjugated or fused to a therapeutic moiety. In some embodiments, the therapeutic moiety is selected from the group consisting of a cytotoxin, a drug, a radioisotope, or a liposome loaded with a drug or a cytotoxin. In some preferred embodiments, the therapeutic moiety is a cytotoxin. In some of these embodiments, the cytotoxin can be selected from the group consisting of ricin A, abrin, ribotoxin, ribonuclease, saporin, calicheamycin, diphtheria toxin, a *Pseudomonas* exotoxin, and botulinum toxins A through F. In some preferred embodiments, the cytotoxin is a *Pseudomonas* exotoxin ("PE"). In some preferred embodiments, the PE is selected from the group consisting of PE35, PE38, PE38 KDEL, PE40, PE4E, and PE38QQR. In a particularly preferred embodiment, the PE is PE38.

Moreover, the invention further provides nucleic acids encoding an anti-CD30 antibody, wherein said encoded antibody comprises an amino acid sequence selected from the group consisting of: SEQ ID NO:2, SEQ ID NO:4, SEQ ID NO:7, SEQ ID NO:14, SEQ ID NO:15, SEQ ID NO:17, SEQ ID NO:22, SEQ ID NO:29, SEQ ID NO:38, and SEQ ID NO:39. The antibody encoded by the nucleic acid can be a dsFv. The nucleic acid can also further encode a polypeptide which is a therapeutic moiety. The therapeutic moiety can be, for example, a drug or a cytotoxin. The cytotoxin can be selected from the group consisting of ricin A, abrin, ribotoxin, ribonuclease, saporin, calicheamycin, diphtheria toxin, a *Pseudomonas* exotoxin, and botulinum toxins A through F. In some preferred embodiments, the cytotoxin is a *Pseudomonas* exotoxin ("PE"). In some preferred embodiments, the PE is selected from the group consisting of PE35, PE38, PE38 KDEL, PE40, PE4E, and PE38QQR. In a particularly preferred embodiment, the PE is PE38. The invention further provides expression vectors comprising any of the just-described nucleic acids operably linked to a promoter.

The invention further provides methods for inhibiting growth of a CD30+ cancer cell. The methods comprise contacting said cell with an antibody having at least one complementarity determining region as shown in FIG. 2, for SEQ ID NO:2, SEQ ID NO:4, SEQ ID NO:7, SEQ ID NO:14, SEQ ID NO:15, SEQ ID NO:17, SEQ ID NO:22, SEQ ID NO:29, SEQ ID NO:38, and SEQ ID NO:39, which antibody is fused or conjugated t, a therapeutic moiety, which therapeutic moiety inhibits growth of said cell. The antibody is preferably a dsFv. In some embodiments, the therapeutic moiety is selected from the group consisting of a cytotoxin, a drug, a radioisotope, or a liposome loaded with a drug or a cytotoxin. In some of these embodiments, the therapeutic moiety is a cytotoxin. Further, in some of these embodiments, the cytotoxin is selected from the group consisting of ricin A, abrin, ribotoxin, ribonuclease, saporin, calicheamycin, diphtheria toxin, a *Pseudomonas* exotoxin, and botulinum toxins A through F. In some preferred embodiments, the cytotoxin is a *Pseudomonas* exotoxin ("PE"). In some of these embodiments, the PE is selected from the group consisting of PE35, PE38, PE38 KDEL, PE40, PE4E, and PE38QQR.

In another group of embodiments, the invention provides methods for detecting the presence of a CD30+ cell in a biological sample, the methods comprising: (a) contacting cells of the biological sample with an anti-CD30 antibody selected from the group consisting of: an antibody that binds specifically to a stalk of CD30 (SEQ ID NO:1) of a cell, or to an epitope destroyed upon cleavage of sCD30 from intact CD30, and an antibody having at least one complementarity determining region as shown in FIG. 2 of SEQ ID NO:2, SEQ ID NO:4, SEQ ID NO:7, SEQ ID NO:14, SEQ ID NO:15, SEQ ID NO:17, SEQ ID NO:22, SEQ ID NO:29, SEQ ID NO:38, and SEQ ID NO:39, the antibody being fused or conjugated to a detectable label; and, (b) detecting the presence or absence of said label, wherein detecting the presence of the label indicates the presence of a CD30+ cell in said sample. In some embodiments, the antibody is selected from the group consisting of an scFv, a dsFv, a Fab, or a F(ab')$_2$.

In yet another group of embodiments, the invention provides antibodies useful for inducing complement-dependent cytotoxicity. In this regard, the invention provides antibodies having at least one complementarity determining region (CDR) from a variable heavy chain or variable light chain selected from the group consisting of SEQ ID NO:6, SEQ ID NO:11, SEQ ID NO:12, SEQ ID NO:13, SEQ ID NO:21, SEQ ID NO:26, SEQ ID NO:27, SEQ ID NO:28, SEQ ID NO:40, and SEQ ID NO:41. In preferred embodiments, the antibodies have the CDRs of a variable heavy chain and a variable light chain selected from the group consisting of: (a) SEQ ID NO:6, and SEQ ID NO:21 (antibody T24), (b) SEQ ID NO:11 and SEQ ID NO:26 (antibody T420), (c) SEQ ID NO:12 and SEQ ID NO:27 (antibody T427), (d) SEQ ID NO:13 and SEQ ID NO:28 (antibody T405), and (e) SEQ ID NO:40 and SEQ ID NO:41 (antibody T408). In preferred forms, the variable heavy and variable light chains have the sequences of these antibodies, preferably with mutations in the framework region which "humanize" them. The invention further provides compositions comprising any of the antibodies just described and a pharmaceutically acceptable carrier.

The invention further provides for the use of any of the antibodies described in the preceding paragraph for the manufacture of a medicament to inhibit the growth of cancer cells expressing CD30. Additionally, the invention provides methods for inhibiting the growth of cancer cells expressing CD30, said method comprising administering to a patient having a CD30-expressing cancer a therapeutically effective amount of an antibody having at least one CDR of a variable heavy chain or variable light chain selected from the group consisting of SEQ ID NO:6, SEQ ID NO:11, SEQ ID NO:12, SEQ ID NO:13, SEQ ID NO:21, SEQ ID NO:26, SEQ ID NO:27, SEQ ID NO:28, SEQ ID NO:40, and SEQ ID NO:41, as shown in FIGS. 2a and b. Preferably, the method comprises administering to a patient having a CD30-expressing cancer a therapeutically effective amount of an antibody having the complementarity determining regions ("CDRs") of variable heavy and variable light chains selected from the group consisting of (a) SEQ ID NO:6, and SEQ ID NO:21 (antibody T24), (b) SEQ ID NO:11 and SEQ ID NO:26 (antibody T420), (c) SEQ ID NO:12 and SEQ ID NO:27 (antibody T427), (d) SEQ ID NO:13 and SEQ ID NO:28 (antibody T405), and (e) SEQ ID NO:40 and SEQ ID NO:41 (antibody T408). In preferred embodiments, one or more residues in the framework regions of the variable regions are mutated to "humanize" the antibody to reduce immunogenicity.

In a further group of embodiments, the invention provides the use of an antibody having at least one complementarity-determining region of a mouse monoclonal antibody designated as AC10 for the manufacture of a medicament to inhibit the growth of cancer cells expressing CD30. In preferred forms, the antibody has variable heavy and variable light chains as in antibody AC10, and even more preferably, one or more residues in the framework regions of the variable regions are mutated to "humanize" the antibody to reduce immunogenicity. The invention further provides a method for inhibiting the growth of cancer cells expressing CD30, said method comprising administering to a patient having a CD30-expressing cancer a therapeutically effective amount of antibody having at least one complementarity-determining region ("CDR") of a mouse monoclonal antibody designated as AC10. The CDRs of the variable heavy and variable light chains of said antibody may be as in antibody AC10 and, in preferred forms, the variable heavy and variable light chains of said antibody are as in antibody AC10, and even more preferably, one or more residues in the framework regions of the variable regions are mutated to "humanize" the antibody to reduce immunogenicity.

The invention further provides isolated nucleic acids encoding an antibody having one or more the complementarity determining regions ("CDRs") of variable heavy and variable light chains selected from the group consisting of (a) SEQ ID NO:6, and SEQ ID NO:21 (antibody T24), (b) SEQ ID NO:11 and SEQ ID NO:26 (antibody T420), (c) SEQ ID NO:12 and SEQ ID NO:27 (antibody T427), (d) SEQ ID NO:13 and SEQ ID NO:28 (antibody T405), and (e) SEQ ID NO:40 and SEQ ID NO:41 (antibody T408). The isolated nucleic acids may encode an antibody having variable heavy and variable light chains selected from the group consisting of (a) SEQ ID NO:6, and SEQ ID NO:21 (antibody T24), (b) SEQ ID NO:11 and SEQ ID NO:26 (antibody T420), (c) SEQ ID NO:12 and SEQ ID NO:27 (antibody T427), (d) SEQ ID NO:13 and SEQ ID NO:28 (antibody T405), and (e) SEQ ID NO:40 and SEQ ID NO:41 (antibody T408). The invention also provides host cells expressing an isolated nucleic acid encoding an antibody having variable heavy and variable light chains selected from the group consisting of (a) SEQ ID NO:6, and SEQ ID NO:21 (antibody T24), (b) SEQ ID NO:11 and SEQ ID NO:26 (antibody T420), (c) SEQ ID NO:12 and SEQ ID NO:27 (antibody T427), (d) SEQ ID NO:13 and SEQ ID NO:28 (antibody T405), and (e) SEQ ID NO:40 and SEQ ID NO:41 (antibody T408).

The invention further provides kits for detecting the presence of a CD30+ cancer cell in a biological sample. The kits comprise (a) a container, and (b) an anti-CD30 antibody selected from the group consisting of: an antibody that binds specifically to a stalk of CD30 (SEQ ID NO:1) of a cell, or to an epitope destroyed upon cleavage of sCD30 from intact CD30, and an antibody that has at least one complementarity determining region having a sequence shown in FIG. 2 of SEQ ID NO:2, SEQ ID NO:4, SEQ ID NO:7, SEQ ID NO:14, SEQ ID NO:15, SEQ ID NO:17, SEQ ID NO:22, SEQ ID NO:29, SEQ ID NO:38, and SEQ ID NO:39, which anti-CD30 antibody is fused or conjugated to a detectable label. In some embodiments, the antibody in the kit is selected from the group consisting of an scFv, a dsFv, a Fab, or a F(ab')$_2$.

BRIEF DESCRIPTION OF THE DRAWINGS

FIG. 1. FIG. 1 is a cartoon showing six epitopes of CD30 as determined by competition binding experiments; the epitopes are designated by Roman numerals. The Figure shows a cell membrane (thick dark line at bottom of figure), with a representation of the CD30 molecule, showing the transmembrane and extracellular domains. The putative site at which sCD30 is cleaved from the stalk is shown by an arrow. Epitopes IIa and VI were determined to be non-shed epitopes. Ber-H2, HRS-4, Ki-4, HeFi-I, Ki-1, and M67 are previously known anti-CD30 antibodies. Antibodies designated with a "T" were generated in the course of the present invention. The relative size of the font for each antibody roughly corresponds with the affinity of the antibody for CD30. The location of each epitope was mapped by the following observations: 1) Epitopes ("Ep") II, III, IV are close to each other because some members of them showed cross competition for binding to CD30, 2) Ep I and III are a little correlated to each other for the same reason, 3) Ep I, III and IV are far from the cleavage site, 4) Ep IIb and V are close to the cleavage site, 5) Ep IIa and VI are non-shed epitopes or located on the cleavage site. 6)Ep I and Ep IIb are on or near the CD30L binding site. The position of the peptide chain is a representation. Underlined antibodies were tested as immunotoxins in an early series of studies. The plasma membrane of the cell is represented as a black curved line at bottom of figure. The extracellular portion of CD30 is positioned in the Figure above the line representing the plasma membrane, with the intracellular portion below the line representing the plasma membrane. As defined herein, the stalk is the portion of CD30 molecule from the first amino acid on the cell-proximal side of the cleavage site to the last amino acid on the extracellular side of the plasma membrane.

FIGS. 2a and 2b. FIGS. 2a and 2b set forth the amino acid sequences of the variable-regions of various anti-CD30 MAbs. FIG. 2a sets forth the sequences of the variable heavy chain ("VH"), while FIG. 2b sets forth the sequences of the respective variable light ("VL") chains. The MAbs are identified in the left hand column. The next column sets forth the SEQ ID NO for the amino acid sequence of the VH or VL, respectively, of the antibody named in the left hand column. DNA sequences of each VH or VL of the MAbs were determined by a RACE method and the deduced amino acid sequences were aligned according to their Kabat numbering. The calculated position of antigen complementarity determining regions (CDRs) and framework regions (FRs), based on alignments using the Kabat numbering system, are indicated in the first line of each panel. A subclone encoding a truncated VL sequence derived from SP2/O myeloma cells (Carroll et al., *Mol. Immunol.*, 25:991-995 (1988)) was obtained from T13 and T14 hybridoma, the sequence of which was omitted for simplification. CL2 (Rozemuller et al., Int. J. Cancer, 92:861-870 (2001)) and Ki-4 (Klimka et al., Br. J. Cancer, 80:1214-1222 (1999)) are previously known anti-CD30 Fv sequences.

FIGS. 3a-f. (FIGS. 3a to 3c are positioned in the top row, from left to right, FIGS. 3d to 3f are positioned in the bottom row and are likewise positioned in order from left to right). FIGS. 3a to 3f show FACS analysis of selected anti-CD30(dsFv)-PE38 immunotoxins on CD30-positive cells. The immunotoxins at various concentrations were incubated with L540 cells. The cell-bound immunotoxins were detected by anti-PE rabbit antibody and phycoerythrin-labeled anti-rabbit IgG. The five solid lines in each histogram from the left to right represent the staining with 0, 0.01, 0.1, 1, and 10 µg/ml of immunotoxins, respectively. For easier comparison, the areas of the staining with 1 µg/ml of immunotoxin are filled with gray color. The dotted line in each panel shows the staining with 1 µg/ml of immunotoxin in the presence of 10 µg/ml of CD30-Fc as the competitor. FIG. 3a: (denoted as T6), anti-CD30 T6(dsFv)PE38; FIG. 3b (denoted as T14-A): anti-CD30 T14-A(dsFv)-PE38; FIG. 3c (denoted as T24): anti-CD30 T24(dsFv)-PE38; FIG. 3d (denoted as T25): anti-CD30 T25(dsFv)-PE38; HB21, FIG. 3e (denoted as HB21:anti-tranferrin receptor HB21(scFv)-PE40 (a positive control); and FIG. 3f (denoted as SS1): anti-mesothelin SS1(dsFv)-PE38 (a negative control). Dose-dependent bindings were observed for all anti-CD30 immunotoxins and anti-transferrin receptor immunotoxin, although there was no binding of the anti-mesothelin immunotoxin. The binding of anti-CD30 immunotoxins was competed by free CD30-Fc antigen.

FIGS. 4a-b. FIG. 4 encompasses FIGS. 4a and 4b. FIG. 4a: Cytotoxicity of various immunotoxins on A431/CD30 cells. FIG. 4b: Cytotoxicity of various immunotoxins on A431/CD25 cells. For both Figures: Inhibition of protein synthesis was determined as percent $^3$H-leucine incorporation in cells after 24 h treatment with indicated concentrations of the immunotoxins. Closed symbols represents the data of selected anti-CD30-immunotoxins produced in the studies reported herein. Closed circle: T6(dsFv)-PE38; Closed triangle: T14-A(dsFv)-PE38; Closed square: T24(dsFv)-PE38; and Closed diamond; T25(dsFv)-PE38. Open symbols represents controls; Open circle: anti-CD30 CL2(scFv)-PE38; and Open triangle: anti-transferrin receptor HB21(scFv)-PE40. Triplicate sample values were averaged for each point.

FIGS. 5a-d. FIGS. 5a to 5d depict epitope-specific competitive effects of MAbs on the cytotoxicity of immunotoxins to various cell lines. Cells were treated with approximately 3-fold concentrations of IC$_{50}$ of T6(dsFv)-PE38 (closed symbols) or T25(dsFv)-PE38 (open symbols) in the presence of indicated concentrations of T6 MAb (closed and open triangles), T25 MAb (closed and open squares), or control mouse IgG1 (closed and open circle). After 24 h, protein synthesis of the cells was determined and expressed as the percent of the control. FIG. 5a: Cells tested were A431/CD30. FIG. 5b: Cells tested were KM-H2. FIG. 5c: Cells tested were SR-786. FIG. 5d: Cells tested were SUDHL-1. Each cell line was treated with 1.5, 60, 100, and 20 ng/ml of immunotoxins, respectively. Only the parent MAb, which bound the same epitope as the derived immunotoxins, inhibited the cytotoxicity of the immunotoxin on all cells.

FIGS. 6a and 6b. FIGS. 6a and 6b show complement-dependent cytotoxicity of intact antibodies assayed on two CD30+ cell lines, Karpas299 and L540, a Hodgkin's Disease cell line, as described in Example 6. The legend shows the symbols assigned to the antibodies tested. HeFi-1 and AC10 are antibodies known in the art. LeY designates an antibody that recognizes the LewisY antigen, used as a negative control. "Cell+C" designates cell plus complement only, meaning that antibody was not added to that culture, as a further control, while "C'" indicates complement only.

FIG. 7a shows the cytotoxicity of antibodies T6, T104, T201, and T408 on a cell line (A431) transfected to express CD30. FIG. 7b shows the cytotoxicity of the same immunotoxins on the same cell line, transfected to express the irrelevant antigen CD25 as a negative control.

FIGS. 8a, 8b and 8c. These graphs present the results of studies of the cytotoxicity of various immunotoxins made from antibodies of the invention. FIG. 8a shows the cytotoxicity of antibodies T6, T13, T105, and T201 on an anaplastic large cell lymphoma cell line, SUDHL1. FIG. 8b shows the cytotoxicity of the same immunotoxins on a Hodgkin's Disease cell line called L540. FIG. 8C shows the cytotoxicity of these immunotoxins on a cell line, Ramos, that does not express CD30, as a negative control.

DETAILED DESCRIPTION

I. Introduction

Figure 3:
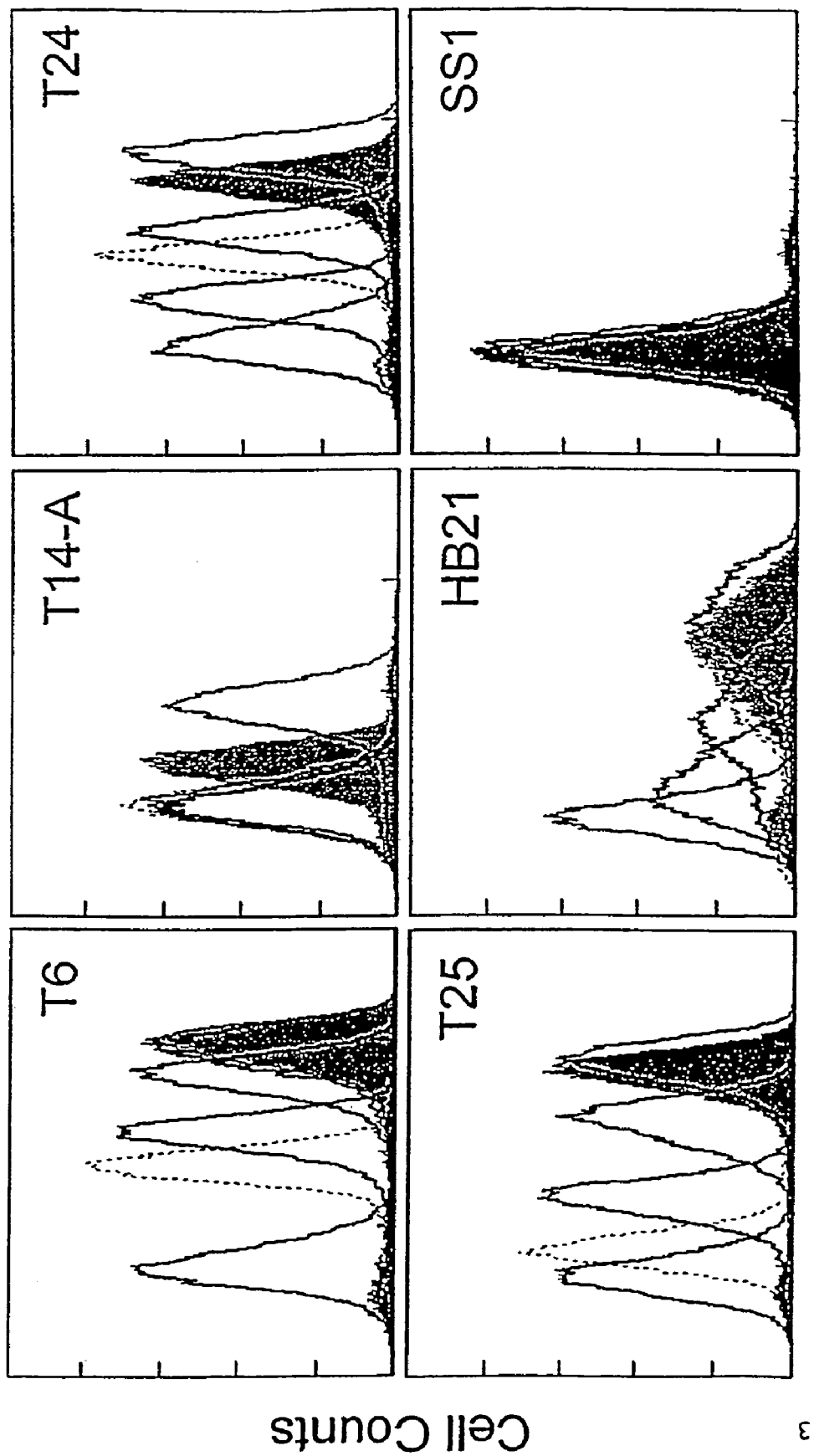
FIG. 3 encompasses six figures, denoted as FIGS. 3a to 3f, respectively.

A. Discovery of CD30 Stalk and Antibodies that Bind to It

CD30 was discovered in 1982, and was cloned in 1992. Durkop et at., Cell, 68:421-427 (1992), identified CD30 as a 595 amino acid protein with an 18 residue leader sequence, a 365 amino acid extracellular domain, a single transmembrane domain of 24 residues, and an intracellular domain of 188 residues. The amino acid sequence of CD30 (SEQ ID NO:1) was identified in the Durkop et al. publication. Durkop et al. identify the transmembrane domain as commencing on the N-terminal side with a proline at residue 380. The C-terminus of the extracellular domain is identified as a lysine at position 379, which may thus be considered as the amino acid of CD30 most proximal to the cell surface.

CD30 is known to undergo cleavage and to be released from the cell as soluble CD30 ("sCD30"). Surprisingly, it has now been discovered that the release of sCD30 leaves a residual, extracellular "stalk" on the side of the cleavage site proximal to the cell surface. The stalk provides a useful target for immunotoxins and other agents directed against CD30-expressing cells.

One purpose for employing ligands which bind to CD30 is to target toxic agents to cells expressing CD30. The presence of the stalk (which is also present on intact CD30), which remains attached to the cell following cleavage of sCD30, provides a target for improved CD30 ligands. Ligands that bind to the stalk region of CD30 can bind to intact CD30 on the cell surface, or to the stalk remaining after sCD30 is cleaved off. In either case, the ligands are then available for internalization into the cell and delivery of cytotoxins attached to the ligand. In contrast, ligands directed to portions of CD30 on the side of the cleavage site further from (distal to) the cell bind not only to intact CD30, but also to sCD30 that has been cleaved from the cell and that is now present in the extracellular fluids. The ligands binding to sCD30 free in the extracellular fluid cannot be internalized into the intended target cells. Accordingly, a correspondingly higher amount of such ligand-toxin conjugates need to be introduced to kill a given number of CD30-expressing cells compared to ligand-toxin conjugates targeted to the stalk. Ligands targeted to the stalk, or to epitopes which are destroyed upon cleavage of sCD30, are thus surprisingly advantageous in comparison to ligands which bind to portions of CD30 also found on sCD30. Since the existence of a stalk was not previously known, this advantage has not previously been recognized or exploited in the art. In one group of embodiments, the invention provides antibodies and other ligands that bind specifically to the stalk.

That is, the antibodies or other ligands bind to the stalk without binding in significant amounts to sCD30.

Prior studies of CD30 indicated that the antigenic epitopes fall into three groups. See, Horn-Lohrens, Int. J. Cancer 60:539-544 (1995). The careful competition studies and mapping performed in the studies reported herein indicate that there are instead six epitopes, two of which comprise two subgroups. Two of those epitopes, numbered herein IIa and VI, are considered to constitute the stalk region and are available for binding of ligands that do not also bind sCD30. FIG. 1 sets forth a cartoon of CD30, showing the epitopes as mapped by use both of anti-CD30 antibodies previously known in the art and antibodies generated in the course of the work embodied in the present invention.

It will be appreciated that some antibodies or ligands of the invention may bind to a binding site near or at the site at which sCD30 is cleaved from intact CD30, which binding site is destroyed upon cleavage of the sCD30. Without wishing to be bound by theory, such antibodies are expected to impede access to the cleavage site by endogenous proteases and thereby inhibit cleavage of sCD30. To the extent the binding site for the antibodies is either on the side of the cleavage site closer (proximal) to the cell, or is destroyed upon cleavage of sCD30, the antibodies are advantageous in that their effect is not "diluted" by binding to sCD30 free in the extracellular environment. To the extent that antibodies impeding cleavage bind to a site distal to the cleavage site, they are advantageous because, by impeding sCD30 cleavage, the antibody remains bound to CD30 and can still undergo internalization into the cell.

While the antibody Ki-4 was reported to inhibit cleavage of sCD30 (see, Horn-Lohrens, supra), it maps to an epitope far removed from the cleavage site, and thus does not bind to the regions now identified as belonging to the stalk or to the cleavage site. See, FIG. 1. Without wishing to be bound by theory, it is surmised that, although antibody Ki-4 binds to an epitope removed from the cleavage site, the conformation of the molecule is such that binding of the antibody to that site also happens to sterically hinder access of proteases to the cleavage site. The binding site for Ki-4, however, may not be destroyed by cleavage of sCD30, and the effect of Ki-4 based immunotoxins or immunoconjugates may therefore be "diluted" by binding to sCD30 free in the circulation.

Studies with sCD30 indicated that binding of antibodies Ki-1 and M67 (known in the art and specifically excluded from the antibodies of the invention), and antibody T104 (created in the course of the present work) to CD30 are partially inhibited by the presence of sCD30. Without wishing to be bound by theory, it is believed that these antibodies bind to discontinuous epitopes created by the three-dimensional conformation of the CD30 molecule (as opposed to linear epitopes created by the primary sequence of the amino acids), and that, upon the cleavage event that creates sCD30, part of the conformational epitope remains on the sCD30 and part remains on the stalk. Persons of skill will recognize that references to antibodies which bind to a particular amino acid sequence refer to a linear epitope, while references to an antibody mapping to a particular epitope refer to a conformational epitope.

It appears, however, that antibody Ki-1 increases the rate at which sCD30 is cleaved from intact CD30, possibly because it renders the cleavage site more accessible to proteases. Since binding of Ki-1 to CD30 is partially inhibited by the presence of sCD30, the tendency of Ki-1 to increase the shedding of sCD30 reduces the effectiveness of this antibody as a targeting agent. Moreover, a recent study of Ki-1 indicated that, while it bound strongly to two peptides from the N-terminus of CD30, it bound only weakly to a peptide close to the transmembrane domain. Dong et al., J. Mol. Recognit. 16:28-36 (2003). Thus, it would appear that immunotoxins using Ki-1 as the targeting portion would be more likely to bind to any sCD30 present around a tumor than to CD30 stalk remaining accessible on a cell surface.

Preferably, antibodies of the invention that bind to a discontinuous epitope, portions of which are on either side of the cleavage site, do not increase the rate of cleavage of sCD30 from intact CD30 (the rate of cleavage of sCD30 can be readily monitored and determined, for example by raising anti-sCD30 antibodies, changing the culture medium at timed intervals and measuring the amount of sCD30 present at each time point by an immunoassay using the anti-sCD30 antibodies). Additionally, it is desirable that targeting agents for immunotoxins targeted to CD30-expressing cells have a higher affinity for the stalk than for epitopes on a portion of the CD30 molecule released by the cleavage of sCD30.

Antibodies which bind to discontinuous epitopes that span the cleavage site may further be advantageous if they nonetheless form immunotoxins that display cytotoxicity to CD30+ cells comparable to that of immunotoxins that are in clinical trials for inhibition of other cancers, typically showing an $IC_{50}$ at amounts ranging from 0.2 to 20 ng/in L, more preferably having $IC_{50}$ values of less than 15 ng/mL, and still more preferably having $IC_{50}$ values below 10 ng/mL. T201 did not bind to CD30 in Western blots, indicating that it may bind to a discontinuous epitope, and may bind in part to sCD30. Cytotoxicity studies of a dsFv immunotoxin made with T201, however, indicate that it nonetheless forms potent immunotoxins to cells expressing CD30. Table 7 shows that T201, when made into a dsFv using an exemplar toxin, had an $IC_{50}$ in A431/CD30 cells of 0.6 ng/mL and an $IC_{50}$ in Karpas299 cells of 6 ng/mL.

Persons of skill recognize that the $IC_{50}$ of an immunotoxin to a cell lines typically vary because of various factors. For example, different cell lines tend to have different average number numbers of the target antigen or receptor present on the surface of the cells, have different rates of internalization of immunotoxins, and different rates of processing them internally to release the toxin moiety. Results in different cell lines therefore give some information on the relative potency of immunotoxins, with that information being of greater or lesser value as the cell line is judged to be similar to or different than CD30-expressing tumor cells from patients. The studies presented in Table 7 show that the antibodies of the invention are potent against lymphoma cells, such as anaplastic large cell lymphomas, but somewhat less potent against cell lines from Hodgkins' Disease. Accordingly, while the antibodies are useful against CD30-expressing cancers, their use against non-Hodgkins' lymphomas is preferred.

More preferably, the antibodies bind to Epitope IIa or Epitope VI of CD30. Whether a particular antibody binds to Epitope IIa or Epitope VI can be readily determined by following the assays set forth in the Examples. Antibodies binding to these epitopes, such as T105, have the advantage of not binding to sCD30 and therefore of not being diluted.

Preferred ligands of the invention bind to the first 100 extracellular amino acids proximal to the cell surface. In some embodiments, the ligands bind to a site within the first 80 amino acids on the extracellular portion of CD30 proximal to the cell-surface. In some embodiments, the ligands bind to a site within the first 75 amino acids on the extracellular portion of CD30 proximal to the cell-surface. In additional embodiments, the ligands bind to a site within the first 50 amino acids on the extracellular portion of CD30 proximal to the cell-surface. In other embodiments, the ligands bind to a site within the first 40 amino acids on the extracellular portion of CD30 proximal to the cell-surface. Further, in some embodiments, the ligands bind to site within about 30 amino acids on the extracellular portion of CD30 proximal to the cell-surface. Moreover, in some embodiments, the ligands bind to a site within about the first 20 amino acids on the extracellular portion of CD90 proximal to the cell-surface.

In preferred forms, the ligands are antibodies to CD30, or fragments thereof which retain their antigen recognition capability. Particularly preferred antibody fragments include single chain Fv fragments ("scFv") and disulfide stabilized Fv fragments ("dsFv"), with dsFv being especially preferred because of their stability. For convenience of reference, unless otherwise required by context, reference herein to "antibody" includes, as appropriate, reference to fragments of the antibody which retain antigen recognition.

It will be appreciated that intact antibodies are bivalent, while scFv and dsFv are monovalent, and that creating scFv or dsFv from an intact antibody typically results in a consequent loss of affinity compared to the antibody used as a starting material. Accordingly, to promote binding of immunoconjugates, such as immunotoxins, to the target cells, it is desirable that the antibody from which the scFv or dsFv is generated has a high affinity for the target antigen.

The work underlying the present invention has resulted in the discovery of antibodies which bind to the stalk region of CD30. These antibodies have been assigned the identifiers T104, T105, T405, T408, T201, T214, T215, T411, and T426. These antibodies are especially suitable antibodies for creation of immunotoxins targeted to CD30-expressing cancer cells. The antibodies T105, T201, and T405 are preferred, with T105 being particularly preferred.

The amino acid sequences of the variable regions of T105 and T201, including the antigen complementarity determining regions ("CDRs") are set forth in FIG. 2. FIG. 2 shows the sequences of various antibodies aligned according to the Kabat numbering of their residues (the Kabat system is the one most widely used in the art for aligning and comparing antibody residues). The sequence of the variable heavy ("$V_H$" chain of T105 is SEQ ID NO:14 and the variable light ("$V_L$") chain is SEQ ID NO:29, respectively. The sequence of the variable heavy ("$V_H$") chain of T201 is SEQ ID NO:38 and the variable light ("$V_L$") chain is SEQ ID NO:39, respectively.

B. Discovery of Advantageous Antibodies to Non-Stalk Portions of CD30

As noted in the Background section, smaller immunotoxins are less immunogenic and less toxic. These advantages are offset to some degree by the loss of antigen binding affinity that occurs when IgGs are converted from normal, bivalent antibodies to smaller, single-valent forms such as scFvs (Reiter et al., Nature Biotechnol. 14:239-1245 (1996)) and dsFvs suitable for making smaller immunotoxins. Increasing affinity has been shown to improve selective tumor delivery of scFvs (Adams et al., Cancer Res. 58:485-490 (1998)), and is likely to increase their usefulness in tumor imaging and treatment. Therefore, increasing the affinity of scFvs and other targeting moieties (such as dsFvs, Fabs, and F(ab')2 of immunoconjugates is advantageous to improve the efficiency of these agents in delivering effector molecules, such as toxins and other therapeutic agents, to their intended targets.

Unfortunately, it is hard to predict the affinity of immunotoxins from that of the original antibody, in part, because the change of the format of the Fv can affect the affinity. In addition, increased affinity alone cannot predict that an antibody will prove useful as the targeting portion of an immunotoxin. The antibody may bind so tightly to its target epitope that the binding may interfere with release of the toxic moiety upon internalization. Or, the antibody may bind to a portion of the target antigen (here, CD30) so removed from the cell surface that the immunotoxin is not efficiently internalized. Thus, increased affinity alone does not indicate that an antibody will prove useful as the targeting portion of an immunotoxin. Indeed, as shown in Table 6, infra, there is no clear correlation between the affinity of the original antibody to CD30 and that of an immunotoxin made from that antibody. Thus, it cannot be predicted from the affinity of an antibody whether it will permit the creation of an immunotoxin with satisfactory cytotoxicity.

Further, not all antibodies, whether of high-affinity or not, can be used successfully when converted to dsFvs. Satisfactory use of an antibody in dsFv form requires not only that the immunotoxin can be recombinantly expressed, but also that it can be refolded and purified in yields high enough to be useful as a reagent or for potential clinical use.

Surprisingly, several new antibodies have been discovered that can be made into dsFv immunotoxins which not only have suitably high affinity for CD30-expressing cells, but that also have cytotoxicity sufficient for clinical use and which can be produced with yields high enough so that the dsFvs can be made in the quantities needed for production for use as commercial reagents or making compositions for clinical use. These antibodies, designated, are advantageous because, among other things (a) they can be made into single chain Fvs ("scFvs") or disulfide-stabilized Fvs ("dsFvs"), (b) they can be expressed in sufficient quantities to be useful, and (c) although they are monovalent, they bind to CD30 with an affinity close to that of the intact, bivalent immunoglobulin. This combination of factors makes scFv and dsFv immunotoxins targeted by these new antibodies especially useful as reagents for purging CD30-expressing cancer cells from patient samples as well as for inhibiting the growth of CD30-expressing cancer cells in patients.

The amino acid sequences of the variable regions of antibodies T6, T13, T25, and T105, showing the antigen complementarity determining regions ("CDRs") and framework regions ("FRs") are set forth in FIG. 2, while those of antibody T201 is set forth in FIG. 6. FIGS. 2 and 6 show the sequences of the antibodies aligned according to the Kabat numbering of their residues (the Kabat system is the one most widely used in the art for aligning and comparing antibody residues). For example, the sequence of the variable heavy ("$V_H$") chain of T6 is SEQ ID NO:2 and the variable light ("$V_L$") chain is SEQ ID NO:15, respectively. The sequence of the $V_H$ chain of T25 is SEQ ID NO:7 and the sequence of the $V_L$ chain is SEQ ID NO:22, respectively, while the sequence of the $V_H$ chain of T13 is SEQ ID NO:4 and the sequence of the $V_L$ chain is SEQ ID NO:17, respectively.

As persons of skill are aware, the CDRs are responsible for some or all of an antibody's binding affinity and specificity. Persons of skill are also aware that, for example, conservative substitutions can typically be made in the framework regions (three of which are present in each variable light and heavy chain, as shown in the Figures), without significantly affecting antigen binding or specificity. Additionally, persons of skill will be aware that some substitutions can typically be made even in the CDRs without significantly affecting binding affinity or specificity. This is especially true for changes made in residues made at positions that are not within art-recognized "hotspot motifs" (such as the tetranucleotide sequence RGYW and the serine sequence AGY, where R is A or G, Y is C or T, and W is A or T). Any particular amino acid substitution can readily be tested to determine whether it has an affect on antigen binding or specificity by techniques well known in the art, such as those used in the Examples.

When made into dsFv immunotoxins using a mutated 38 kD form of *Pseudomonas* exotoxin ("PE38") as an exemplar toxic agent, T6, T25, and T201-dsFv-PE38 immunotoxins had $IC_{50}$s of 0.4-0.8 and 0.2-0.8 ng/ml, respectively, when tested on cells stably transfected with CD30. On cell lines of cancer cell lines expressing CD30, the cytotoxicity of the T6 and T25-based immunotoxins was comparable to that of dsFvs against other cancer antigens that are being developed for clinical use against cancers expressing those antigens.

Table 6 sets forth the results of studies in which the affinity of scFvs and of the cytotoxicity of PE38 immunotoxins made from dsFv forms of the antibodies were determined. A review of the Table reveals, for example, that scFvs made with T6 had an affinity ("kD") of 13.0 nM, while the affinity of antibody T24 was 2.2. nM. If higher affinity antibodies predictably made dsFv immunotoxins that had higher cytotoxicity to target cells than did antibodies with lower affinity, one would expect that T24 would make a more cytotoxic dsFv-immunotoxin than would T6. An examination of the Table, however, reveals that the amount of T24 immunotoxin needed to inhibit 50% of protein synthesis (known as the "$IC_{50}$", a standard means for comparing immunotoxin cytotoxicity) is 10.0 ng/ml, while the $IC_{50}$ for T6 immunotoxin is 0.4-0.8 ng/ml, or a cytotoxicity more than 12 times greater than that of the T24-based immunotoxin. Similarly, the T24 antibody has an affinity of 2.2 nM, roughly the same as the 1.9 nM kD of T420. The T420-based immunotoxin, however, has an IC50 of 1.5, some 6 times better than the 10.0 ng/ml IC50 of the T24-based immunotoxin. Thus, there is no clear correlation between the affinity of the "parental" immunotoxins and the cytotoxicity of the derived immunotoxin, illustrating that affinity alone does not permit prediction of which "parental" antibodies will produce a good immunotoxin and, in particular, which will produce a good dsFv.

C. Uses of Anti-CD30 and Anti-CD30 Stalk Antibodies

In in vitro uses, immunotoxins of the invention can be used to purge a blood sample or culture of CD30-expressing cancer cells from a patient. The purged sample can then be readministered to the patient to boost the functional white-blood cell population. Conversely, the purged cells can be transduced or used in other manipulations.

In in vivo uses, immunotoxins made with the antibodies or antibody fragments of the invention can be used to inhibit the growth and proliferation of cancer cells bearing the CD30 antigen. The properties of the antibodies and antibody fragments of the invention and of the resulting immunotoxins means that smaller amounts of the immunotoxins can be administered, thereby achieving the same therapeutic effect while reducing the chance of side effects. The results reported in the Examples show that the activity of the immunotoxins varies in different cell lines. In some embodiments, use of the immunotoxins of the invention is less preferred with respect to Hodgkin's Disease.

In preferred embodiments, the antibody is a scFv or a dsFv. Many of the recombinant immunotoxins produced from constructs of scFv are one-third the size of IgG-toxin chemical conjugates and are homogeneous in composition. Elimination of the constant portion of the IgG molecule from the scFv results in faster clearance of the immunotoxin after injection into animals, including primates, and the smaller size of the conjugates improves drug penetration in solid tumors. Together, these properties lessen the side effects associated with the toxic moiety by reducing the time in which the immunotoxin interacts with non-target tissues and tissues that express very low levels of antigen. Making disulfide stabilized Fvs (dsFvs) is discussed, e.g., in the co-owned application of FitzGerald et al., International Publication Number WO 98/41641.

D. Anti-CD30 Antibodies that Activate Complement-Dependent Cytotoxicity

As noted in the preceding sections, the present work has resulted in the discovery of anti-CD30 antibodies that are particularly good for use as the targeting portion of an immunotoxin. The present work has resulted in the discovery of anti-CD30 antibodies that are particularly good at activating complement-dependent cytotoxicity ("CDC"). In this embodiment of the invention, intact immunoglobulin molecules are used to bind to CD30-expressing cells, activating a complement cascade that results in the destruction of the cell. The antibodies preferred for this purpose are T405, T408, T420, and T427. As shown in FIGS. 6a and 6b, all four of these antibodies had significant activity against the Hodgkin's Disease cell line L540, and several had significant activity against the CD30+ cell line Karpas299. Persons of skill will recognize that it is the CDRs which confer antigen specificity. Accordingly, it is expected that antibodies with one or more CDRs of these antibodies will likewise induce CDC activity.

Studies were also performed using secondary antibodies. In these studies, antibody T24, which is of the IgG1 subclass, showed complement-dependent cytotoxicity activity. In humans, antibodies of IgG1 are useful in inducing CDC. Accordingly, it is expected that a humanized T24 antibody (for example, antibodies using one or more CDRs of T24) can also be used for induction of CDC.

Additionally, it was found that the previously known anti-CD30 antibody AC10 has significant complement-dependent cytotoxicity activity. AC10 is a mouse IgG2bκ antibody raised against human YT lymphoma cells and which is commercially available from a number of sources, including Ancell Corp. (Bayport, Minn.), Research Diagnostics, Ino. (Flanders, N.J.) and ID Labs, Inc. (London, Ontario, Canada). See also, Bowen, J. Immunol. 151:5896-5906 (1993) and Falini, Blood, 85:1-14 (1995). This is the first report that this antibody has complement-dependent cytotoxicity activity.

It appears from the studies performed in the course of the present work that antibodies that are effective at activating complement dependent cytotoxicity tend to be those that recognize epitope IIIB of CD30 and to be of the IgG2a and b subclasses. The sequences of the variable heavy and variable light antibodies of these antibodies are shown in the Figures and sequence listing.

The sequences of the constant region of the antibodies, including the Fc region, are not shown. Sequences of the constant regions of the IgG subclasses have been well known in the art for years (e.g., Honjo et al., Cell, 18:559-68 (1979); Tucker et al., Science, 206:1303-6 (1979); Yamawaki et al., Nature 283:786-9 (1980); Ellison et al., Nucl Acids Res 10:4071-9 (1982); Ellison et al., DNA 1:11-8 (1981); Ellison and Hood, Proc Natl Acad Sci USA 79:1984-8 (1982)). Since the CDRs of the variable regions determine antibody specificity, the CDRs shown in the Figures, or the Fvs, can be grafted or engineered into an antibody of choice to confer CD30-specificity upon that antibody. Moreover, the constant regions can be engineered to replace residues found in non-human animals, such as mice, with residues typically found in humans. Antibodies engineered in this way are referred to as "humanized antibodies" and are preferred, since they have a lower risk of inducing side effects and can remain in the circulation longer. Methods of humanizing antibodies are known in the art and are set forth in, for example, U.S. Pat. Nos. 6,180,377; 6,407,213; 5,693,762; 5,585,089; and 5,530, 101.

DEFINITIONS

Units, prefixes, and symbols are denoted in their Système International de Unites (SI) accepted form. Numeric ranges are inclusive of the numbers defining the range. Unless otherwise indicated, nucleic acids are written left to right in 5' to 3' orientation; amino acid sequences are written left to right in amino to carboxy orientation. The headings provided herein are not limitations of the various aspects or embodiments of the invention, which can be had by reference to the specification as a whole. Accordingly, the terms defined immediately below are more fully defined by reference to the specification in its entirety. Terms not defined herein have their ordinary meaning as understood by a person of skill in the art.

"CD30," also known as "Ki-1," is a human lymphocyte activation marker that is a member of the tumor necrosis factor receptor family highly overexpressed on cells of Hodgkin lymphoma and anaplastic large-cell lymphoma. Human CD30 was first identified in 1982 and was cloned in 1992. Durkop et al., Cell, 68:421-427 (1992). Durkop et al. identified CD30 as a 595 amino acid protein. The sequence is set forth by the National Center for Biotechnology Information (NCBI) under accession number XP_001744, and can be accessed on the NCBI website. As used herein, "CD30" refers to the activation marker and "Ki-1" refers to a specific antibody known in the art which binds the marker.

As used herein, the term "anti-CD30" in reference to an antibody or fragment retaining antigen recognition capability, refers to an antibody that specifically binds human CD30 and includes reference to an antibody which is generated against CD30.

"sCD30," or "soluble CD30" refers to that extracellular portion of CD30 which is proteolytically cleaved from intact CD30 and released into the extracellular fluid.

By "stalk" is meant the residual extracellular component of CD30 that corresponds to that region of CD30 that is bound to the cell following the proteolytic cleavage of CD30 that results in the release of sCD30. The stalk is present regardless of whether the segment of CD30 which corresponds to sCD30 is cleaved or uncleaved from CD30.

By "surface of the stalk" is meant the extracellular region of the stalk.

By "cell membrane proximal" or "cell surface proximal" is meant next to or nearer the cell membrane.

By "cell membrane distal" or "cell surface distal" is meant farther away from the cell membrane.

By "extracellular" is meant the region extending outward from the lipid bilayer encompassing a cell.

The term "epitope" is used herein in two senses. When in lower case, the term has the meaning usually understood in the art as the portion of an antigen that is recognized and bound by an antibody. When capitalized and followed by a Roman number (e.g., "Epitope VI"), it refers to a portion of CD30 defined by the competitive binding of various antibodies, as described in the Examples and in the Brief Description of FIG. 1.

By "specifically bind" is meant that no more than 15% of a ligand which specifically binds to a target molecule is bound to a particular non-target molecule. More preferably, no more than 10% is bound to the non-target molecule, even more preferably less than 5%, and most preferably less than 1%.

By "physiological conditions" is meant an extracellular milieu having conditions (e.g., temperature, pH, and osmolarity) which allows for the sustenance or growth of a cell of interest.

The term "*Pseudomonas* exotoxin" ("PE") as used herein can refer to a full-length native (naturally occurring) PE or to a PE that has been modified. Native *Pseudomonas* exotoxin A ("PE") is an extremely active monomeric protein (molecular weight 66 kD), secreted by *Pseudomonas aeruginosa*, which inhibits protein synthesis in eukaryotic cells. The native PE sequence is provided in commonly assigned U.S. Pat. No. 5,602,095. Modified forms of PE are discussed in detail herein in the section on Toxins, infra.

Cells are generally understood in the art to be bounded by a plasma membrane (herein referred to as the "cell membrane") comprising a lipid bilayer, in which proteins such as the ABC transporters are situated. See, generally, Alberts et al., Molecular Biology of the Cell, Garland Publishing, Inc., New York (3$^{rd}$ Ed., 1994), Chapter 10. The cell membrane may be considered to have a surface facing on the cytosol, or the interior of the cell, and a surface facing to the exterior of the cell, or the extracellular space. Transmembrane proteins such as CD30 are amphipathic, that is, they have regions that are hydrophobic and regions that are hydrophilic. Regions that pass through the membrane are hydrophobic and interact with the hydrophobic tails of the lipid molecules comprising the bilayer. Regions that are hydrophilic are exposed to water on either the cytosolic or the extracellular side of the membrane. Id. The transmembrane domain of transmembrane proteins are either in an alpha helix or multiple beta strands. Lodish et al., Molecular Cell Biology, W. E. Freeman and Co., New York (4th Ed., 2000), at chapter 3.

Portions of transmembrane proteins about 20-30 amino acid residues in length with a high degree of hydrophobicity are long enough to cross the membrane as an α-helix and can be identified by a hydropathy plot. E.g., Alberts et al., supra., Unless otherwise indicated, references herein to amino acid positions of antibody heavy or light chains refer to the numbering of the amino acids under the "Kabat and Wu" system. See, Kabat, E., et al., SEQUENCES OF PROTEINS OF IMMUNOLOGICAL INTEREST, U.S. Government Printing Office, NIH Publication No. 91-3242 (1991), which is hereby incorporated by reference (the Kabat and Wu database and numbering system are also referred to herein as the "Kabat" system and numbering). The Kabat and Wu database is the most widely used system in the art for numbering amino acid residues of antibodies and is now too large to be conveniently printed. It is now maintained online and can be found by entering "http://" followed by "immuno.bme.nwu.edu/". The number accorded to a residue under the Kabat and Wu system does not necessarily correspond to the number that one might obtain for a residue in a given heavy or light chain by counting from the amino terminus of that chain.

As used herein, "antibody" includes reference to an immunoglobulin molecule immunologically reactive with a particular antigen, and includes both polyclonal and monoclonal antibodies. The term also includes genetically engineered forms such as chimeric antibodies (e.g., humanized murine antibodies), heteroconjugate antibodies (e.g., bispecific antibodies) and recombinant single chain Fv fragments (scFv), and disulfide stabilized (dsFv) Fv fragments (see, U.S. Pat. No. 5,747,654, which is incorporated herein by reference). The term "antibody" also includes antigen binding forms or fragments of antibodies which retain antigen binding capability (e.g., Fab', F(ab')$_2$, Fab, Fv and rIgG). See also, Pierce Catalog and Handbook, 1994-1995 (Pierce Chemical Co., Rockford, Ill.); Kuby, J., *Immunology*, 3$^{rd}$ Ed., W. H. Freeman & Co., New York (1997).

An antibody immunologically reactive with a particular antigen can be generated by recombinant methods such as selection of libraries of recombinant antibodies in phage or similar vectors, see, e.g., Huse, et al., *Science* 246:1275-1281 (1989); Ward, et al., *Nature* 341:544-546 (1989); and Vaughan, et al., *Nature Biotech.* 14:309-314 (1996), or by immunizing an animal with the antigen or with DNA encoding the antigen.

Typically, an immunoglobulin has a heavy and light chain. Each heavy and light chain contains a constant region and a variable region, (the regions are also known as "domains"). Light and heavy chain variable regions contain a "framework" region interrupted by three hypervariable regions, also called "complementarity-determining regions" or "CDRs". The extent of the framework region and CDRs have been defined. See, Kabat and Wu, supra. The sequences of the framework regions of different light or heavy chains are relatively conserved within a species. The framework region of an antibody, that is the combined framework regions of the constituent light and heavy chains, serves to position and align the CDRs in three dimensional space.

The CDRs are primarily responsible for binding to an epitope of an antigen. The CDRs of each chain are typically referred to as CDR1, CDR2, and CDR3, numbered sequentially starting from the N-terminus, and are also typically identified by the chain in which the particular CDR is located.

Thus, a $V_H$ CDR3 is located in the variable domain of the heavy chain of the antibody in which it is found, whereas a $V_L$ CDR1 is the CDR1 from the variable domain of the light chain of the antibody in which it is found.

References to "$V_H$" or a "VH" refer to the variable region of an immunoglobulin heavy chain, including an Fv, scFv, dsFv or Fab. References to "$V_L$" or a "VL" refer to the variable region of an immunoglobulin light chain, including of an Fv, scFv, dsFv or Fab The phrase "single chain Fv" or "scFv" refers to an antibody in which the variable domains of the heavy chain and of the light chain of a traditional two chain antibody have been joined to form one chain. Typically, a linker peptide is inserted between the two chains to allow for proper folding and creation of an active binding site.

The term "linker peptide" includes reference to a peptide within an antibody binding fragment (e.g., Fv fragment) which serves to indirectly bond the variable domain of the heavy chain to the variable domain of the light chain.

The term "parental antibody" means any antibody of interest which is to be mutated or varied to obtain antibodies or fragments thereof which bind to the same epitope as the parental-antibody, but with higher affinity.

The term "hotspot" means a portion of a nucleotide sequence of a CDR or of a framework region of a variable domain which is a site of particularly high natural variation. Although CDRs are themselves considered to be regions of hypervariability, it has been learned that mutations are not evenly distributed throughout the CDRs. Particular sites, or hotspots, have been identified as these locations which undergo concentrated mutations. The hotspots are characterized by a number of structural features and sequences. These "hotspot motifs" can be used to identify hotspots. Two consensus sequences motifs which area especially well characterized are the tetranucleotide sequence RGYW and the serine sequence AGY, where R is A or G, Y is C or T, and W is A or T.

A "targeting moiety" is the portion of an immunoconjugate intended to target the immunoconjugate to a cell of interest. Typically, the targeting moiety is an antibody, or a fragment of an antibody that retains antigen recognition capability, such as a scFv, a dsFv, an Fab, or an F(ab')$_2$.

A "toxic moiety" is the portion of a immunotoxin which renders the immunotoxin cytotoxic to cells of interest.

A "therapeutic moiety" is the portion of an immunoconjugate intended to act as a therapeutic agent.

The term "therapeutic agent" includes any number of compounds currently known or later developed to act as anti-neoplastics, anti-inflammatories, cytokines, anti-infectives, enzyme activators or inhibitors, allosteric modifiers, antibiotics or other agents administered to induce a desired therapeutic effect in a patient. The therapeutic agent may also be a toxin or a radioisotope, where the therapeutic effect intended is, for example, the killing of a cancer cell.

A "detectable label" means, with respect to an immunoconjugate, a portion of the immunoconjugate which has a property rendering its presence detectable. For example, the immunoconjugate may be labeled with a radioactive isotope which permits cells in which the immunoconjugate is present to be detected in immunohistochemical assays.

The term "effector moiety" means the portion of an immunoconjugate intended to have an effect on a cell targeted by the targeting moiety or to identify the presence of the immunoconjugate. Thus, the effector moiety can be, for example, a therapeutic moiety, such as a toxin, a radiolabel, or a fluorescent label.

The term "immunoconjugate" includes reference to a covalent linkage of an effector molecule to an antibody (the effector molecule is referred to as an effector moiety upon conjugation to the antibody, which can then be referred to as a targeting moiety). The effector molecule can be, for example, a toxin.

The terms "effective amount" or "amount effective to" or "therapeutically effective amount" includes reference to a dosage of a therapeutic agent sufficient to produce a desired result, such as inhibiting cell protein synthesis by at least 50%, or killing the cell.

The term "toxin" includes reference to abrin, ricin, *Pseudomonas* exotoxin (PE), diphtheria toxin (DT), botulinum toxin, or modified toxins thereof. For example, PE and DT are highly toxic compounds that typically bring about death through liver toxicity. PE and DT, however, can be modified into a form for use as an immunotoxin by removing the native targeting component of the toxin (e.g., domain Ia of PE or the B chain of DT) and replacing it with a different targeting moiety, such as an antibody.

The term "contacting" includes reference to placement in direct physical association.

An "expression plasmid" comprises a nucleotide sequence encoding a molecule or interest, which is operably linked to a promoter.

As used herein, "polypeptide", "peptide" and "protein" are used interchangeably and include reference to a polymer of amino acid residues. The terms apply to amino acid polymers in which one or more amino acid residue is an artificial chemical analogue of a corresponding naturally occurring amino acid, as well as to naturally occurring amino acid polymers. The terms also apply to polymers containing conservative amino acid substitutions such that the protein remains functional.

The term "residue" or "amino acid residue" or "amino acid" includes reference to an amino acid that is incorporated into a protein, polypeptide, or peptide (collectively "peptide"). The amino acid can be a naturally occurring amino acid and, unless otherwise limited, can encompass known analogs of natural amino acids that can function in a similar manner as naturally occurring amino acids.

The amino acids and analogs referred to herein are described by shorthand designations as follows in Table A:

TABLE A

Amino Acid Nomenclature

| Name | 3-letter | 1-letter |
|---|---|---|
| Alanine | Ala | A |
| Arginine | Arg | R |
| Asparagine | Asn | N |
| Aspartic Acid | Asp | D |
| Cysteine | Cys | C |
| Glutamic Acid | Glu | E |
| Glutamine | Gln | Q |
| Glycine | Gly | G |
| Histidine | His | H |
| Homoserine | Hse | — |
| Isoleucine | Ile | I |
| Leucine | Leu | L |
| Lysine | Lys | K |
| Methionine | Met | M |
| Methionine sulfoxide | Met (O) | — |
| Methionine methylsulfonium | Met (S—Me) | — |
| Norleucine | Nle | — |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

A "conservative substitution", when describing a protein refers to a change in the amino acid composition of the protein that does not substantially alter the protein's activity. Thus, "conservatively modified variations" of a particular amino acid sequence refers to amino acid substitutions of those amino acids that are not critical for protein activity or substitution of amino acids with other amino acids having similar properties (e.g., acidic, basic, positively or negatively charged, polar or non-polar, etc.) such that the substitutions of even critical amino acids do not substantially alter activity. Conservative substitution tables providing functionally similar amino acids are well known in the art. The following six groups in Table B each contain amino acids that are conservative substitutions for one another:

TABLE B

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

See also, Creighton, PROTEINS, W. H. Freeman and Company, New York (1984).

The terms "substantially similar" in the context of a peptide indicates that a peptide comprises a sequence with at least 90%, preferably at least 95% sequence identity to the reference sequence over a comparison window of 10-20 amino acids. Percentage of sequence identity is determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The phrase "disulfide bond" or "cysteine-cysteine disulfide bond" refers to a covalent interaction between two cysteines in which the sulfur atoms of the cysteines are oxidized to form a disulfide bond. The average bond energy of a disulfide bond is about 60 kcal/mol compared to 1-2 kcal/mol for a hydrogen bond. In the context of this invention, the cysteines which form the disulfide bond are within the framework regions of the single chain antibody and serve to stabilize the conformation of the antibody.

The terms "conjugating," "joining," "bonding" or "linking" refer to making two polypeptides into one contiguous polypeptide molecule. In the context of the present invention, the terms include reference to joining an antibody moiety to an effector molecule (EM). The linkage can be either by chemical or recombinant means. Chemical means refers to a reaction between the antibody moiety and the effector molecule such that there is a covalent bond formed between the two molecules to form one molecule.

As used herein, "recombinant" includes reference to a protein produced using cells that do not have, in their native state, an endogenous copy of the DNA able to express the protein. The cells produce the recombinant protein because they have been genetically altered by the introduction of the appropriate isolated nucleic acid sequence. The term also includes reference to a cell, or nucleic acid, or vector, that has been modified by the introduction of a heterologous nucleic acid or the alteration of a native nucleic acid to a form not native to that cell, or that the cell is derived from a cell so modified. Thus, for example, recombinant cells express genes that are not found within the native (non-recombinant) form of the cell, express mutants of genes that are found within the native form, or express native genes that are otherwise abnormally expressed, underexpressed or not expressed at all.

As used herein, "nucleic acid" or "nucleic acid sequence" includes reference to a deoxyribonucleotide or ribonucleotide polymer in either single- or double-stranded form, and unless otherwise limited, encompasses known analogues of natural nucleotides that hybridize to nucleic acids in a manner similar to naturally occurring nucleotides. Unless otherwise indicated, a particular nucleic acid sequence includes the complementary sequence thereof as well as conservative variants, i.e., nucleic acids present in wobble positions of codons and variants that, when translated into a protein, result in a conservative substitution of an amino acid.

As used herein, "encoding" with respect to a specified nucleic acid, includes reference to nucleic acids which comprise the information for translation into the specified protein. The information is specified by the use of codons. Typically, the amino acid sequence is encoded by the nucleic acid using the "universal" genetic code. However, variants of the universal code, such as is present in some plant, animal, and fungal mitochondria, the bacterium *Mycoplasma capricolum* (*Proc. Nat'l Acad. Sci. USA* 82:2306-2309 (1985), or the ciliate *Macronucleus*, may be used when the nucleic acid is expressed in using the translational machinery of these organisms.

The phrase "fusing in frame" refers to joining two or more nucleic acid sequences which encode polypeptides so that the joined nucleic acid sequence translates into a single chain protein which comprises the original polypeptide chains.

As used herein, "expressed" includes reference to translation of a nucleic acid into a protein. Proteins may be expressed and remain intracellular, become a component of the cell surface membrane or be secreted into the extracellular matrix or medium.

By "host cell" is meant a cell which can support the replication or expression of the expression vector. Host cells may be prokaryotic cells such as *E. coli*, or eukaryotic cells such as yeast, insect, amphibian, or mammalian cells.

The phrase "phage display library" refers to a population of bacteriophage, each of which contains a foreign cDNA recombinantly fused in frame to a surface protein. The phage display the foreign protein encoded by the cDNA on its surface. After replication in a bacterial host, typically *E. coli*, the phage which contain the foreign cDNA of interest are selected by the expression of the foreign protein on the phage surface.

The terms "identical" or percent "identity," in the context of two or more nucleic acids or polypeptide sequences, refer to two or more sequences or subsequences that are the same or have a specified percentage of amino acid residues or nucleotides that are the same, when compared and aligned for maximum correspondence, as measured using one of the following sequence comparison algorithms or by visual inspection.

The phrase "substantially identical," in the context of two nucleic acids or polypeptides, refers to two or more sequences or subsequences that have at least 60%, more preferably 65%, even more preferably 70%, still more preferably 75%, even more preferably 80%, and most preferably 90-95% nucleotide or amino acid residue identity, when compared and aligned for maximum correspondence, as measured using one of the following sequence comparison algorithms or by visual inspection. Preferably, the substantial identity exists over a region of the sequences that is at least about 50 residues in length, more preferably over a region of at least about 100 residues, and most preferably the sequences are substantially identical over at least about 150 residues. In a most preferred embodiment, the sequences are substantially identical over the entire length of the coding regions.

For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group; 575 Science Dr., Madison, Wis.), or by visual inspection (see generally, *Current Protocols in Molecular Biology*, F. M. Ausubel et al., eds., Current Protocols, a joint venture between Greene Publishing Associates, Inc. and John Wiley & Sons, Inc., (1995 Supplement) (Ausubel)).

Examples of algorithms that are suitable for determining percent sequence identity and sequence similarity are the BLAST and BLAST 2.0 algorithms, which are described in Altschul et al. (1990) *J. Mol. Biol.* 215: 403-410 and Altschuel et al. (1977) *Nucleic Acids Res.* 25: 3389-3402, respectively. Software for performing BLAST analyses is publicly available through the National Center for Biotechnology Information (and can be found online by entering "http:// www.", followed by "ncbi.nlm.nih.gov/"). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4, and a comparison of both strands. For amino acid sequences, the BLASTP program uses as defaults a wordlength (W) of 3, an expectation (E) of 10, and the BLOSUM62 scoring matrix see Henikoff & Henikoff, *Proc. Natl. Acad. Sci. USA* 89:10915 (1989)).

In addition to calculating percent sequence identity, the BLAST algorithm also performs a statistical analysis of the similarity between two sequences (see, e.g., Karlin & Altschul, *Proc. Nat'l. Acad. Sci USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

A further indication that two nucleic acid sequences or polypeptides are substantially identical is that the polypeptide encoded by the first nucleic acid is immunologically cross reactive with the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules hybridize to each other under stringent conditions, as described below.

The term "in vivo" includes reference to inside the body of the organism from which the cell was obtained. "Ex vivo" and "in vitro" means outside the body of the organism from which the cell was obtained.

The phrase "malignant cell" or "malignancy" refers to tumors or tumor cells that ate invasive and/or able to undergo metastasis, ie., a cancerous cell.

As used herein, "mammalian cells" includes reference to cells derived from mammals including humans, rats, mice, guinea pigs, chimpanzees, or macaques. The cells may be cultured in vivo or in vitro.

The term "selectively reactive" refers, with respect to an antigen, the preferential association of an antibody, in whole or part, with a cell or tissue bearing that antigen and not to cells or tissues lacking that antigen. It is, of course, recognized that a certain degree of non-specific interaction may occur between a molecule and a non-target cell or tissue. Nevertheless, selective reactivity, may be distinguished as mediated through specific recognition of the antigen. Although selectively reactive antibodies bind antigen, they may do so with low affinity. On the other hand, specific binding results in a much stronger association between the antibody and cells bearing the antigen than between the bound antibody and cells lacking the antigen. Specific binding typically results in greater than 2-fold, preferably greater than 5-fold, more preferably greater than 10-fold and most preferably greater than 100-fold increase in amount of bound antibody (per unit time) to a cell or tissue bearing CD30 as compared to a cell or tissue lacking CD30. Specific binding to a protein under such conditions requires an antibody that is selected for its specificity for a particular protein. A variety of immunoassay formats are appropriate for selecting antibodies specifically immunoreactive with a particular protein. For example, solid-phase ELISA immunoassays are routinely used to select monoclonal antibodies specifically immunoreactive with a protein. See Harlow & Lane, ANTIBODIES, A LABORATORY MANUAL, Cold Spring Harbor Publications, New York (1988), for a description of immunoassay formats and conditions that can be used to determine specific immunoreactivity.

The term "immunologically reactive conditions" includes reference to conditions which allow an antibody generated to a particular epitope to bind to that epitope to a detectably greater degree than, and/or to the substantial exclusion of, binding to substantially all other epitopes. Immunologically reactive conditions are dependent upon the format of the antibody binding reaction and typically are those utilized in immunoassay protocols or those conditions encountered in vivo. See Harlow & Lane, supra, for a description of immunoassay formats and conditions. Preferably, the immunologically reactive conditions employed in the methods of the present invention are "physiological conditions" which include reference to conditions (e.g., temperature, osmolarity, pH) that are typical inside a living mammal or a mammalian cell. While it is recognized that some organs are subject to extreme conditions, the intra-organismal and intracellular environment normally lies around pH 7 (i.e., from pH 6.0 to pH 8.0, more typically pH 6.5 to 7.5), contains water as the predominant solvent, and exists at a temperature above 0° C. and below 50° C. Osmolarity is within the range that is supportive of cell viability and proliferation.

Identification of the Stalk

The stalk can be identified by a variety of techniques well known to those of skill. Determining the presence and level of sCD30 in the serum is well known in the art. E.g., Blanco Quiros et al., Pediatr Allergy Immunol, 10:235-40 (1999); Bottari et al., Allergy, 54:507-10 (1999). sCD30 can be readily isolated by conventional techniques well known in the art, such as by immobilizing CD30 antibodies that bind sCD30 on a column or other solid support, contacting the antibodies with serum shown to contain sCD30, and eluting the bound sCD30 from the column or other support. The isolated sCD30 can then be sequenced by amino acid sequencing methods well known to those of skill, such as Edman degradation or mass spectrometry. As noted above, the sequence of intact CD30 is known, and the putative transmembrane domain has been identified. Durkop et al., supra. The stalk is therefore readily identified as the portion of the CD30 sequence that is situated between the end of the transmembrane domain of CD30 on the extracellular side of the cell membrane, on the one hand, and the carboxyl-terminus of sCD30, on the other. The cleavage site is also readily determined by comparison of the sequences of sCD30 and CD30.

Binding Ligands to the Stalk

A host of methods for construction and selection of ligands such as nucleic acids, proteins or peptides (collectively, "peptides), or antibodies, or small organics or inorganics (e.g., U.S. Pat. No. 5,143,854; WO 90/15070; WO 92/10092; WO 96/11878) having the desired specific binding characteristics are well known in the art. Preferably, ligands of the present invention will, under physiological conditions, bind to the stalk without substantially binding to sCD30. More preferably, the ligands of the present invention specifically bind only to the stalk under physiological conditions. A ligand may be chosen to bind to an extracellular ligand binding site contained within, for example, the first 6, 9, 12, 15, 18, 21, 24, 27, 30, 33, 35, 37, 39, 41, 43, 45, 47, 49, 51, 53, 55, 57, 60, 63, 66, 69, 72, or 75 membrane-proximal amino acids of the stalk.

Antibodies, including polyclonal, monoclonal, or recombinant single chain Fv antibodies, can be constructed for use as ligands in the present invention. Methods of producing polyclonal and monoclonal antibodies are known to those of skill in the art. See, e.g., Coligan (1991) Current Protocols in Immunology Wiley/Greene, N.Y.; and Harlow and Lane (1989) Antibodies: A Laboratory Manual Cold Spring Harbor Press, N.Y.; Stites et al. (eds.) Basic and Clinical Immunology (4th ed.) Lange Medical Publications, Los Altos, Calif., and references cited therein; Goding (1986) Monoclonal Antibodies: Principles and Practice (2d ed.) Academic Press, New York, N.Y.; and Kohler and Milstein (1975) Nature 256: 495-497; Huse et al. (1989) Science 246: 1275-1281; Ward, et al. (1989) Nature 341: 544-546. Birch and Lennox, Monoclonal Antibodies: Principles and Applications, Wiley-Liss, N.Y., N.Y. (1995).

Other suitable techniques for antibody or peptide ligand preparation include selection of libraries of recombinant antibodies/peptides in phage or similar vectors. High affinity antibodies and peptides to the stalk can be rapidly isolated by using phage display methods to express recombinant single chain Fv (scFv) fragments or peptide ligands on the phage surface. Briefly, genes encoding the surface protein of a phage are altered so as to allow the insertion of an antibody or peptide gene which is expressed as a fusion protein on the surface of the phage that carries the gene. The phage expressing the desired antibody or peptide ligand can be selectively enriched and isolated by virtue of its affinity/avidity for the stalk. The DNA encoding the ligand is packaged in the same phage and which allows the gene encoding the ligand to be isolated. A variety of such methods are amply discussed in the literature and well known to the skilled artisan. See, e.g., Winter et al., Annu. Rev. Immunol. 12:433455 (1994); Marks et al., J. Mol. Biol. 222:581-597 (1991); Vaughan et al., Nature Biotechnology 14:309-314 (1996), U.S. Pat. Nos. 4,642,334; 4,816,397; 4,816,567; 4,704,692; WO 86/01533; WO 88/09344; WO 89/00999; WO 90/02809; WO 90/04036; EP 0 324 162; EP 0 239 400.

In chemical peptide synthesis, a procedure termed "Divide, Couple and Recombine" (DCR) has been used to produce combinatorial peptide libraries. See, Furka et al, Int. J. Pept. Protein Res. 37:487-493 (1991) and Houghten et al., Nature 354:84-86 (1991). As an alternative to DCR, peptide mixtures have also been made by direct coupling of monomer mixtures. See, Rutter et al., U.S. Pat. No. 5,010,175. The use of such methods to produce mixtures of other linear polymers, such as "peptoids", has been suggested. See, Simon, et al, Proc. Natl. Acad. Sci. USA 89:9367-9371 (1992). In oligonucleotide synthesis, "degenerate" or "wobble" mixtures of oligonucleotide products can be made by, for example, delivery of equimolar mixtures of monomers to an oligonucleotide polymer at specific steps during synthesis. See, Atkinson and Smith, in "Oligonucleotide Synthesis. A Practical Approach", 1984, IRL Press, Oxford, edited by M. Gait, pp 35-81. These methods of synthesizing peptides or oligonucleotides provide large numbers of compounds for testing which, if active, can be readily identified.

Preferably, ligands will be constructed to minimize immunogenicity in the host as, for example, by maximizing the number of autologous (self) sequences present in the ligand. Accordingly, chimeric antibodies having non-xenogenic variable regions are preferred. Particularly preferred are the use of antibodies in which xenogenic portions are excluded, or are essentially limited to the complementarity determining regions as in humanized antibodies.

Ligand Binding and Testing

Binding (i.e., attachment) of the ligand to the stalk of CD30 may occur prior or subsequent to cleavage of sCD30.

Binding affinity of antibodies to a target antigen is typically measured or determined by standard antibody-antigen assays, such as competitive assays, saturation assays, or immunoassays such as ELISA or RIA. Such assays can be used to determine the dissociation constant of the antibody. The phrase "dissociation constant" refers to the affinity of an antibody for an antigen. Specificity of binding between an antibody and an antigen exists if the dissociation constant (KD=1/K, where K is the affinity constant) of the antibody is <1□M, preferably <100 nM, and most preferably <0.1 nM. Antibody molecules will typically have a KD in the lower ranges. KD=[Ab–Ag]/[Ab][Ag] where [Ab] is the concentration at equilibrium of the antibody, [Ag] is the concentration at equilibrium of the antigen and [Ab–Ag] is the concentration at equilibrium of the antibody-antigen complex. Typically, the binding interactions between antigen and antibody include reversible noncovalent associations such as electrostatic attraction, Van der Waals forces and hydrogen bonds.

The antibodies can be detected and/or quantified using any of a number of well recognized immunological binding assays (see, e.g., U.S. Pat. Nos. 4,366,241; 4,376,110; 4,517,288; and 4,837,168). For a review of the general immunoassays, see also METHODS IN CELL BIOLOGY, VOL. 37, Asai, ed. Academic Press, Inc. New York (1993); BASIC AND CLINICAL IMMUNOLOGY 7TH EDITION, Stites & Terr, eds. (1991). Immunological binding assays (or immunoassays) typically utilize a ligand (e.g., CD30) to specifically bind to and often immobilize an antibody. In a preferred embodiment, the immunoassay is a radioimmunoassay.

Immunoassays also often utilize a labeling agent to specifically bind to and label the binding complex formed by the ligand and the antibody. The labeling agent may itself be one of the moieties comprising the antibody/analyte complex, i.e., an anti-CD30-stalk antibody). Alternatively, the labeling agent may be a third moiety, such as another antibody, that specifically binds to the antibody/CD30 stalk complex.

In one aspect, a competitive assay is contemplated wherein the labeling agent is a second anti-CD30 stalk antibody bearing a label. The two antibodies then compete for binding to the immobilized CD30 stalk. Alternatively, in a non-competitive format, the anti-CD30 stalk antibody lacks a label, but a second antibody specific to antibodies of the species from which the anti-CD30 stalk antibody is derived, e.g., murine, and which binds the anti-CD30 stalk antibody, is labeled.

Other proteins capable of specifically binding immunoglobulin constant regions, such as Protein A or Protein G may also be used as the label agent. These proteins are normal constituents of the cell walls of streptococcal bacteria. They exhibit a strong non-immunogenic reactivity with immunoglobulin constant regions from a variety of species (see, generally Kronval, et al., J. Immunol. 111:1401-1406 (1973); and Akerstrom, et al., J. Immunol. 135:2589-2542 (1985)).

Throughout the assays, incubation and/or washing steps may be required after each combination of reagents. Incubation steps can vary from about 5 seconds to several hours, preferably from about 5 minutes to about 24 hours. However, the incubation time will depend upon the assay format, antibody, volume of solution, concentrations, and the like. Usually, the assays will be carried out at ambient temperature, although they can be conducted over a range of temperatures, such as 10° C. to 40° C.

While the details of the immunoassays of the present invention may vary with the particular format employed, the method of detecting anti-CD30 stalk antibodies in a sample containing the antibodies generally comprises the steps of contacting the sample with an antibody which specifically reacts, under immunologically reactive conditions, to the CD30 stalk/antibody complex.

Production of Immunoconjugates

Immunoconjugates include, but are not limited to, molecules in which there is a covalent linkage of a therapeutic agent to an antibody. A therapeutic agent is an agent with a particular biological activity directed against a particular target molecule or a cell bearing a target molecule. One of skill in the art will appreciate that therapeutic agents may intrude various drugs such as vinblastine, daunomycin and the like, cytotoxins such as native or modified *Pseudomonas* exotoxin or Diphtheria toxin, encapsulating agents, (e.g., liposomes) which themselves contain pharmacological compositions, radioactive agents such as $^{125}I$, $^{32}P$, $^{14}C$, $^{3}H$ and $^{35}S$ and other labels, target moieties and ligands. (Such therapeutic agents are sometimes referred to herein as "effector molecules".)

The choice of a particular therapeutic agent depends on the particular target molecule or cell and the biological effect is desired to evoke. Thus, for example, the therapeutic agent may be a cytotoxin which is used to bring about the death of a particular target cell. Conversely, where it is merely desired to invoke a non-lethal biological response, the therapeutic agent may be conjugated to a non-lethal pharmacological agent or a liposome containing a non-lethal pharmacological agent.

With the therapeutic agents and antibodies herein provided, one of skill can readily construct a variety of clones containing functionally equivalent nucleic acids, such as nucleic acids which differ in sequence but which encode the same effector molecule ("EM") or antibody sequence. Thus, the present invention provides nucleic acids encoding antibodies and conjugates and fusion proteins thereof.

A. Recombinant Methods

Nucleic acid sequences encoding the chimeric molecules of the present invention can be prepared by any suitable method including, for example, cloning of appropriate sequences or by direct chemical synthesis by methods such as the phosphotriester method of Narang, et al., *Meth. Enzymol.* 68:90-99 (1979); the phosphodiester method of Brown, et al., *Meth. Enzymol.* 68:109-151 (1979); the diethylphosphoramidite method of Beaucage, et al., *Tetra. Lett.* 22:1859-1862 (1981); the solid phase phosphoramidite triester method described by Beaucage & Caruthers, *Tetra. Letts.* 22(20): 1859-1862 (1981), e.g., using an automated synthesizer as described in, for example, Needham-VanDevanter, et al. *Nucl. Acids Res.* 12:6159-6168 (1984); and, the solid support method of U.S. Pat. No. 4,458,066. Chemical synthesis produces a single stranded oligonucleotide. This may be converted into double stranded DNA by hybridization with a complementary sequence, or by polymerization with a DNA polymerase using the single strand as a template. One of skill would recognize that while chemical synthesis of DNA is limited to sequences of about 100 bases, longer sequences may be obtained by the ligation of shorter sequences.

In a preferred embodiment, the nucleic acid sequences of this invention are prepared by cloning techniques. Examples of appropriate cloning and sequencing techniques, and instructions sufficient to direct persons of skill through many cloning exercises are found in Sambrook, et al., supra, Berger and Kimmel (eds.), supra, and Ausubel, supra Product information from manufacturers of biological reagents and experimental equipment also provide useful information. Such manufacturers include the SIGMA chemical company (Saint Louis, Mo.), R&D systems (Minneapolis, Minn.), Pharmacia Amersham (Piscataway, N.J.), CLONTECH Laboratories, Inc. (Palo Alto, Calif.), Chem Genes Corp., Aldrich Chemical Company (Milwaukee, Wis.), Glen Research, Inc., GIBCO BRL Life Technologies, Inc. (Gaithersburg, Md.), Fluka Chemica-Biochemika Analytika (Fluka Chemie AG, Buchs, Switzerland), Invitrogen (San Diego, Calif.), and Applied Biosystems (Foster City, Calif.), as well as many other commercial sources known to one of skill.

Nucleic acids encoding anti-CD30 or CD30 stalk antibodies can be modified to form the EM, antibodies, or immunoconjugates of the present invention. Modification by site-directed mutagenesis is well known in the art. Nucleic acids encoding EM or CD30 or CD30 stalk antibodies can be amplified by in vitro methods. Amplification methods include polymerase chain reaction (PCR), the ligase chain reaction (LCR), the transcription-based amplification system (TAS), the self-sustained sequence replication system (3SR). A wide variety of cloning methods, host cells, and in vitro amplification methodologies are well known to persons of skill.

In a preferred embodiment, immunoconjugates are prepared by inserting the cDNA which encodes an anti-CD30 or CD30 stalk scFv antibody into a vector which comprises the cDNA encoding the EM. The insertion is made so that the scFv and the EM are read in frame, that is in one continuous polypeptide which contains a functional Fv region and a functional EM region. In a particularly preferred embodiment, cDNA encoding a cytotoxin is ligated to a scFv so that the cytotoxin is located at the carboxyl terminus of the scFv. In a most preferred embodiment, cDNA encoding a *Pseudomonas* exotoxin ("PE"), mutated to eliminate or to reduce non-specific binding, is ligated to a scFv so that the toxin is located at the amino terminus of the scFv.

Once the nucleic acids encoding an EM, anti-CD30 or CD30 stalk antibody, or an immunoconjugate of the present invention are isolated and cloned, one may express the desired protein in a recombinantly engineered cell such as bacteria, plant, yeast, insect and mammalian cells as discussed above in connection with the discussion of expression vectors encoding CD30 or CD30 stalk. It is expected that those of skill in the art are knowledgeable in the numerous expression systems available for expression of proteins including *E. coli*, other bacterial hosts, yeast, and various higher eukaryotic cells such as the COS, CHO, HeLa and myeloma cell lines. No attempt to describe in detail the various methods known for the expression of proteins in prokaryotes or eukaryotes will be made.

One of skill would recognize that modifications can be made to a nucleic acid encoding a polypeptide of the present invention (i.e., anti-CD30 or CD30 stalk antibody, PE, or an immunoconjugate formed from their combination) without diminishing its biological activity. Some modifications may be made to facilitate the cloning, expression, or incorporation of the targeting molecule into a fusion protein. Such modifications are well known to those of skill in the art and include, for example, termination codons, a methionine added at the amino terminus to provide an initiation site, and additional amino acids placed on either terminus to create conveniently located restriction sites.

In addition to recombinant methods, the immunoconjugates, EM, and antibodies of the present invention can also be constructed in whole or in part using standard peptide synthesis. Solid phase synthesis of the polypeptides of the present invention of less than about 50 amino acids in length may be accomplished by attaching the C-terminal amino acid of the sequence to an insoluble support followed by sequential addition of the remaining amino acids in the sequence. Techniques for solid phase synthesis are described by Barany & Merrifield, THE PEPTIDES: ANALYSIS, SYNTHESIS, BIOLOGY. VOL. 2: SPECIAL METHODS IN P*EPTIDE* SYNTHESIS, PART A. pp. 3-284; Merrifield, et al. *J. Ant. Chem. Soc.* 85:2149-2156 (1963), and Stewart, et al., SOLID PHASE PEPTIDE SYNTHESIS, 2ND ED., Pierce Chem. Co., Rockford, Ill. (1984). Proteins of greater length may be synthesized by condensation of the amino and carboxyl termini of shorter fragments. Methods of forming peptide bonds by activation of a carboxyl terminal end (e.g., by the use of the coupling reagent N,N'-dicycylohexylcarbodiimide) are known to those of skill.

B. Purification

Once expressed, the recombinant immunoconjugates, antibodies, and/or effector molecules of the present invention can be purified according to standard procedures of the art, including ammonium sulfate precipitation, affinity columns, column chromatography, and the like (see, generally, R. Scopes, PROTEIN PURIFICATION, Springer-Verlag, N.Y. (1982)). Substantially pure compositions of at least about 90 to 95% homogeneity are preferred, and 98 to 99% or more homogeneity are most preferred for pharmaceutical: uses. Once purified, partially or to homogeneity as desired, if to be used therapeutically, the polypeptides should be substantially free of endotoxin.

Methods for expression of single chain antibodies and/or refolding to an appropriate active form, including single chain antibodies, from bacteria such as *E. coli* have been described are well-known and are applicable to the antibodies of this invention. See, Buchner, et al., *Anal. Biochem.* 205:263-270 (1992); Pluckthun, *Biotechnology* 9:545 (1991); Huse, et al., *Science* 246:1275 (1989) and Ward, et al., *Nature* 341:544 (1989), all incorporated by reference herein.

Often, functional heterologous proteins from *E. coli* or other bacteria are isolated from inclusion bodies and require solubilization using strong denaturants, and subsequent refolding. During the solubilization step, as is well-known in the art, a reducing agent must be present to separate disulfide bonds. An exemplary buffer with a reducing agent is: 0.1 M Tris pH 8, 6 M guanidine, 2 mM EDTA, 0.3 M DTE (dithioerythritol). Reoxidation of the disulfide bonds can occur in the presence of low molecular weight thiol reagents in reduced and oxidized form, as described in Saxena, et al., *Biochemistry* 9: 5015-5021 (1970), incorporated by reference herein, and especially as described by Buchner, et al., supra.

Renaturation is typically accomplished by dilution (e.g., 100-fold) of the denatured and reduced protein into refolding buffer. An exemplary buffer is 0.1 M Tris, pH 8.0, 0.5 M L-arginine, 8 mM oxidized glutathione (GSSG), and 2 mM EDTA.

As a modification to the two chain antibody purification protocol, the heavy and light chain regions are separately solubilized and reduced and then combined in the refolding solution. A preferred yield is obtained when these two proteins are mixed in a molar ratio such that a 5 fold molar excess of one protein over the other is not exceeded. It is desirable to add excess oxidized glutathione or other oxidizing low molecular weight compounds to the refolding solution after the redox-shuffling is completed.

Toxins

A. Introduction

Toxins can be employed with antibodies of the present invention to yield chimeric molecules, such as immunotoxins. Exemplary toxins include ricin, abrin, diphtheria toxin and subunits thereof, ribotoxin, ribonuclease, saporin, and calicheamicin, as well as botulinum toxins A through F. These toxins are well known in the art and many are readily available from commercial sources (e.g., Sigma Chemical Company, St. Louis, Mo.). Diphtheria toxin is isolated from *Corynebacterium diphtheriae*. Typically, diphtheria toxin for use in immunotoxins is mutated to reduce or to eliminate non-specific toxicity. A mutant known as CRM107, which has full enzymatic activity but markedly reduced non-specific toxicity, has been known since the 1970's (Laird and Groman, J. Virol. 19: 220 (1976)), and has been used in human clinical trials. See, U.S. Pat. Nos. 5,792,458 and 5,208,021. As used herein, the term "diphtheria toxin" refers as appropriate to native diphtheria toxin or to diphtheria toxin that retains enzymatic activity but which has been modified to reduce non-specific toxicity.

Ricin is the lectin RCA60 from *Ricinus communis* (Castor bean). The term "ricin" also references toxic variants thereof. For example, see, U.S. Pat. Nos. 5,079,163 and 4,689,401. *Ricinus communis* agglutinin (RCA) occurs in two forms designated $RCA_{60}$ and $RCA_{120}$ according to their molecular weights of approximately 65 and 120 kD, respectively (Nicholson & Blaustein, *J. Biochim. Biophys. Acta* 266:543 (1972)). The A chain is responsible for inactivating protein synthesis and killing cells. The B chain binds ricin to cell-surface galactose residues and facilitates transport of the A chain into the cytosol (Olsnes, et al., *Nature* 249:627-631 (1974) and U.S. Pat. No. 3,060,165).

Conjugating ribonucleases to targeting molecules for use as immunotoxins is discussed in, e.g., Suzuki et al., Nat Biotech 17:265-70 (1999). Exemplary ribotoxins such as α-sarcin and restrictocin are discussed in, e.g., Rathore et al., Gene 190:31-5 (1997) and Goyal and Batra, Biochem 345 Pt 2:247-54 (2000). Calicheamicins were first isolated from *Micromonospora echinospora* and are members of the enediyne antitumor antibiotic family that cause double strand breaks in DNA that lead to apoptosis. See, e.g., Lee et al., J. Antibiot 42:1070-87 (1989). The drug is the toxic moiety of an immunotoxin in clinical trials. See, e.g., Gillespie et al., Ann Oncol 11:735-41 (2000).

Abrin includes toxic lectins from *Abrus precatorius*. The toxic principles, abrin a, b, c, and d, have a molecular weight of from about 63 and 67 kD and are composed of two disulfide-linked polypeptide chains A and B. The A chain inhibits protein synthesis; the B-chain (abrin-b) binds to D-galactose residues (see, Funatsu, et al., *Agr. Biol. Chem.* 52:1095 (1988); and Olsnes, *Methods Enzymol.* 50:330-335 (1978)).

In preferred embodiments of the present invention, the toxin is *Pseudomonas* exotoxin (PE). Native *Pseudomonas* exotoxin A ("PE") is an extremely active monomeric protein (molecular weight 66 kD), secreted by *Pseudomonas aeruginosa*, which inhibits protein synthesis in eukaryotic cells. The native PE sequence is provided in commonly assigned U.S. Pat. No. 5,602,095, incorporated herein by reference. The method of action is inactivation of the ADP-ribosylation of elongation factor 2 (EF-2). The exotoxin contains three structural domains that act in concert to cause cytotoxicity. Domain Ia (amino acids 1-252) mediates cell binding. Domain II (amino acids 253-364) is responsible for translocation into the cytosol and domain III (amino acids 400-613) mediates ADP ribosylation of elongation factor 2. The function of domain Ib (amino acids 365-399) remains undefined, although a large part of it, amino acids 365-380, can be deleted without loss of cytotoxicity. See Siegall, et al., *J. Biol. Chem.* 264:14256-14261 (1989).

The term "*Pseudomonas* exotoxin" ("PE") as used herein refers as appropriate to a full-length native (naturally occurring) PE or to a PE that has been modified. Such modifications may include, but are not limited to, elimination of domain Ia, various amino acid deletions in domains Ib, II and III, single amino acid substitutions and the addition of one or more sequences at the carboxyl terminus, such as KDEL (SEQ ID NO:30) and REDL (SEQ ID NO:31). See Siegall, et al., supra. In a preferred embodiment, the cytotoxic fragment of PE retains at least 50%, preferably 75%, more preferably at least 90%, and most preferably 95% of the cytotoxicity of native PE. In a particularly preferred embodiment, the cytotoxic fragment is more toxic than native PE.

PE employed in the present invention include the native sequence, cytotoxic fragments of the native sequence, and conservatively modified variants of native PE and its cytotoxic fragments. Cytotoxic fragments of PE include those which are cytotoxic with or without subsequent proteolytic or other processing in the target cell (e.g., as a protein or preprotein). Cytotoxic fragments of PE known in the art include PE40, PE38, and PE35.

In preferred embodiments, the PE has been modified to reduce or eliminate non-specific cell binding, typically by deleting domain Ia, as taught in U.S. Pat. No. 4,892,827, although this can also be achieved, for example, by mutating certain residues of domain Ia. U.S. Pat. No. 5,512,658, for instance, discloses that a mutated PE in which Domain Ia is present but in which the basic residues of domain Ia at positions 57, 246, 247, and 249 are replaced with acidic residues (glutamic acid, or "E")) exhibits greatly diminished non-specific cytotoxicity. This mutant form of PE is sometimes referred to as PE4E.

PE40 is a truncated derivative of PE as previously described in the art. See, Pai, et al., *Proc. Nat'l Acad. Sci. USA* 88:3358-62 (1991); and Kondo, et al., *J. Biol. Chem.* 263: 9470-9475 (1988). PE35 is a 35 kD carboxyl-terminal fragment of PE in which amino acid residues 1-279 have deleted and the molecule commences with a met at position 280 followed by amino acids 281-364 and 381-613 of native PE. PE35 and PE40 are disclosed, for example, in U.S. Pat. Nos. 5,602,095 and 4,892,827.

In some preferred embodiments, the cytotoxic fragment PE38 is employed. PE38 is a truncated PE pro-protein composed of amino acids 253-364 and 381-613 which is activated to its cytotoxic form upon processing within a cell (see e.g., U.S. Pat. No. 5,608,039, and Pastan et al., Biochim. Biophys. Acta 1333:C1-C6 (1997)).

While in preferred embodiments, the PE is PE4E, PE40, or PE38, any form of PE in which non-specific cytotoxicity has been eliminated or reduced to levels in which significant toxicity to non-targeted cells does not occur can be used in the immunotoxins of the present invention so long as it remains capable of translocation and EF-2 ribosylation in a targeted cell.

B. Conservatively Modified Variants of PE

Conservatively modified variants of PE or cytotoxic fragments thereof have at least 80% sequence similarity, preferably at least 85% sequence similarity, more preferably at least 90% sequence similarity, and most preferably at least 95% sequence similarity at the amino acid level, with the PE of interest, such as PE38.

The term "conservatively modified variants" applies to both amino acid and nucleic acid sequences. With respect to particular nucleic acid sequences, conservatively modified variants refer to those nucleic acid sequences which encode identical or essentially identical amino acid sequences, or if the nucleic acid does not encode an amino acid sequence, to essentially identical nucleic acid sequences. Because of the degeneracy of the genetic code, a large number of functionally identical nucleic acids encode any given polypeptide. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid.

C. Assaying for Cytotoxicity of PE

*Pseudomonas* exotoxins employed in the invention can be assayed for the desired level of cytotoxicity by assays well known to those of skill in the art. Thus, cytotoxic fragments of PE and conservatively modified variants of such fragments can be readily assayed for cytotoxicity. A large number of candidate PE molecules can be assayed simultaneously for cytotoxicity by methods well known in the art. For example, subgroups of the candidate molecules can be assayed for cytotoxicity. Positively reacting subgroups of the candidate molecules can be continually subdivided and reassayed until the desired cytotoxic fragment(s) is identified. Such methods allow rapid screening of large numbers of cytotoxic fragments or conservative variants of PE.

Pharmaceutical Compositions

In another aspect, this invention provides compositions that comprise an immunoconjugate of the invention and a pharmaceutically acceptable carrier. The composition may comprise, for example, a chimeric molecule comprising a targeting molecule and a detector molecule to detect cells expressing CD30 or CD30 stalk. The compositions of this invention can be prepared in unit dosage forms for administration to a subject. The amount and timing of administration are at the discretion of the treating physician to achieve the desired purposes.

In an especially preferred group of embodiments, the compositions of the invention are antibody and/or immunoconjugate compositions of this invention (i.e., PE linked to an anti-CD30 or CD30 stalk antibody). These compositions are particularly suited for parenteral administration, such as intravenous administration.

The compositions for administration will commonly comprise a solution of the antibody and/or immunoconjugate dissolved in a pharmaceutically acceptable carrier, preferably an aqueous carrier. A variety of aqueous carriers can be used, e.g., buffered saline and the like. These solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of fusion protein in these formulations can vary widely, and will be selected primarily based on fluid volumes, viscosities, body weight and the like in accordance with the particular mode of administration selected and the patient's needs.

Thus, a typical pharmaceutical immunotoxin composition of the present invention for intravenous administration would be about 0.1 to 10 mg per patient per day. Dosages from 0.1 up to about 100 mg per patient per day may be used, particularly if the drug is administered to a secluded site and not into the circulatory or lymph system, such as into a body cavity or into a lumen of an organ. Actual methods for preparing administrable compositions will be known or apparent to those skilled in the art and are described in more detail in such publications as REMINGTON'S PHARMACEUTICAL SCIENCE, 19TH ED., Mack Publishing Company, Easton, Pa. (1995).

In another embodiment, intact anti-CD30 antibodies are administered to induce complement-dependent cytotoxicity of CD30+ cells. In this embodiment, the antibodies administered are preferably T420, T427, T405, and T408. Conveniently, antibodies may be provided in lyophilized form and rehydrated with sterile water before administration, although they are also provided in sterile solutions of known concentration. The antibody solution is then added to an infusion bag containing 0.9% Sodium Chloride, USP, and typically administered at a dosage of from 0.5 to 15 mg/kg of body weight. Considerable experience is available in the art in the administration of antibody drugs, which have been marketed in the U.S. since the approval of Rituxan® in 1997. Antibody drugs are desirably administered by slow infusion, rather than in an IV push or bolus. Typically, a higher loading dose is administered, with subsequent, maintenance doses being administered at a lower level. For example, an initial loading dose of 4 mg/kg may be infused over a period of some 90 minutes, followed by weekly maintenance doses for 4-8 weeks of 2 mg/kg infused over a 30 minute period if the previous dose was well tolerated.

The compositions of the present invention can be administered to slow or inhibit the growth of cells of CD30-expressing cancers. In these applications, compositions are administered to a patient suffering from a disease, in an amount sufficient to inhibit growth of CD30-expressing cells. An amount adequate to accomplish this is defined as a "therapeutically effective dose." Amounts effective for this use will depend upon the severity of the disease and the general state of the patient's health. An effective amount of the compound is that which provides either subjective relief of a symptom(s) or an objectively identifiable improvement as noted by the clinician or other qualified observer.

Single or multiple administrations of the compositions are administered depending on the dosage and frequency as required and tolerated by the patient. In any event, the composition should provide a sufficient quantity of the immunotoxins or antibodies of this invention to effectively treat the patient. Preferably, the dosage is administered once but may be applied periodically until either a therapeutic result is achieved or until side effects warrant discontinuation of therapy. Generally, the dose is sufficient to treat or ameliorate symptoms or signs of disease without producing unacceptable toxicity to the patient.

Controlled release parenteral formulations of the immunoconjugate compositions of the present invention can be made as implants, oily injections, or as particulate systems. For a broad overview of protein delivery systems see, Banga, A. J., THERAPEUTIC PEPTIDES AND PROTEINS: FORMULATION, PROCESSING, AND DELIVERY SYSTEMS, Technomic Publishing Company, Inc., Lancaster, Pa., (1995) incorporated herein by reference. Particulate systems include microspheres, microparticles, microcapsules, nanocapsules, nanospheres, and nanoparticles. Microcapsules contain the therapeutic protein, such as a cytotoxin or a drug, as a central core. In microspheres the therapeutic is dispersed throughout the particle., Particles, microspheres, and microcapsules smaller than about 1 μm are generally referred to as nanoparticles, nanospheres, and nanocapsules, respectively. Capillaries have a diameter of approximately 5 μm so that only nanoparticles are administered intravenously. Microparticles are typically around 100 μm in diameter and are administered subcutaneously or intramuscularly. See, e.g., Kreuter, J., COLLOIDAL DRUG DELIVERY SYSTEMS, J. Kreuter, ed., Marcel Delver, Inc., New York, N.Y., pp. 219-342 (1994); and Tice & Tabibi, TREATISE ON CONTROLLED DRUG DELIVERY, A. Kydonieus, ed., Marcel Dekker, Inc. New York, N.Y., pp. 315-339, (1992) both of which are incorporated herein by reference.

Polymers can be used for ion-controlled release of immunoconjugate compositions of the present invention. Various degradable and nondegradable polymeric matrices for use in controlled drug delivery are known in the art (Langer, R., Accounts Chem. Res. 26:537-542 (1993)). For example, the block copolymer, polaxamer 407, exists as a viscous yet mobile liquid at low temperatures but forms a semisolid gel at body temperature. It has shown to be an effective vehicle for formulation and sustained delivery of recombinant interleukin-2 and urease (Johnston, et al., Pharm. Res. 9:425-434 (1992); and Pec, et al., J. Parent. Sci. Tech. 44(2):58-65 (1990)). Alternatively, hydroxyapatite has been used as a microcarrier for controlled release of proteins (Ijntema, et al., Int. J. Pharm. 112:215-224 (1994)). In yet another aspect, liposomes are used for controlled release as well as drug targeting of the lipid-capsulated drug (Betageri, et al., LIPOSOME DRUG DELIVERY SYSTEMS, Technomic Publishing Co., Inc., Lancaster, Pa. (1993)). Numerous additional systems for controlled delivery of therapeutic proteins are known. See, e.g., U.S. Pat. Nos. 5,055,303, 5,188,837, 4,235,871, 4,501,728, 4,837,028 4,957,735 and 5,019,369, 5,055,303; 5,514,670; 5,413,797; 5,268,164; 5,004,697; 4,902,505; 5,506,206, 5,271,961; 5,254,342 and 5,534,496, each of which is incorporated herein by reference.

Among various uses of the immunotoxins and antibodies of the present invention are included a variety of disease conditions caused by specific human cells that may be eliminated by the toxic action of the fusion protein. One preferred application for the immunotoxins and antibodies of the invention is the treatment of malignant cells expressing CD30.

Diagnostic Kits and in Vitro Uses

In another embodiment, this invention provides for kits for the detection of CD30 or an immunoreactive fragment thereof, (i.e., collectively, a "CD30 protein") in a biologcal sample. A "biological sample" as used herein is a sample of biological tissue or fluid that contains CD30. Such samples include, but are not limited to, tissue from biopsy, blood, and blood cells (e.g., white cells). Preferably, the cells are lymphocytes. Biological samples also include sections of tissues, such as frozen sections taken for histological purposes. A biological sample is typically obtained from a multicellular eukaryote, preferably a mammal such as rat, mouse, cow, dog, guinea pig, or rabbit, and more preferably a primate, such as a macaque, chimpanzee, or human. Most preferably, the sample is from a human.

Kits will typically comprise an anti-CD30 antibody of the present invention. In some embodiments, the anti-CD30 antibody will be an anti-CD30 Fv fragment, such as a scFv or dsFv fragment, although intact antibodies may be used for some purposes.

In addition the kits will typically include instructional materials disclosing means of use of an antibody of the present invention (e.g. for detection of mesothelial cells in a sample). The kits may also include additional components to facilitate the particular application for which the kit is designed. Thus, for example, the kit may additionally contain means of detecting the label (e.g. enzyme substrates for enzymatic labels, filter sets to detect fluorescent labels, appropriate secondary labels such as a sheep anti-mouse-HRP, or the like). The kits may additionally include buffers and other reagents routinely used for the practice of a particular method. Such kits and appropriate contents are well known to those of skill in the art.

In one embodiment of the present invention, the diagnostic kit comprises an immunoassay. As described above, although the details of the immunoassays of the present invention may vary with the particular format employed, the method of detecting CD30 in a biological sample generally comprises the steps of contacting the biological sample with an antibody of the present invention which specifically reacts, under immunologically reactive conditions, to CD30. The antibody is allowed to bind to CD30 under immunologically reactive conditions, and the presence of the bound antibody is detected directly or indirectly.

Due to the increased affinity of the antibodies of the invention, the antibodies will be especially useful as diagnostic agents and in in vitro assays to detect the presence of CD30 in biological samples. For example, the antibodies taught herein can be used as the targeting moieties of immunoconjugates in immunohistochemical assays to determine whether a sample contains cells expressing CD30. Detection of CD30 in lymphocytes would indicate either that the patient has a cancer characterized by the presence of CD30-expressing cells, or that a treatment for such a cancer has not yet been successful at eradicating the cancer.

In another set of uses for the invention, immunotoxins targeted by antibodies' of the invention can be used to purge targeted cells from a population of cells in a culture. Thus, for example, cells cultured from a patient having a cancer expressing CD30 can be purged of cancer cells by contacting the culture with immunotoxins which use the antibodies of the invention as a targeting moiety.

Detectable Labels

Antibodies of the present invention may optionally be covalently or non-covalently linked to a detectable label. Detectable labels suitable for such use include any composition detectable by spectroscopic, photochemical, biochemical, immunochemical, electrical, optical or chemical means. Useful labels in the present invention include magnetic beads (e.g. DYNABEADS), fluorescent dyes (e.g., fluorescein isothiocyanate, Texas red, rhodamine, green fluorescent protein, and the like), radiolabels (e.g., $^3H$, $^{125}I$, $^{35}S$, $^{14}C$, or $^{32}P$), enzymes (e.g., horse radish peroxidase, alkaline phosphatase and others commonly used in an ELISA), and calorimetric labels such as colloidal gold or colored glass or plastic (e.g. polystyrene, polypropylene, latex, etc.) beads.

Means of detecting such labels are well known to those of skill in the art. Thus, for example, radiolabels may be detected using photographic film or scintillation counters, fluorescent markers may be detected using a photodetector to detect emitted illumination. Enzymatic labels are typically detected by providing the enzyme with a substrate and detecting the reaction product produced by the action of the enzyme on the substrate, and colorimetric labels are detected by simply visualizing the colored label.

EXAMPLES

The following examples are offered to illustrate, but not to limit the claimed invention.

Example 1

This Example sets forth the materials and methods used in the studies reported in the next Example.

Cells. All cells were cultured in Iscove's modified Dulbeccos' medium (GIBCO BRL, Gaithersburg, Md.) supplemented with 10% fetal bovine serum (FBS); 13 human cell lines were used in the studies reported in Example 2. A431-CD30 (Rozemuller et al., *Int. J. Cancer*, 92:861-870 (2001) ("Rozemuller 2001")) and ATac-4 cells (Kreitman et al., *Blood*, 83:426-434 (1994)) are stable transformants of A431 cells that express CD30 and CD25 on the cell surface, respectively. L540, L428, L591 (from Dr. C. S. Duckett, NIH) and KM-H2 (from Dr. C. S. Duckett, NIH) were cell lines established from HL. KARPAS-299, SR-786, SUDHL-1, and SUP-M2 were ALCL-derived cell lines available from the German Collection of Microorganisms and Cell Cultures (DSMZ, Braunschweig, Germany). HUT102W and SIT are HTLV-1-positive adult T-cell leukemia cell lines (from Dr. N. Alima, Kagoshima University, Japan). DEL (from DSMZ) cells were originated from malignant histocytosis.

Recombinant CD30s. Recombinant soluble CD30 (sCD30) was produced in *E. coli* BL21($\lambda$DE3) containing pHR30HNB, a plasmid encoding the extracellular domain of human CD30 with His-tag at the C-terminus, as described previously (Rozemuller 2001).

The extracellular domain of CD30 was expressed as a fusion protein with human IgG Fc in transfected 293T cells. The DNA fragment encoding human IgG Fc was amplified by PCR using a Ret-Fc plasmid (provided by Dr. M. Billaud, CNRS, France) as the template and inserted between NotI and XbaI sites of pCDNA1.1 (Stratagene, La Jolla, Calif.). The cDNA for the extracellular domain of CD30 containing its signal peptide (Rozemuller 2001) was inserted between the NotI and EcoRI to obtain the plasmid pRB-2k1-CD30. The plasmid was transfected into 293T cells by lipofectamine reagent (Life Technologies, Rockville, Md.), and the CD30-Fc protein harvested from the culture supernatant and purified with Hi-Trap protein A column (Amersham Pharmacia Biotech, Piscataway, N.J.).

Production of Anti-CD30 MAbs. Female Balb/c mice (6 weeks old) were immunized intradermally twice with 15 μg of pHRm30c, a plasmid encoding full-length of human CD30 under control of cytomegalovirus promoter (Rozemuller 2001; Chowdhury et al., *Proc. Natl. Acad. Sc. U.S.A.*, 95:669-674 (1998)). The DNA immunizations were followed by three or four i.v. injections of 50 μg of sCD30 protein with two weeks intervals. Three days after the last boost, spleen cells were taken and fused with SP2/O mouse myeloma cells as described (Nagata et al., *Hybridoma*, 10:369-378 (1991)). Culture supernatants of growing hybridomas were tested for the production of anti-CD30 MAbs by an enzyme-linked immunosorbent assay (ELISA) described below. Cloning of the specific hybridomas, MAb purification from the culture supernatants and biotinylation of purified MAb were performed as described (Nagata et al., *Arch. Virol.*, 127:153-168 (1992)). Isotype of the MAbs was determined by a mouse MAb isotyping kit (Zymed, South San Francisco, Calif.).

Immunoglobulin concentrations in the culture supernatants were determined by a sandwich ELISA as described previously (Nagata et al., *Hybridoma*, 10:369-378 (1991)). The HeFi-I hybridoma producing anti-CD30 MAb (Hecht et al., *J. Immunol.*, 134: 4231-4236 (1985)) was obtained from the National Cancer Institute, Frederick Cancer Research and Development Center, Biological Resources Branch, Frederick, Md.

Cloning of VH and VL of MAbs. Total cellular RNA was isolated from $10^7$ hybridoma cells using a RNA extraction kit (Amersham Pharmacia Biotech, Uppsala, Sweden). VH and VL cDNAs of the MAbs were obtained by a rapid amplification of cDNA ends (RACE) method using SMART RACE cDNA amplification kit (Clontech, Palo Alto, Calif.). In brief, adaptor-ligated cDNA was generated from 5 μg of the RNA using Superscript II reverse transcriptase (GIBCO BRL) with 10 μmol of 3' end primers designed for each chain of Ig (κ, γ1, γ2b) to anneal each constant region sequence (GACTGAG-GCACCTCCAGATGTTAA (SEQ ID NO:32) for κ, CAGGGTCACCATGGAGTTAGTTTG (SEQ ID NO:33) for γ1, and TCCAGAGTTCCAAGTCACAGTCAC (SEQ ID NO:34) for γ2b chain). The primers covered the all of the constant region sequences registered in the Kabat database (available online by entering "http://" followed by "immuno.bme.nwu.edu/") (Johnson, G. and Wu, T. T, *Nucleic Acids Res.*, 29: 205-206 (2001)). The prepared cDNAs were used as the template for PCR reactions between 5' end primer that binds to the adaptor sequence and Ig subclass-specific 3' end primer whose sequences is located on the upstream of the primers for cDNA synthesis (GGATGGTGGGAAGATG-GATACAGTTGGTGCAGC (SEQ ID NO:35) for κ, AGGGGCCAGTGGATAGACAGATGGGGGTGT (SEQ ID NO:36) for γ1, and AGGGGCCAGTGGATAGACT-GATGGGGGTGT (SEQ ID NO:37) for γ2b chain). The PCR products were cloned into pCR2.1-TOPO vector using TOPO TA cloning kit (Invitorogen, San Diego, Calif.). At least 3 independent clones for each chain were sequenced to exclude the possibility of PCR error. The obtained sequences were aligned according to the Kabat alignment scheme (Kabat et al., Sequences of Proteins of Immunological Interest, 5th ed. U.S. Department of Health and Human Services, Public Health Service, National Institute of Health (1991)); see also Kabat database, supra.

Construction of Plasmids for dsFv-PE38 Immunotoxins. Two plasmids were constructed for each dsFv-immunotoxin: one encoded a $V_L$ chain with a cysteine mutation at residue 100 (according to the Kabat numbering) and the other encoded a $V_H$ chain-PE38 fusion protein with a cysteine mutation at position 44 of the $V_H$ (Reiter et al., *Nat. Biotechnol.*, 14:1239-1245 (1996)). To make the $V_L$ construct, each $V_L$ was PCR-amplified using a 5' primer, introducing an Nde I site and a 3' primer, introducing an EcoRI site and mutating residue 100 to cysteine. $V_H$ fragments containing cysteine mutation at residue 44 were made by a splicing overlap extension PCR method (Ho et al., *Gene*, 77:51-59 (1989)). Both strands of oligo DNA around residue 44 were synthesized to introduce cysteine at this position. 5' and 3' end primers were designed to introduce an Nde I site containing an ATG initiation codon and a Hind III site that code an additional lysine or glutamine, respectively. Two truncated VH fragments were amplified using one of the two oligos containing the mutation with the 5' or 3' terminal primer. These two fragments were combined in a subsequent assembly reaction in which the overlapped ends of each fragment anneal ad extend. The final full-length DNA of $V_H$ was amplified by another PCR using the 5' and 3' end primers. The $V_L$(Cys) and $V_H$(Cys) PCR products were digested with Nde I and either EcoRI or Hind III and were cloned into a T7 based expression vector pRB98 Amp (originated from pULI7, Brinkmann et al., *Proc. Natl. Acad. Sci. USA.*, 88:8616-8620 (1991)) that encodes the connector and PE38 between Hind III and EcoRI sites. The correct construction of the plasmids was confirmed by DNA sequencing.

Production and Purification of Recombinant dsFv-immunotoxins. Disulfide-linked immunotoxins were produced by refolding of inclusion body protein as described previously (Brinkmann et al., *Proc. Natl. Acad. Sci. U.S.A.*, 90:7538-7542 (1993); Buchner et al., *J Anal. Biochem.*, 205:263-270 (1992)). The plasmids encoding VL(Cys) and VH(Cys)-PE38 were separately transfected into *E. coli* BL21 (λDE3). The bacterial cultures were induced for the protein expression in the exponential growth phase with 1 mM IPTG for 2 h. The recombinant proteins accumulated as insoluble inclusion bodies and were isolated from lysed bacteria cells by centrifugation. These inclusion bodies contained the recombinant protein in over 70% purity, but in an inactive form that requires refolding to an active form. The inclusion bodies were completely solubilized in 6M guanidine hydrochloride, and then reduced with dithioerythritol. The solubilized reduced proteins of VL(Cys) and VH(Cys)-PE38 were combined in an 2:1 molar ratio and refolded by 1:100 dilution into refolding solution containing redox shuffling and aggregation-preventing additives (oxidized and reduced glutathione, and L-arginine). After the refolding, guanidine hydrochloride in the solution was removed by a dialysis against a Tris buffer containing 0.1 M urea. The refolded active protein was then separated from contaminating bacterial proteins and from improperly folded protein by anion exchange chromatography using Q-Sepharose and Mono-Q (Amersham Pharmacia Biotech) and by size exclusion chromatography (TSK3000, TOSOH, Japan). The proteins were analyzed by sodium dodecyl sulfate polyacrylamide gel electrophoresis (SDS-PAGE) under reducing and non-reducing conditions. Protein concentrations of the purified immunotoxins were determined by a Bradford assay (Coomassie Plus; Pierce, Rockford, Ill.) with bovine serum albumin as the standard.

ELISA. The binding of anti-CD30 MAbs to sCD30 and CD30-Fc was assayed by indirect ELISAs. Microtiter plates (Costar, Cambridge, Mass.) were coated with 20 ng/well of sCD30 or CD30-Fc in PBS overnight at 4° C. After blocking with 0.5% of BSA in PBS, hybridoma supernatants or purified MAbs were added to the coated wells and incubated for 2 h at room temperature. The bound MAbs were detected with alkaline phosphatase (ALP)-labeled anti-mouse IgG (BioSource, Camarillo, Calif.) and p-nitrophenyl phosphate as the substrate.

FACS Analysis. FACS analysis was performed to measure the binding of the MAbs or immunotoxins to native CD30 expressed on various cell lines. In a typical protocol for staining with MAb, $2 \times 10^5$ cells were incubated with appropriate dilution of the MAbs in 100 μl of PBS containing 5% FBS and 0.1% sodium azide. After incubation for 1 h at 4° C., the cells were washed twice with the same buffer and incubated with FITC-labeled goat mouse IgG (BioSource). After washing, the cells were suspended in 1 ml of the buffer, and the fluorescence associated with the live cells was measured using a FACS Calibur flow cytometer (Beckman Coulter, Fullerton, Calif.). For controls, anti-CD30 MAbs HeFi-I, Ber-H2 (DAKO, Glostrup, Denmark) and HRS-4 (Biodesign Int., Kennbunk, Me.) were used.

For cell staining using immunotoxins, an anti-PE rabbit polyclonal antibody (our laboratory) and R-phycoerythrin-labeled anti-rabbit IgG (BioSource) were used as the detection reagents.

A competitive FACS assay was carried out to classify the epitopes recognized by the anti-CD30 MAbs. The CD30-positive cells were incubated with 50 ng/ml of various biotinylated MAbs in the presence of serial dilution of various unlabeled MAbs. R-phycoerythrin-conjugated streptavidin (Jackson, West Grove, Pa.) was used for the detection of the biotinylated MAbs bound to cells.

Surface Plasmon Resonance Assay. The affinity of the dsFv immunotoxins to sCD30 was determined by surface plasmon resonance using BIAcore (Biacore, Piscataway, N.J.). An appropriate amount (500 resonance units) of sCD30 was immobilized onto the biosensor chip, CM5 (Biacore). On and off rates of immunotoxins were measured in PBS by injecting 25 µg/ml of each immunotoxin over the chip surface for 5 minutes and then allowing the bound material to dissociate for 5 minutes by flowing only the buffer solution over the chip. Binding kinetics was analyzed using BIAevaluation 2.1 software.

Cytotoxicity Assay. Cytotoxic activities were assayed by the inhibition of cellular protein synthesis measured by $^3$H-leucine uptake by the cells (Rozemuller et al., Int. J. Cancer, 92:861-870 (2001)). Cells were seeded into 96-well plates at a concentration of $2.0 \times 10^4$ of cells/well and incubated for 24 h (attached cells) or 1 h (suspension cells). The immunotoxins diluted in the culture medium were added to the cells, resulting in final concentrations ranging from 0.01 to 1000 ng/ml. In some experiments, MAbs were added together with the immunotoxin as the competitors. As positive controls, anti-Tac(dsFv)-PE38 (Reiter et al., Int. J. Cancer, 58:142-149 (1994)) and anti-TFR(Fv)-PE40 (Batra et al., Mol. Cell Biol., 11:2200-2205 (1991)) were used. After incubation for 24 h, 2 µCi of $^3$H-leucine (Amersham Pharmacia Biotech) was added per well and incubated for 2-5 h. The cells were then frozen and thawed and harvested onto glass filters using a cell harvester (Tomtec, Hamden, Conn.). The radioactivity associated with the cells was determined in an automated scintillation counter (1205 Betaplate, Wallac, Gaithersburg, Md.).

Example 2

This Example reports the results of studies conducted using antibodies developed using the materials and methods of Example 1.

Production of Anti-CD30 MAbs. It has previously been reported that immunization of different strains of mice with a full-length human CD30 cDNA under the control of cytomegalovirus promoter induced extremely high anti-serum titers to the extracellular domain of CD30 ($>10^6$ by ELISA) (Rozemuller 2001). In this study, DNA-immunization was followed by 3-4 additional injections of recombinant sCD30 protein produced in E. coli (the extracellular domain of CD30 with His-tag on its C-terminus). Mice showing a good response to the protein boost reflected in the anti-CD30 serum titer were used for the production of MAbs. Three cell fusion experiments yielded a total or 6 specific hybridomas that secreted anti-CD30 MAbs in the culture medium. All of the MAbs reacted to sCD30 or CD30-Fc coated on plates by ELISA.

Characterization of Anti-CD30 MAbs. The characteristics of the six MAbs are summarized in Table 1. Six antibodies were obtained: five IgG1 and one IgG2b. In ELISA, all of the MAbs showed almost the same level of reactivity to sCD30 and CD30-Fc compared to the control MAbs (HeFi-I, Ber-H2 and HRS-4). The binding activity of the MAbs to native CD30 on cells was measured. A FACS analysis showed that all MAbs bound to native CD30 expressed on two CD30-positive HL cell lines, L428 and L540, with apparent affinities ranging 28-180% of the control (HeFi-I).

These MAbs were further characterized for their topographical epitopes by a competitive binding assay using FACS analysis. Three previously known anti-CD30 MAb (HeFi-I, HRS4 and Ber-H2) were included in this assay as controls. Some of the MAbs were biotinylated as the indicators and incubated with L540 cells in the presence of various concentrations of unlabeled MAbs as the competitors. The binding of all the biotinylated MAbs was competed by unlabeled homologous MAb in a dose-dependent manner. Also, inhibitory effects of heterologous MAbs were seen in some combinations with the biotinylated MAbs. The data of the inhibitory effects of 50-fold excess amounts of unlabeled MAbs are summarized in Table 2.

The epitopes of the anti-CD30 MAbs could be classified into two groups (I and II). Group I comprises Ber-H2, HRS-4, T6, T13, T14 and T21. All of the MAbs in this group inhibited the binding of biotinylated T14, suggesting that their epitopes are spatially close to each other to make a cluster. Also, none of the MAbs of group I inhibited the binding of group II MAbs, indicating that the epitopes of group I MAbs were separated from those of group II MAbs. Two MAbs of group I (T14 and T21) did not inhibit the binding of biotinylated HRS-4 and T6, whereas the rest of the group I MAbs (Ber-H2, HRS-4, T6 and T13) did. From these results, group I could be divided into two subgroups (I-a and I-b). The epitopes of the rest of the MAbs (HeFi-I, T24 and T25) were of group II since T24 MAb inhibited the binding of all the biotinylated MAbs assigned in this group. HeFi-I and T25 MAbs showed no inhibition on the binding of any heterologous MAbs in group II, suggesting that the location of the epitopes of these MAbs are not exactly the same as that of T24. Group II, therefore, was divided into three subgroups (II-a, II-b and II-c).

Cloning of cDNAs of the VH and VL Domain of the Anti-CD30 MAbs. We attempted to clone all Fvs of the MAbs to construct recombinant immunotoxins. VH and VL cDNAs were isolated from the hybridomas by a RACE method as described in Example I. All variable domains were cloned except VH of T21. The deduced amino acid sequences of VH and VL are shown in FIG. 2. One set of unique VH and VL cDNAs was obtained from each hybridoma except for T14; two VLs were isolated from T14. These sequences were different from those of the previous anti-CD30 Fvs reported. An aberrant VL sequence derived from SP2/O myeloma cells (Carroll et al., Mol. Immunol., 25:991-995 (1988)) was obtained from hybridomas T13 and T14. Sequence analysis using the database of germ line genes (Ig blast, found online by entering "http://www." followed by "ncbi.nlm.nih.gov/igblast/") revealed that all VH and VL amino acids sequences were derived from different germ line V genes with a similarity of 83-98%.

Production of Anti-CD30 dsFv-based Immunotoxins. The disulfide-linked immunotoxins consist of VH-PE38 and VL chains that are covalently linked during renaturation through a single key residue in each chain that has been mutated to cysteine. Based on predictions using molecular model and empirical data with other dsFv recombinant immunotoxins (Reiter et al., Nat. Biotechnol., 14:1239-1245 (1996); Brinkmann et al., Proc. Natl. Acad. Sci. U.S.A, 90:7538-7542 (1993); Reiter et al., J. Biol. Chem., 269:18327-18331 (1994); Reiter et al., Int. J. Cancer, 67:113-123 (1996)), one amino acid was chosen in each chain to mutate to cysteine. These are residue 44 of the VH and residue 100 of the VL (as numbered according to Kabat).

The VL(Cys) and VH(Cys)-PE38 were expressed in E. coli under control of the T7 promoter and harvested as inclusion bodies. The immunotoxins were refolded and purified as described in Example 1. The recovery of the inclusion body protein and purified immunotoxin protein are shown in Table 3. Four immunotoxins were obtained, based on Fvs of T6, T14-A (using T14-VL-A), T24 and T25. Upon SDS-PAGE, all immunotoxins migrated as single bands with the expected molecular weight (63 kDa) in a non-reducing gel. Under reducing conditions, each band separated into two bands, which correspond to VL and VH-PE38. This indicates that all dsFv immunotoxins were properly formed.

Specific Binding of the Anti-CD30 dsFv-immunotoxins to CD30 Molecules. The specific binding of the dsFv immunotoxins to CD30 on the cell surface was determined by FACS analysis. L540 cells expressing CD30 were stained by T6, T14-A, T24 and T25 dsFv-PE38 in a dose dependent manner, whereas no binding was detected on CD30-negative control cells, SP2/O. The relative reactivities estimated by the staining levels varied. T6 and T25 were the strongest binders. T74 and T14-A showed moderate and low levels of binding, respectively. In the same experiment, an immunotoxin reacting with the tranferrin receptor (HB21 (scFv)-PE40) used as a positive control, bound to the cells, and a negative control, anti-mesothelin SS1(dsFv)-PE38, did not. The binding of the anti-CD30 immunotoxins was inhibited by the addition of free CD30-Fc to the reaction, but the binding of the anti-transferrin immunotoxin was not affected. These results indicate that the Fv portions of the four different anti-CD30 dsFv-PE38s specifically bind to CD30 molecules on the target cells, with a variety of affinities.

The binding characteristics of the immunotoxins were analyzed by surface plasmon resonance using BIAcore. Table 4 shows the binding parameters determined from the sensorgrams of each immunotoxin where sCD30 was immobilized on the sensor chip. All anti-CD30 dsFv immunotoxins exhibited significant affinities to CD30, which varied vera 100-fold range. T6(dsFv)-PE38 and T25(dsv)-PE38 exhibited stronger binding than the others, with Kds of 22 nM and 4 nM, respectively. The affinity of T25(dsFv)-PE38 was comparable to that of the bivalent HeFi-I MAb and about 10-fold better than that of CL2(scFv)-PE38.

Cytotoxicity of the Anti-CD30 dsFv-immunotoxins. We initially evaluated the specific cytotoxicity of the anti-CD30 dsFv-immunotoxins using A431 cells stably transfected with a CD30 expressing plasmid. T6 and T25(dsFv)-PE38 specifically killed the CD30-expressing A431 cells with $IC_{50}$ values of 0.5 and 0.3 ng/ml, respectively. These two immunotoxins were more effective than CR2(scFv)-PE38 ($IC_{50}$=2.5 ng/ml). T24(dsFv)-PE38 was slightly cytotoxic ($IC_{50}$=20 ng/ml) and T14-A(dsFv)-PE38 was non-toxic. None of the anti-CD30 immunotoxins exhibited cytotoxicity to the control cells (ATAC4), which express CD25. Both the A431/CD30 and the A431/CD25 cells can be killed by a positive control immunotoxin, HB21(scFv)-PE40, to the same extent, suggesting these cells have similar susceptibilities to PE.

Effect of the Immunotoxins on a Panel of Cancer Cells. The effects of the anti-CD30 immunotoxins on various human CD30-positive cell lines from several different sources, which included Hodgkin's disease, ALCL, adult T-cell leukemia and others were examined. The expression level of CD30 on these cells was roughly estimated by a FACS analysis to see their relationship with the susceptibility to anti-CD30 immunotoxins. As shown in Table 5, the immunotoxins were effective on almost all the CD30-positive cell lines. The $IC_{50}$s varied over a 100-fold range depending on the cells and the immunotoxins. There was almost no correlation between the $IC_{50}$ values and the expression level of CD30 on the cells. On some cell lines, the $IC_{50}$s of T6 and T25(dsFv)-PE38 were 10 ng/ml or less, which is comparable to the activities of other dsFv-immunotoxins established for clinical use.

The specificity of the cytotoxicity of the T6 and T25 immunotoxins was confirmed by a competition assay using the original MAbs. Because the epitopes of T6 and T25 were topographically separated as shown in Table 2, both of the MAbs were used as the competitors. A431/CD30 and three cell lines that were susceptible to the immunotoxins were incubated with various concentrations of competitors and a concentration of T6 or T25 immunotoxin that was 3-fold higher than their $IC_{50}$s. On all the cells, the cytotoxicity, of the T6 and T25 immunotoxin was inhibited only by their parental MAb. This result shows that the immunotoxins retained the same binding specificity as the parent MAb and their cytotoxic activities on various CD30-positive cancer cells depends on their specific binding to the proper epitope.

Example 3

This Example discusses the results of the studies reported in Examples 1 and 2.

In this study, four anti-CD30 dsFv-based recombinant immunotoxins were produced whose Fvs originated from newly produced anti-CD30 MAbs. Two of the four immunotoxins showed particularly strong cytotoxic activity to CD30-positive cells. These two immunotoxins recognized two different epitopes on the CD30 molecule and both showed a relatively high affinity to CD30, suggesting that the affinity is an important factor in determining the efficacy of these anti-CD30 immunotoxins. Because these immunotoxins showed specific cytotoxicity against a wide range of CD30-positive cancer cell lines, they are expected to be useful agents for the treatment of CD30-positive hematologic malignancies.

Production and Characterization of Anti-CD30 MAbs. Various Fvs were isolated to test their suitability for making recombinant immunotoxins. In a previous study, specific scFvs for CD30 were isolated by panning scFv-displaying phage libraries made from the spleen cells of DNA-immunized mice (Rozemuller et al., *Int. J. Cancer*, 92:861-870 (2001)). This approach made it possible to obviate the burden of making specific hybridomas and of cloning of the Fv gene from the hybridoma. Unfortunately the number of different Fvs obtained by this method was limited. This was probably due to the protocol used for PCR amplification of Fv genes, which could have lead to a biased library. In addition, the selection and enrichment steps could affect the Fvs obtained. Thus, the hybridoma technique was used to obtain a variety of different Fvs.

The new anti-CD30 MAbs were characterized for their binding to cells expressing CD30 and for their topographical epitopes. Previously, we have concentrated on finding Fvs of high affinity and have not been concerned about the epitopes recognized by these Fvs. Binding of a Fv to a special epitope on the surface antigen, however, might affect various biological events such as antigen shedding, internalization, and signal transduction. In the case of CD30, there is evidence that the ability of an anti-CD30 MAb, Ki-4, to inhibit shedding of CD30 may explain the relatively high activity of the immunotoxin produced with this antibody (Klimka et al., *Br. J. Cancer*, 80:1214-1222 (1999); Horn-Lohrens et al., *Int. J. Cancer*, 60:539-544 (1995) ("Horn-Lohrens 1995"); Schnell et al., *Int. J. Cancer*, 631.138-244 (1995)). Also, MAbs, HeFi-I and M44, had been reported to have antitumor effects on ALCL cells (Tian et al., *Cancer Res.*, 55:5335-5341 (1995); Pfeifer et al., *Am. J. Pathol.*, 155:1353-1359 (1999)). These MAbs are known to share the same epitope associated with CD30-ligand binding (Franke et al., *Hybridoma*, 19:43-48 (2000)). These studies suggest that immunotoxins containing Fvs that bind to this epitope would have high cytotoxic activity.

In our study, the six Fvs obtained were all highly reactive to native CD30 on human cells by FACS (Table 1). Their epitopes were classified into two groups, I and II (Table 2). In previous studies, three major groups of epitopes (clusters A, B, and C) on native CD30 have been identified (Horn-Lohrens 1995; Franke et al., *Hybridoma*, 19:4348 (2000)). This study and the two previously mentioned studies included the characterization of the following MAbs: Ber-H2, HRS4 and HeFi-I. Since epitope I (in our study) and cluster A (in previous studies) both include Ber-H2 and HRS4 and because epitope II and cluster C both include HeFi-I, it is likely that epitope I and II are the same as cluster A and C, respectively.

The epitope of Ki-4 (a MAb reported for its inhibitory effects on shedding of CD30) belongs to the same group, epitope I or cluster A, as the following newly produced MAbs: T6, T13, T14 and T21 (Horn-Lohrens 1995). T24 and P-5, belong to the same epitope group, epitope II or cluster C, as HeFi-I, which has been reported to possess anti-tumor activity (Pfeifer et al., *Am. J. Pathol.*, 155:1353-1359 (1999)). Our panel of MAbs, therefore, covers the epitopes of the previous MAbs that had been reported to have biological activities. Our previous immunotoxin, CL2(scFv)-PE38, belongs to epitope I or cluster A (Rozemuller et al., *Int. J. Cancer,* 92:861-870 (2001)).

Production of the dsFv-based Immunotoxins by Use of the Fvs Isolated. We obtained unique cDNAs encoding both the VH and VL of six MAbs (T6, T13, T14, T24, T25 and Hefi-I) except VH of T21. All the deduced amino acid sequences were different from the sequences of the Ki-4 Fv and our previous anti-CD30 scFv (FIG. 2). This suggests that the characteristics of immunotoxins derived from these Fvs are different from previous immunotoxins. Because all the sequences contain significant numbers of mutated residues, when compared to the closest germ line sequences, these Fvs represent a repertoire of antibodies that had undergone the affinity maturation process in vivo. We succeeded in producing four fully recombinant dsFv-PE38s with reasonable yield and purity.

Effects of Immunotoxins on Cancer Cells. All the immunotoxins showed specific binding to CD30 on cells with different affinities with Kds varying from 4-410 nM. Consistent with their binding characteristics, the produced immunotoxins showed specific cytotoxic activity on CD30-transfected cells and CD30-positive cancer cells (Table 5). Several lines of evidence demonstrated that the killing was mediated by binding of the Fv portions of the immunotoxins to their own epitopes of CD30 on the cells.

Since the topographical epitope and affinity of each immunotoxin were determined in this study, we can analyze the relationship between the cytotoxic activity and these properties. The $IC_{50}$s from cytotoxicity assays varied over a 100-fold range depending on the immunotoxin and cell line used. Although it is clear that T6 and T14-A bind to epitope I and T24 and T25 bind to epitope II, no significant correlation was observed between binding to these epitopes and the cytotoxic activities of the immunotoxins. In contrast, when comparing the activity of these immunotoxins on each cell line, their activity was well correlated with their affinity. These results suggest that the affinity to CD30 is the primary factor to determining the efficacy of these immunotoxins.

Another notable finding from the cytotoxicity assays is that a large difference was seen in the susceptibilities of the CD30-positive cell lines to the immunotoxins (Table 5). The difference in susceptibility was not related to the CD30 level on the cells but was correlated with their $IC_{50}$ values of an immunotoxin (HB21 (scFv)-PE40) targeting the transferrin receptor. These results suggest that the differences in susceptibility to CD30 targeted toxins may be due to the different sensitivities of the cells to PE. We also investigated whether soluble CD30, produced by shedding of CD30, might influence the $IC_{50}$ by competing for the immunotoxins and explain the difference in susceptibilities. Soluble CD30 secreted in the culture supernatants of L428 and L540 cells, however, did not inhibit the cytotoxicity either of the T6 or T25 immunotoxins on A431/CD30 cells. Since only the supernatant of CD30 cell lines was used, however, it is possible that the amounts of CD30 present were simply not sufficient to successfully compete for binding of immunotoxins with CD30+ cells. Because significant cytotoxicity was detected with almost all CD30-positive cells tested, the factors affecting the sensitivity of cells to PE have not yet been pursued. Several mechanisms have been considered, such as differences in internalization rates of CD30 and differences in processing of PE. A preliminary experiment using furin-cleaved immunotoxins showed that the decreased sensitivity of L540 cells is not due to a defect in intracellular processing, which is required for its cytotoxic activity.

Thus, two powerful immunotoxins, T6 and T25(dsFv)-PE38 were produced which are useful agents for the treatment of CD30-positive cancers.

Example 4

This Example sets forth materials and methods used in Example 5.

Production of MAbs: Balb/c mice were injected intradermally three times with 15 ug of pHRm30c DNA, which is a plasmid encoding full-length human CD30 under the control of a CMV promoter. After 4 weeks, $2 \times 10^7$ L540 cells were injected, i.v. Spleen cells were harvested on day 3 and fused with Sp2/O cells using PEG. Hybridoma culturing was carried out by a standard protocol.

ELISAs and FACS: Binding of MAbs to CD30 were tested by two types of ELISAs and by FACS. In one type of ELISA (CD30-Fc ELISA), microtiter plates were coated with 25 ng/well of CD30-Fc. Culture supernatants of hybridoma were added to the coated wells, and bound MAbs were detected with HRP-labeled rat anti-mouse kappa chain monoclonal antibody. A different format of ELISA. Ig-trap ELISA, was also carried out. MAbs were captured by anti-mouse IgG coated on the plates, and then reacted with various concentrations of CD30-Fc in solution. The bound CD30-Fc was detected with HRP-labeled goat anti-human Fc antibody. In the FACS analyses, $2 \times 10^5$ L540 cells were incubated with appropriate dilutions of MAbs in 100 ul of PBS containing 5% FBS and 0.1% sodium azide. The bound MAbs were detected with R-PE labeled anti-mouse IgG.

Determination of affinity: Each MAb was titered in the CD30-Fc ELISA described above and an appropriate dilution for each MAb was selected from the liner range of the titration curves. The selected concentrations of MAbs were incubated with serial dilutions of CD30-Fc (0.1 nM-100 nM) in culture medium (IMDM containing 15% FBS) at room temperature overnight to reach equilibrium. The free MAb concentration in each equilibrium reaction was measured by the same ELISA using standard curves. No re-equilibrium occurred during the ELISA because of the small amounts of coated CD30-Fc and the short time of incubation. The CD30-Fc concentration giving half free MAb was the Kd. If [Ab] total<<Kd, when [Ab]=[Ab–Ag] (half-maximal), Kd=[Ab] [Ag]/[Ab–Ag]=[Ag]≈[Ag]total Topographical epitope mapping by an ELISA: Mutual competition of each pair of MAbs (e.g., MAb#1 and #2) for binding to CD30-Fc was examined as follows: Plates were coated with goat anti-mouse IgG, and one MAb (e.g. MAb#1) presented in culture supernatant of the hybridoma. In a different plate, CD30-Fc and MAb#2 were mixed to form the immune complex. After overnight incubation, the mixture was added to the platee that had been coated with MAb#1. If the MAb#2 reacts to a different epitope from the MAb#1, the immune complex binds to MAb#1 coated on the plates. If the epitopes of the two MAbs are the same, the immune complex cannot bind to MAb#1 because the MAb#2 has already occupied its epitope.

Effects of soluble CD30 on the MAb binding to CD30-Fc: An appropriate dilution of each MAb was reacted with the CD30-Fc coated on the ELISA plate in the presence of various dilutions of soluble CD30 (L540 culture sup.), CD30-Fc (positive control), and A431 culture sup. (negative control).

The MAbs bound to the plate were detected by HRP-rat anti-mouse kappa MAb.

Example 5

This Example sets forth the results of studies on new anti-CD30 immunotoxins.

Production of anti-CD30 MAbs The spleen cells of mice that were DNA-immunized followed by a single injection of CD30-positive cells were fused. This new protocol give high yields of total hybridomas and specific (anti-CD30) hybridomas.

Fusion experiments gave 16 anti-CD30 MAbs, all of which reacted to CD30-Fc in ELISA. The characteristics of these MAbs are summarized in Table 6.

Reactivities of the anti-CD30 MAbs to different type of CD30 antigen The reactivity of the new MAbs was confirmed in a different format of ELISA, in which the MAbs captured by anti-mouse IgG coated on the plates, and then reacted with various concentrations of CD30-Fc in solution (Ig-trap ELISA).

The titers in the two ELISAs did not perfectly correlate to each other. In another ELISA using recombinant sCD30 produced in E. coli as the coating antigen, different titers were also obtained. The differences among assays might be partially explained by the conformational change of CD30-Fc during the coating, difference between the two kinds of antigens, or different reactivities of secondary antibodies to different subclass of mouse Ig.

FACS analysis revealed that all the new MAbs reacted to native CD30 on L540 cells. The staining intensities were the same as or superior than those of reference MAbs (BerH-2, HRS4, HeFi-I). The FACS data was less quantitative than ELISA, but permitted rough rankings of MAbs by their reactivities. T420 showed the highest intensity of the staining; while T13, T103, T411, T406, T427 exhibited higher reactivities than the other MAbs.

As shown in Table 6, the correlation of the titers to FACS signals was best with Ig-trap ELISA. For example, MAb T427 showed the highest reactivity in FACS and in Ig-trap ELISA, but not in the CD30-Fc ELISA. It is likely that CD30-Fc in solution keeps a similar conformation as the native CD30 antigen on the cell surface and the coating of CD30-Fc on plastic may slightly alter its conformation.

Affinities of the anti-CD30 MAbs To select MAbs with the highest affinities for making immunotoxin, the dissociation constants (Kd) of the MAbs to CD30-Fc in solution were determined by ELISA. They ranged from 0.9 to 12.4 nM (Table 6).

The top 2 MAbs in the affinity ranking were T427 (Kd=0.9 nM) and T420 (Kd=1.9 nM), which were also ranked in the top 6 MAbs in FACS and Ig-trap ELISA. From these data, it was concluded that T427 and T420 were the two best binders to CD30 molecule on cells.

Competitive binding assay to determine topographical epitopes of the anti-CD30 MAbs Because of the possibility that the epitopes of antibodies and immunotoxins made from them may relate to their efficacy, we determined the topographical epitopes of the new anti-CD30 MAbs.

To do this, we developed a new competitive ELISA method, which enabled us to map the topographical epitopes. Usually, antibody purification and labeling is necessary to establish a competitive assay for two MAbs. Our new method does not require the purification and labeling of MAb(s). In addition, we showed that the method is applicable to hybridoma culture supernatant before cell cloning without determination of the concentrations of MAbs.

Pairs of MAbs were examined for their competition with each other. CD30-Fc (10 ng/ml) was incubated with more than a 100-fold excess amount of the competitor MAb (~>1 µg/ml). In this condition, competition by the self-MAb usually reached to 90%.

When mutual competition was observed, the two MAbs were considered to share the same epitope. For grouping of the epitopes, inconsistency was minimized. A total of 6 groups of epitopes were identified using 28 anti-CD30 MAbs. If the binding of some MAbs in one group affected the binding of a MAb in another group or were affected by the binding of MAbs that bound to a different epitope, the MAbs were classified as a subgroup. Epitope ("Ep") II and Ep III were divided into two subgroups by these criteria.

Assignment of reference MAbs and our MAbs in the epitope mapping were consistent with the literature and previous competitive FACS analysis. Our new MAbs defined EpIIa, EpIIIa and EpVI for the first time. The competition pattern demonstrated the clustering of EpII, EpIII and EpIV, because an EpIIb MAb was competed by EpIII MAbs and because EpIIIb MAbs competed with EpIV MAbs. A relationship was also shown between EpI and EpIII, because one EpIIIb MAb (T427) inhibited the binding of some EpI MAbs (Ber-H2, T13 and T420); some EpI MAbs Mr7, T13, T103) competed with some of the EpIII MAbs. It appeared that EpV might be related to EpIIa, because one EpV MAb (T201) showed a weak competition to the binding of some EpIIa MAbs. EpVI is an independent epitope.

Reactivity of the anti-CD30 MAbs to soluble CD30 produced by shedding of CD30 on cells. It is known that the extracellular domain of CD30 can be cleaved by cellular proteases such as TIMP-3 to produce a soluble CD30 molecule. Soluble CD30 could inhibit the binding of some anti-CD30 MAbs and immunotoxins to full-length of CD30 expressed on the surface of cancer cells. We, therefore, examined the reactivity of the anti-CD30 MAbs to soluble CD30 produced by L540 cells.

The binding of soluble CD30 (culture supernatant of L540 cells) to each MAb was tested in a competitive ELISA. Each MAb was reacted to CD30-Fc coated on the plates in the presence of soluble CD30, CD30-Fc (positive control), or A431 culture supernatant (negative control). The competition by soluble CD30 varied depending on the epitope bound by the MAb. Soluble CD30 inhibited the binding of Ep I, III, and IV MAbs to an extent similar to that of CD30-Fc (control), suggesting that soluble CD30 possesses these epitopes. As for the MAbs for Ep IIb and V, the inhibition by soluble CD30 was seen but was only partial when compared to that by CD30-Fc. The competition curves of soluble CD30, and CD30-Fc were not parallel, suggesting a qualitative difference of the epitopes in these two antigens. EpIIb and V are apparently located near the cleavage site and on soluble Cb30 side and the cleavage might slightly alter the epitope structure. In contrast to the above results, no competition by soluble CD30 was observed with MAbs for Ep IIa and VI. This indicates that these two epitopes do not exist on soluble CD30. It is believed that the two epitopes remain on the cell surface after cleavage of sCD30 (non-shed epitopes). There remain a lesser possibility that the epitopes are destroyed by the cleavage of sCD30. In either case, antibodies binding to these epitopes bind to native CD30 prior to its cleavage and not to sCD30. Thus, if the intent is to bind antibodies to cells expressing CD30, lower quantities of antibodies binding to these antibodies would be needed than would be needed of antibodies that bind to sCD30. The non-shed epitopes identified by our new anti-CD30 MAbs have not previously been reported.

Relationship between the biological activities of the anti-CD30 MAbs and their epitopes Biological activities of anti-CD30 MAbs may add advantageous or disadvantageous properties to immunotoxins using the MAbs as their targeting moieties. The biological activities of MAbs are probably related to their epitope locations. It is, therefore, important to know the relationship between the biological effects of MAbs and their epitopes.

CD153, commercially available from Research Diagnostics Inc. (Flanders, N.J.), is the CD30 ligand (CD30L) expressed on some type of activated lymphocytes. The binding site of CD30L on CD30 had been analyzed using several anti-CD30 MAbs and recombinant soluble CD30L (Franke et al., Hybridoma, 19:43-8 (2000)). The competitive effect of each MAb on the binding of CD30L to native CD30 on Karpas299 cells was measured. As a result, it was concluded Ep I (BerH-2 and HRS-4) and Ep IIb (HeFi-I) are on or close to the binding site for CD30L. Ep V (Ki-I and M67) was estimated to be far from the binding site.

Some anti-CD30 MAbs have been shown to inhibit or enhance the shedding of CD30 from Karpas299 cells (Horn-Lohrens et al., 1995). BerH-2 and Ki-4 (both of which recognize Ep I) showed inhibitory effects on the shedding. In contrast, HeFi-I (which binds Ep IIb) and Ki-I (which binds Ep V) enhanced the shedding of CD30. Our mapping experiments show that both Ep IIb and Ep V are defined as "near cleavage" epitopes. Thus the binding of MAbs to these epitopes might change the conformation of the cleavage site and increase its accessibility to shedding enzymes.

CD30 has been implicated both in cell death and in proliferation. There are several reports on the effects of anti-CD30 MAbs on various types of cells. Mir et al., Blood, 96:4307-12 (2000), reported the induction of cell death (using Karpas299 cells, an anaplastic large cell lymphoma cell line) by treatment with M67 MAb (which binds Ep V). Testing of some of our MAbs in the same assay suggested that antibodies that bound EpI, EpIIIb and EpIV have no activity on inducing apoptosis. M67 MAb was also reported to stimulate proliferation of some T-cell lines and for Ig secretion from EBV-transformed B-cell lines (Gruess et al., Blood. 83(8):2045-56 (1994)). HeFi-I (which binds to Ep IIb) was reported to show in vivo inhibitory effects on Karpas299 and Michael cell growth (Tian et al. 1995). In the same paper, BerH-2 showed no effects on cell growth. Considering the information in these references, antibodies that bind to epitopes IIb and V may show relatively strong agonistic activities. It should be remembered, however, that these effects might be related to dimerization of CD30 by the MAbs.

Location of epitopes on CD30 structure based on the results A model of the structure of CD30 was constructed from the results of our studies. Comparisons of the cross competition of the various antibodies permitted the following relative positions of the epitopes to be deduced: (1) Epitopes II, III, IV are close to each other because members showed cross competition for the binding to CD30; (2) Epitopes I and III are close to each other, again because of cross competition; (3) Epitopes I, III and IV are far from the cleavage site; (4) Epitopes IIb and V are close to the cleavage site; (5) Epitopes Ia and VI are epitopes which are not shed by cleavage, or are located at the cleavage site; (6) Epitopes I and IIb are on or near the CD30L binding site.

Example 6

This Example sets forth methods and results of studies on complement-dependent cytotoxicity.

Methods. Anti-CD30 antibodies and rabbit antimouse F(ab')2 were diluted with culture medium. Cells were resuspended at a density of 1×106 cells/mL with culture medium. Complement was rehydrated with culture medium. Assays of antibodies were conducted by adding 50 µL of the anti-CD30 antibody (in medium containing 5-fold excess of a secondary antibody and 9-fold dilution of complement), with or without a secondary antibody, to a flat bottom tissue culture 96-well plate, along with 50 µL of 1/3 dilution of complement, and 50 µL of a cell suspension ($5\times10^4$ cells/well). The mixture was incubated for 4 hours at 37° C. in a 5% $CO_2$ incubator. 10 µL of solution of the tetrazolium salt WST-1 (available, for example, from Roche Diagnostics Corporation (Indianapolis, Ind.) was added to each well of the plate. After 15 hours of incubation at 37° C., 5% $CO_2$, the absorbance was read at 450/650 nm.

Results. As shown in FIGS. 6a and 6b, studies using the CD30+ cell line Karpas299, an anaplastic large cell lymphoma cell line, antibodies T420, T427, T405 and AC10 showed complement-dependent cytotoxicity at 1 µg/mL. On L540 cells, a Hodgkin's disease cell line, these antibodies showed complement-dependent cytotoxicity at 1 µg/ml, as did the IgG2a antibody T408.

Example 7

This Example reports the results of studies on the cytotoxicity of immunotoxins T6, T104, T201, and T408 on a cell line, A431, transfected with CD30, and the same cell line transfected with an irrelevant antigen, CD25. The antibodies were made into dsFv immunotoxins using PE38 as an exemplar toxin.

Figure 7A:
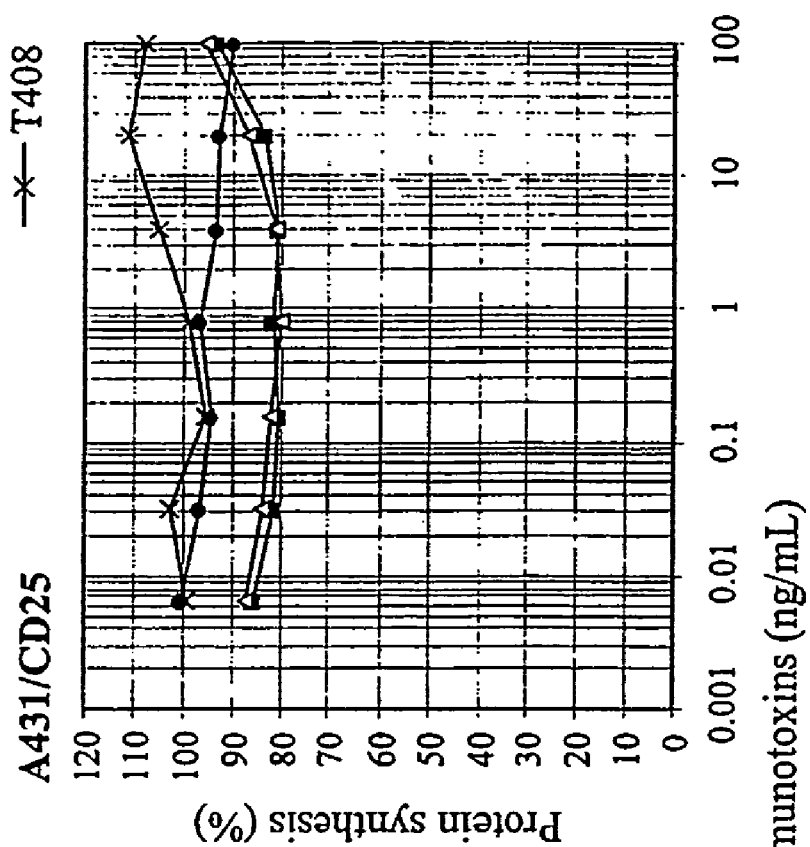
FIGS. 7a and 7b. These graphs present the results of studies of the cytotoxicity of various immunotoxin made from antibodies of the invention.
Figure 7B:
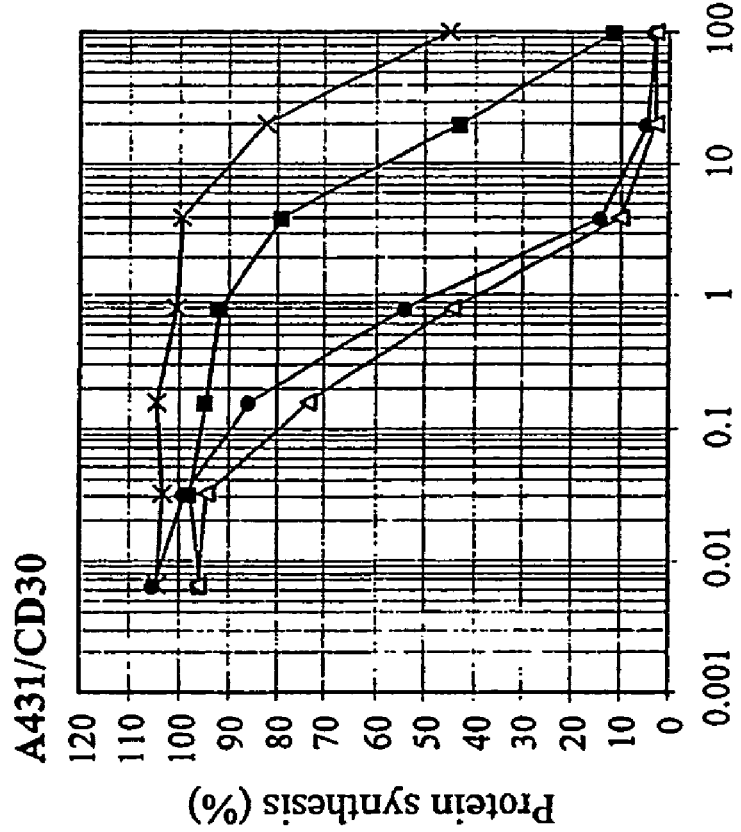

Cell were seeded into 96-well plates at a concentration of $2.0\times10^4$ cells/well and incubated for 24 hours. The immunotoxins were diluted in Dulbecco's Modified Eagle Medium (DMEM) were added to the wells, resulting in final concentrations ranging from 0.0064 to 100 ng/mL. After incubation for 24 hours, 2 µCi of [$^3$H]leucine was added per well and incubated for 3 hours. The cells were then frozen and thawed twice and harvested onto glass filters using a cell harvester. The radioactivity associated with the cells was determined in an automated scintillation counter. As shown in FIGS. 7a and 7b, immunotoxins made with T6 and T201 were quite potent in killing CD30-expressing cells, while the immunotoxins had only modest cytotoxicity to cells expressing an irrelevant antigen.

Example 8

This Example reports the results of studies on the cytotoxicity of immunotoxins T6, T13, T105, and T201 on (1) cell line SUDHL1, from an anaplastic large cell lymphoma, (2) a Hodgkins' Disease cell line, L540, and (3) a Burkitt's lymphoma cell line, Ramos, that does not express CD30. The antibodies were made into dsFv immunotoxins using PE38 as an exemplar toxin.

Cell were seeded into 96-well plates at a concentration of $2.0\times10^4$ cells/well and incubated for 1 hour. The immunotoxins were diluted in RPMI medium and were added to the wells, resulting in final concentrations ranging from 0.032 to 500 ng/mL. After incubation for 24 hours, 2 µCi of [$^3$H] leucine was added per well and incubated for 3 hours. The cells were then harvested onto glass filters using a cell harvester. The radioactivity associated with the cells was determined in an automated scintillation counter. As shown in FIGS. 8a-c, all four immunotoxins showed considerable cytotoxicity to SUDHL1 cells, much less cytotoxicity to L540 cells, and almost no activity against the control Ramos cells.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

TABLE 1

Characteristics of Selected Anti-CD30 MAbs

| Name | Isotype | Titer in ELSA (ml/μg)[a] sCD30 | CD30-Fc | Relative reactivity to native CD30 on cells in FACS analysis (% of control)[b] L428 (CD30-low)[d] | L540 (CD30-high)[d] | Topographical epitopes[c] |
|---|---|---|---|---|---|---|
| T6 | γ1, κ | 74.1 | 40.0 | 140.0 | 111.1 | I-a |
| T13 | γ1, κ | 87.7 | 91.2 | 180.0 | 111.1 | I-a |
| T14 | γ2b, κ | 138.9 | 100.0 | 60.0 | 100.0 | I-b |
| T21 | γ1, κ | 128.2 | 66.6 | 160.0 | 111.1 | I-b |
| T24 | γ1, κ | 102.0 | 179.2 | 160.0 | 116.7 | II-b |
| T25 | γ1, κ | 135.1 | 50.0 | 80.0 | 27.8 | II-c |
| HeFi-I[e] | γ1, κ | 105.3 | ND[f] | 100.0 | 100.0 | II-a |
| Ber-H2[e] | γ1, κ | 50.0 | 75.0 | 160.0 | 111.1 | I-a |
| HRS-4[e] | γ1, κ | ND | 50.0 | ND | ND | I-a |

[a]The reciprocal of the MAb concentration needed to attain an absorbance of 0.2 in ELISA when a positive control (BerH-2, 40 ng/ml) had an absorbance value of 0.4 in the same plate. These values are equal to the titers of 1 μg/ml of MAb solution. In the ELISA, sCD30 or CD30-Fc was coated on the plates and various concentrations of MAbs were added. The titer was calculated from the titration curves by using second degree polynomial curve-fitting after logit-log transformation of the data. All MAbs did not react to a negative control (recombinant PAGE-4 protein with His-tag) in a similar ELISA.
[b]The fluorescence intensity of the cells stained with each MAb in FACS analysis. CD30-positive cells, L428 or L540, were incubated with each MAb (5 μg/ml), and then followed by incubation with FITC-labeled anti-mouse IgG. The sensitivity of the detector for fluorescence was set to an appropriate range using a positive control (HeFi-I) and a negative control (mouse IgG1). The values were determined from the peak of the histograms and shown as the percentage of the positive control. The fluorescence levels of the negative control were 16% and 0.2% for L428 and L540, respectively.
[c]Topographical epitopes determined in an competitive FACS analysis shown in Table 2. Two primary groups of epitopes, I and II, were identified and they were divided into subgroups (a, b, c).
[d]The numbers of CD30 molecules on L428 and L540 had been estimated as $4.6 \times 10^4$ and $5.2 \times 10^5$ per cell in a Scatchard analysis using radiolabeled HRS-4 MAb.
[e]Anti-CD30 MAbs established in previous studies were used as positive controls in this study.
[f]Not determined

TABLE 2

Topographical epitope mapping of anti-CD30 MAbs by a competitive FACS analysis[a]

| MAb | Inhibition of the binding of indicated biotin-MAb to L540 cells (%)[b] HRS-4 | T6 | T14 | HeFi-I | T24 | T25 | Topographical epitopes[c] |
|---|---|---|---|---|---|---|---|
| Ber-H2 | <u>80.3</u> | <u>75.6</u> | <u>107.5</u> | 0.0 | 18.2 | 23.3 | I-a |
| HRS-4 | <u>82.6</u> | <u>87.4</u> | <u>107.5</u> | 0.0 | 3.9 | 25.0 | I-a |
| T6 | <u>97.9</u> | <u>100.0</u> | <u>107.5</u> | 0.0 | 3.9 | 25.0 | I-a |
| T13 | <u>82.6</u> | <u>87.4</u> | <u>107.5</u> | 0.0 | 40.1 | 26.7 | I-a |
| T14 | 0.0 | 1.5 | <u>90.6</u> | 0.0 | 0.0 | 20.2 | I-b |
| T21 | 2.7 | 52.6 | <u>100.0</u> | 6.1 | 3.9 | 26.7 | I-b |
| HeFi-I | 0.0 | 0.0 | 0.0 | <u>98.0</u>[d] | 33.4 | 8.4 | II-a |
| T24 | 52.2 | 1.5 | 16.1 | <u>79.8</u> | <u>82.8</u> | <u>97.8</u> | II-b |
| T25 | 0.0 | 1.5 | -1.3 | 0.0 | 0.0 | <u>79.8</u> | II-c |

[a]L540 cells were stained with 50 ng/ml of each biotinylated MAb in the presence or absence of 2.5 μg/ml of various unlabeled MAbs (50-fold excess). The cell-bound biotinylated MAbs were detected by streptavidin conjugated with R-phycoerythrine. The detector sensitivity of FACS machine had been adjusted to give a sub-linear dose response for biotinylated MAbs concentrations of 0-500 ng/ml. The used concentration (50 ng/ml) of the biotinylated MAbs corresponded to the dose that gave 50% fluorescence intensity in the titration curves.
[b]The fluorescence intensities of the peaks in the histograms were log-converted corrected for background contribution by subtraction of the value of non-stained cells and were expressed as the percentage of the competition.
[c]Topographical epitopes determined by the competition pattern. At first, MAbs were classified in the same epitope when the unlabeled MAb decreased the binding of biotinylated MAb to less than 25% of control (>75% of competition). The identified two primary epitopes (I and II) then divided into subgroups (a, b, c) based on the inhibition pattern to the panel of biotinylated MAbs.
[d]Inhibitions of more than the threshold (75%) for the epitope assignment are underlined.

TABLE 3

Production of anti-CD30 dsFv immunotoxins[a]

| dsFv immunotoxin | Recovery of recombinant prot as inclusion bodies (mg/L of *E. coli* culture) VH(Cys)-PE38 | VL(Cys) | Recovery of dsFv-PE38 after refolding and purification (%)[b] |
|---|---|---|---|
| HeFi-I | 4 | 55 | ND[c] |
| T6 | 65 | 35 | 3.0 |
| T13 | 4 | 60 | ND |
| T14-A | 350 | 60 | 7.5 |
| T14-B | 350 | 50 | not pure[d] |
| T24 | 103 | 113 | 5.3 |
| T25 | 90 | 28 | 1.0 |

[a]Each recombinant protein was separately expressed in *E. coli* BL21(λDE3). The proteins accumulated in inclusion bodies were harvested by centrifugation. After solubilization and reduction, each VL(Cys) chain protein was combined with the appropriate VH(Cys)-PE38 chain and refolded into dsFv-PE38 as described in Example 1. Properly refolded dsFvs were purified by anion exchange and gel filtration column chromatography.
[b]The recovery percentages of the purified dsFv-PE38 from the inclusion bodies.
[c]Not done, due to the low expression of the VH(Cys)-PE38 chain.
[d]Pure dsFv-PE38 could not be obtained by the protocol that had been established for the other dsFv-immunotoxins.

TABLE 4

Kinetic constants for the purified anti-CD30 dsFv immunotoxins and anti-CD30 MAb interacting with immobilized sCD30 by a surface plasmon resonance analysis[a]

| Sample | On rate $K_{on}$ (M$^{-1}$s$^{-1}$) | Off rate $K_{off}$ (s$^{-1}$) | Affinity Kd (nM) |
|---|---|---|---|
| T6(dsFv)-PE3 | $6.7 \times 10^4$ | $1.5 \times 10^{-3}$ | 22 |
| T14-A(dsFv)-PE38 | $1.1 \times 10^4$ | $5.2 \times 10^{-2}$ | 410 |
| T24(dsFv)-PE38 | $1.0 \times 10^5$ | $1.0 \times 10^{-2}$ | 100 |
| T25(dsFv)-PE38 | $4.4 \times 10^4$ | $1.6 \times 10^{-4}$ | 4.0 |
| CL2(scFv)-PE38[b] | $3.8 \times 10^4$ | $2.2 \times 10^{-3}$ | 56 |
| HeFi-I MAb[c] | $7.2 \times 10^4$ | $5.4 \times 10^{-4}$ | 7.8 |

[a]Samples (25 μg/ml) were injected over sCD30 proteins immobilized on the sensor chip then allowing the bound material to dissociate in the buffer flow. The surface plasmon resonance measured by BIAcore machine was analyzed using BIAevaluation 2.1 software.
[b]An anti-CD30 scFv immunotoxin previously produced (Rozemuller et al., Int. J. Cancer, 92: 861-870 (2001)).
[c]The value is not corrected for the bivalency of MAb.

TABLE 5

Susceptibilities of various cell lines for anti-CD30 immunotoxins

| | | IC$_{50}$ (ng/ml) in cytotoxicity test[b] | | | | | |
|---|---|---|---|---|---|---|---|
| Cell lines | Source[a] | T6 | T14-A | T24 | T25 | HB21 | CD30 level (a.u.)[c] |
| A431/CD30 | TF | 0.5 | 300 | 10 | 0.3 | 0.02 | 200 |
| A431/CD25 | TF | 200 | 500 | 500 | 500 | 0.03 | <10 |
| KM-H2 | HL | 20 | NT | NT | 12.5 | 0.2 | 250 |
| L428 | HL | 400 | >1000 | >1000 | 1000 | 3.0 | 150 |
| L540 | HL | 60 | >1000 | >1000 | 60 | 5.0 | 900 |
| L591 | HL | 40 | NT | NT | 40 | 1.0 | 250 |
| SR-786 | ALCL | 80 | >1000 | 500 | 40 | 3.0 | 600 |
| SUDHL-1 | ALCL | 6.0 | NT | 20 | 3.0 | 0.05 | 300 |
| SUP-M2 | ALCL | 12 | NT | 60 | 7.0 | 0.02 | 350 + 1000[d] |
| KARPAS-299 | ALCL | 6.0 | >1000 | 100 | 10 | 0.3 | 500 |
| HUT102W | ATL | 150 | NT | NT | 25 | 1.5 | 250 |
| S1T | ATL | 50 | NT | NT | 50 | 0.5 | 120 |
| DEL | MH | NT | NT | 500 | 100 | NT | NT |

[a]TF, transformant; HL, Hodgkin's lymphoma; ALCL, anaplastic large cell lymphoma; ATL, adult T-cell leukemia; MH, malignant histocytosis.
[b]The average IC$_{50}$ values in 1-5 different cytotoxicity experiments. T6, anti-CD30 T6(dsFv)-PE38; T14-A, anti-CD30 T14-A(dsFv)-PE38; T24, anti-CD30 T24(dsFv)-PE38; T25, anti-CD30 T25(dsFv)-PE38; and HB21, anti-transferrin receptor HB21(scFv)-PE40.
[c]The fluorescence intensity of the cells stained with anti-CD30 T25 MAb in FACS analysis are shown in arbitrary unit (a.u.). The numbers of CD30 molecules on L428 and L540 had been estimated as $4.6 \times 10^4$ and $5.2 \times 10^5$ per cell in a scatchard analysis using radiolabeled HRS-4 MAb.
[d]This cell line consists of two populations with different levels of CD30 expression.

TABLE 6

Summary of anti-CD30 monoclonal antibodies and dsFv-PE38 immunotoxins made from their Fvs[a]

| Clone[b] | Epitope[c] | Affinity of MAb[d] (Kd, nM) | Affinity of dsFv immunotoxin[e] (Kd, nM) | Cytotoxicity of dsFv immunotoxin[f] (IC50, ng/ml) |
|---|---|---|---|---|
| T6 | I | 13.0 | 22.0 | 0.4-0.8 |
| T13 | I | 3.1 | NT | 0.7 |
| T14-A | I | NT[g] | 410.0 | 300 |
| T24 | IIIb | 2.2 | 100.0 | 10.0 |
| T25 | IV | 6.4 | 4.0 | 0.2-0.8 |
| T420 | I | 1.9 | NT | 1.5 |
| T105 | IIa (stalk) | 4.2 | NT | 0.6[h] |

[a]All Fvs listed were converted to dsFv-immunotoxins. There is no clear correlation between the affinities of the parental antibodies and the affinities and cytotoxicities of the derived immunotoxins; indicating that it cannot be predicted which Fvs are suitable for use as recombinant immunotoxins.
[b]All Fvs were molecularly cloned. Deduced amino acid sequences are shown in FIG. 2.
[c]Topographical epitope determined by competitive ELISA assay using CD30-Fc protein.
[d]Affinity of MAbs was determined in ELISA using CD30-Fc.
[e]Affinity of immunotoxins was determined in biosensor analysis (BIAcore) using soluble CD30 made in E. coli.
[f]Cytotoxicity against A431/CD30 cells. Inhibition concentration 50 (IC50) was determined by inhibition of cellular protein synthesis after 24 hr treatment of various concentrations of immunotoxin.
[g]NT, not tested.
[h]Assay shows cytotoxicity, but was not conducted under conditions that would show advantage of stalk-binding ITs in avoiding dilution by binding to free sCD30.

TABLE 7

Summary of anti CD30 immunotoxins

| Antibody | Epitope | Subclass | IT Yield (%) | Affinity Mab | (Kd, nM) IT | Cytotoxicity A431/CD30 | (IC50, ng/mL) Karpas 299 | SUDHL1 | Ramos |
| --- | --- | --- | --- | --- | --- | --- | --- | --- | --- |
| T6 | I | G1 | 3.0 | 13.0 | 22(17) | 0.5 | 6 | 6(3) | >500 |
| T7 | I | A | not pure | 3.5 | ND | ND | ND | ND | ND |
| T13 | I | G1 | 7.25 | 3.1 | 24 | 0.7 | 18 | 27(3) | >500 |
| T14 | I | G2b | 7.5 | NT | 410 | 300 | ND | ND | ND |
| T420 | I | G2b | 4.27 | 1.9 | 58 | 1.5 | 53 | 18 | >500 |
| T25 | IV | G1 | 1.0 | 6.4 | 4 | 0.3 | 10 | 3 | ND |
| T24 | IIIb | G1 | 5.3 | 2.2 | 100 | 10 | ND | ND | ND |
| T427 | IIIb | G2a | 5.18 | 0.9 | 36 | 2.1 | 41 | 13 | >500 |
| HeFi-I | IIb | G1 | ND | 2.4 | ND | ND | ND | ND | ND |
| T104 | V | G1 | 5.61 | 7.4 | (70) | 14 | 230 | ND | >500 |
| T201 | V | G1 | 9.44 | 8.3 | (8.3) | 0.6 | 6 | (1.9) | >500 |
| T105 | IIa | G1 | 5.58 | 4.2 | 12 | 0.6 | 17 | 8(2.8) | >500 |
| T215 | IIa | G1 | not refolded | 5.9 | ND | ND | ND | ND | ND |
| T405 | VI | G2b | 5.85 | 5.7 | 310 | 200 | >100 | >100 | ND |
| T408 | VI | G2a | 0.46 | 6.4 | (330) | 80 | 340 | ND | >500 |

Notes:
Immunotoxins (IT) were all dsFvs. To permit ready comparison, all were made with the same toxin, PE38. A431/CD30, Karpas299 and SUDHL1 cells express CD30; Ramos cells do not and were used as a negative control. Figures not in parentheses are from studies done on one day, figures in parentheses are from studies performed on a second day.

What is claimed is:

1. An isolated antibody that binds specifically to a stalk of CD30 of a cell, or to an epitope destroyed upon cleavage of soluble CD30 ("sCD30") from intact CD30 (SEQ ID NO:1), which antibody has complementarity determining regions ("CDRs"), which CDRs have the sequence of the CDRs of an antibody selected from the group consisting of antibodies T105, T405 and T408, as shown in FIGS. 2a and b.

2. An antibody of claim 1, wherein said antibody is selected from the group consisting of an Fab, a single chain variable region ("scFV"), and a variable heavy chain and a variable light chain connected by a disulfide bond ("dsFv").

3. An antibody of claim 1, further wherein said antibody has a variable heavy chain and a variable light chain, which variable heavy chain and said variable light chain are selected from the group consisting of: a variable heavy chain of SEQ ID NO:14 and a variable light chain of SEQ ID NO:29 (antibody T105), a variable heavy chain of SEQ ID NO:13 and a variable light chain of SEQ ID NO:28 (antibody T405), and a variable heavy chain of SEQ ID NO:40 and a variable light chain of SEQ ID NO:41 (antibody T408), and, optionally, further wherein a first cysteine residue is substituted for an amino acid residue in a framework region of said variable heavy chain and a second cysteine residue is substituted for an amino acid residue in a framework region of said variable light chain.

4. A composition comprising an antibody of claim 1, conjugated or fused to a therapeutic moiety or detectable label.

5. A composition comprising an antibody of claim 2, conjugated or fused to a therapeutic moiety or detectable label.

6. A composition comprising an antibody of claim 3, conjugated or fused to a therapeutic moiety or detectable label.

7. A composition of claim 4, wherein the therapeutic moiety is selected from the group consisting of a cytotoxin, a drug, a radioisotope, or a liposome loaded with a drug or a cytotoxin.

8. A composition of claim 5, wherein the therapeutic moiety is selected from the group consisting of a cytotoxin, a drug, a radioisotope, or a liposome loaded with a drug or a cytotoxin.

9. A composition of claim 6, wherein the therapeutic moiety is selected from the group consisting of a cytotoxin, a drug, a radioisotope, or a liposome loaded with a drug or a cytotoxin.

10. A composition of claim 4, wherein the cytotoxin is selected from the group consisting of ricin A, abrin, ribotoxin, ribonuclease, saporin, calicheamycin, diphtheria toxin, a *Pseudomonas* exotoxin A, and botulinum toxins A through F.

11. A composition of claim 5, wherein the cytotoxin is selected from the group consisting of ricin A, abrin, ribotoxin, ribonuclease, saporin, calicheamycin, diphtheria toxin, a *Pseudomonas* exotoxin A, and botulinum toxins A through F.

12. A composition of claim 6, wherein the cytotoxin is selected from the group consisting of ricin A, abrin, ribotoxin, ribonuclease, saporin, calicheamycin, diphtheria toxin, a *Pseudomonas* exotoxin A, and botulinum toxins A through F.

13. A composition of claim 4, further comprising a pharmaceutically acceptable carrier.

14. A kit for detecting the presence of a CD30+ cancer cell in a biological sample, said kit comprising:
(a) a container, and
(b) an anti-CD30 antibody of claim 1, fused or conjugated to a detectable label.

15. A kit of claim 14, wherein said antibody is selected from the group consisting of an scFv, a dsFv, a Fab, or a F(ab')2.

16. A kit of claim 14, further wherein said anti-CD30 antibody antibody has a variable heavy chain and a variable light chain, which variable heavy chain and said variable light chain are selected from the group consisting of: a variable heavy chain of SEQ ID NO:14 and a variable light chain of SEQ ID NO:29 (antibody T105), a variable heavy chain of SEQ II) NO:13 and a variable light chain of SEQ ID NO:28 (antibody T405), and a variable heavy chain of SEQ ID NO:40 and a variable light chain of SEQ ID NO:41 (antibody T408), and, optionally, further wherein a first cysteine residue is substituted for an amino acid residue in a framework region of said variable heavy chain and a second cysteine residue is substituted for an amino acid residue in a framework region of said variable light chain.

17. A kit of claim 16, further wherein said antibody is selected from the group consisting of an scFv, a dsFv, a Fab, or a F(ab')$_2$.

18. A nucleic acid encoding an antibody of claim 1.

19. A nucleic acid of claim 18, further wherein said antibody has a variable heavy chain and a variable light chain, which variable heavy chain and said variable light chain are selected from the group consisting of: a variable heavy chain of SEQ ID NO:14 and a variable light chain of SEQ ID NO:29 (antibody T105), a variable heavy chain of SEQ ID NO:13 and a variable light chain of SEQ ID NO:28 (antibody T405), and a variable heavy chain of SEQ ID NQ:40 and a variable light chain of SEQ ID NO:41 (antibody T408), and, optionally (1) wherein a first cysteine residue is substituted for an amino acid residue in a framework region of said variable heavy chain and a second cysteine residue is substituted for an amino acid residue in a framework region of said variable light chain and (2) said nucleic acid further encodes a polypeptide which is a therapeutic moiety.

20. A nucleic acid of claim 18, further wherein said nucleic acid encodes a polypeptide which is a therapeutic moiety.

21. An expression vector comprising a nucleic acid of claim 18 operably linked to a promoter.

22. An expression vector comprising a nucleic acid of claim 19, operably linked to a promoter.

23. An expression vector comprising a nucleic acid of claim 20 operably linked to a promoter.

24. A method of inhibiting growth of a CD30+ cancer cell by contacting said cell with a chimeric molecule comprising an antibody of claim 1 conjugated or fused to a therapeutic moiety, which therapeutic moiety inhibits growth of said cell.

25. A method of claim 24, wherein said antibody is selected from the group consisting of an scFv, a dsFv, a Fab, or a F(ab')2.

26. A method of claim 24, further wherein said antibody has a variable heavy chain and a variable light chain, which variable heavy chain and said variable light chain are selected from the group consisting of: a variable heavy chain of SEQ ID NO:14 and a variable light chain of SEQ II) NO:29 (antibody T105), a variable heavy chain of SEQ ID NO:13 and a variable light chain of SEQ ID NO:28 (antibody T405), and a variable heavy chain of SEQ ID NO:40 and a variable light chain of SEQ ID NO:41 (antibody T408), and. optionally, further wherein a first cysteine residue is substituted for an amino acid residue in a framework region of said variable heavy chain and a second cysteine residue is substituted for an amino acid residue in a framework region of said variable light chain.

27. A method of claim 24, wherein the therapeutic moiety is selected from the group consisting of a cytotoxin, a drug, a radioisotope, or a liposome loaded with a drug or a cytotoxin.

28. A method of claim 27, wherein the cytotoxin is selected from the group consisting of ricin A, abrin, ribotoxin, ribonuclease, saporin, calicheamycin, diphtheria toxin, a *Pseudomonas* exotoxin A, and botulinum toxins A through F.

29. A method of claim 24, wherein said antibody is a scFv or dsFv.

30. A method of claim 26 wherein said antibody is a scFv or dsFv.

31. A method of claim 26, wherein the therapeutic moiety is selected from the group consisting of a cytotoxin, a drug, a radioisotope, or a liposome loaded with a drug or a cytotoxin.

32. A method for detecting the presence of a CD30+ cell in a biological sample, said method comprising:
(a) contacting cells of said biological sample with an anti-CD30 antibody of claim 1 fused or conjugated to a detectable label; and,
(b) detecting the presence or absence of said label, wherein detecting the presence of said label indicates the presence of a CD30+ cell in said sample.

33. A method of claim 32, wherein said antibody is selected from the group consisting of an scFv, a dsFv, a Fab, or a F(ab')$_2$.

34. A method of claim 32, further wherein said antibody has a variable heavy chain and a variable light chain, which variable heavy chain and said variable light chain are selected from the group consisting of: a variable heavy chain of SEQ ID NO:14 and a variable light chain of SEQ ID NO:29 (antibody T105), a variable heavy chain of SEQ ID) NO:13 and a variable light chain of SEQ ID NO:28 (antibody T405), and a variable heavy chain of SEQ ID NO:40 and a variable light chain of SEQ ID NO:41 (antibody T408), and, optionally, further wherein a first cysteine residue is substituted for an amino acid residue in a framework region of said variable heavy chain and a second cysteine residue is substituted for an amino acid residue in a framework region of said variable light chain.

35. A method of claim 34, further wherein said antibody is selected from the group consisting of an scFv, a dsFv, a Fab, or a F(ab')$_2$.

36. A method of claim 32, wherein said detection of said presence of said antibody is by an immunoassay.

37. A method of claim 34, wherein said detection of said presence of said antibody is by an immunoassay.

* * * * *

SEQUENCE LISTING

<160> NUMBER OF SEQ ID NOS: 41

<210> SEQ ID NO 1

<400> SEQUENCE: 1

000

<210> SEQ ID NO 2
<211> LENGTH: 118
<212> TYPE: PRT
<213> ORGANISM: Mus musculus
<220> FEATURE:
<223> OTHER INFORMATION: heavy chain variable region (VH) of anti-CD30
      monoclonal antibody (MAb) T6

<400> SEQUENCE: 2

Gln Val Gln Leu Lys Glu Ser Gly Pro Gly Leu Val Thr Pro Ser Gln
 1               5                  10                  15

Ser Leu Ser Ile Thr Cys Thr Val Ser Gly Phe Ser Leu Ser Lys Tyr
            20                  25                  30

Ser Ile His Trp Val Arg Gln Pro Pro Gly Arg Gly Leu Glu Trp Leu
        35                  40                  45

Gly Met Ile Trp Gly Val Glu Asn Thr Asp Tyr Asn Ser Ala Leu Lys
    50                  55                  60

Ser Arg Leu Ser Ile Ser Lys Asp Asn Ser Lys Ser Gln Val Phe Leu
65                  70                  75                  80

Lys Met Asn Ser Leu Gln Ser Asp Asp Thr Ala Met Tyr Tyr Cys Ala
                85                  90                  95

Arg Lys Asp Leu Gly Leu Tyr Gly Met Asn Tyr Trp Gly Gln Gly Ile
            100                 105                 110

Ser Val Thr Val Ser Ala
        115

```
<210> SEQ ID NO 3
<211> LENGTH: 120
<212> TYPE: PRT
<213> ORGANISM: Mus musculus
<220> FEATURE:
<223> OTHER INFORMATION: heavy chain variable region (VH) of anti-CD30
      monoclonal antibody (MAb) T7

<400> SEQUENCE: 3

Gln Val Gln Leu Gln Gln Ser Gly Ala Glu Leu Val Arg Pro Gly Ser
 1               5                  10                  15

Ser Val Lys Ile Ser Cys Lys Ala Ser Gly Tyr Thr Phe Ser Ser Tyr
            20                  25                  30

Trp Met Asn Trp Met Lys Gln Arg Pro Gly Gln Gly Leu Glu Trp Ile
        35                  40                  45

Gly Gln Ile Tyr Pro Gly Asp Asp Thr Asn Tyr Asn Gly Lys Phe
    50                  55                  60

Lys Gly Lys Ala Thr Leu Thr Ala Asp Lys Ser Ser Thr Ala Tyr
65                  70                  75                  80

Met Gln Leu Ser Ser Leu Thr Ser Glu Asp Ser Ala Val Tyr Phe Cys
            85                  90                  95

Ala Arg Arg Glu Thr Gly Arg Gly Ala Trp Phe Thr Tyr Trp Gly Gln
           100                 105                 110

Gly Thr Leu Val Thr Val Ser Ala
           115                 120

<210> SEQ ID NO 4
<211> LENGTH: 120
<212> TYPE: PRT
<213> ORGANISM: Mus musculus
<220> FEATURE:
<223> OTHER INFORMATION: heavy chain variable region (VH) of anti-CD30
      monoclonal antibody (MAb) T13

<400> SEQUENCE: 4

Gln Val Gln Leu Gln Gln Ser Gly Ala Glu Leu Ala Lys Pro Gly Ala
 1               5                  10                  15

Ser Val Lys Met Ser Cys Lys Ala Ser Gly Tyr Thr Phe Thr Thr Tyr
            20                  25                  30

Trp Met His Trp Val Lys Gln Arg Pro Gly Gln Gly Leu Glu Trp Ile
        35                  40                  45

Gly Tyr Ile Asn Pro Ser Thr Gly Tyr Thr Asp Tyr Asn Glu Lys Phe
    50                  55                  60

Lys Asp Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Tyr Cys
            85                  90                  95

Val Arg Arg Gly Ser Tyr Asp Gly Asn Pro Phe Ala Tyr Trp Gly Gln
           100                 105                 110

Gly Thr Leu Val Ser Val Ser Ala
           115                 120

<210> SEQ ID NO 5
<211> LENGTH: 117
<212> TYPE: PRT
<213> ORGANISM: Mus musculus
<220> FEATURE:
<223> OTHER INFORMATION: heavy chain variable region (VH) of anti-CD30
      monoclonal antibody (MAb) T14
```

<400> SEQUENCE: 5

```
Glu Val Gln Leu Val Glu Ser Gly Gly Gly Leu Val Lys Pro Gly Gly
 1               5                  10                  15

Ser Leu Lys Leu Ser Cys Gly Val Ser Gly Phe Thr Phe Ser Asp Tyr
                20                  25                  30

Tyr Met Tyr Trp Val Arg Gln Thr Pro Glu Lys Arg Leu Glu Trp Val
             35                  40                  45

Ala Ser Ile Ser Ser Gly Gly Ser Tyr Thr Tyr Tyr Ser Asp Ser Val
         50                  55                  60

Lys Gly Arg Leu Thr Ile Ser Arg Asp Asn Thr Lys Asn Asn Leu Tyr
 65                  70                  75                  80

Leu Gln Met Ser Ser Leu Lys Ser Glu Asp Thr Ala Val Tyr Tyr Cys
                 85                  90                  95

Val Arg Gly Pro Gly Gly Val Leu Asp Tyr Trp Gly Gln Gly Thr Thr
            100                 105                 110

Leu Thr Val Ser Ser
        115
```

<210> SEQ ID NO 6
<211> LENGTH: 119
<212> TYPE: PRT
<213> ORGANISM: Mus musculus
<220> FEATURE:
<223> OTHER INFORMATION: heavy chain variable region (VH) of anti-CD30
      monoclonal antibody (MAb) T24

<400> SEQUENCE: 6

```
Gln Val Gln Leu Gln Gln Pro Gly Ala Glu Leu Val Arg Pro Gly Ala
 1               5                  10                  15

Ser Val Lys Leu Ser Cys Lys Ala Ser Gly Tyr Ser Phe Thr Ser Tyr
                20                  25                  30

Trp Ile Asp Trp Val Lys Gln Arg Pro Gly Gln Gly Leu Glu Trp Ile
             35                  40                  45

Gly Asn Ile Tyr Pro Ser Asn Ala Tyr Thr Asn Tyr Asn Gln Lys Phe
         50                  55                  60

Lys Asp Lys Ala Thr Leu Thr Val Asp Lys Ser Ser Ser Thr Ala Tyr
 65                  70                  75                  80

Met Gln Leu Ser Ser Pro Thr Ser Glu Asp Ser Ala Val Tyr Tyr Cys
                 85                  90                  95

Thr Ser Val Leu Asp Tyr Phe Tyr Ala Met Asp Tyr Trp Gly Gln Gly
            100                 105                 110

Thr Ser Val Thr Val Ser Ser
        115
```

<210> SEQ ID NO 7
<211> LENGTH: 118
<212> TYPE: PRT
<213> ORGANISM: Mus musculus
<220> FEATURE:
<223> OTHER INFORMATION: heavy chain variable region (VH) of anti-CD30
      monoclonal antibody (MAb) T25

<400> SEQUENCE: 7

```
Gln Val Thr Leu Lys Glu Ser Gly Pro Gly Ile Leu Gln Pro Ser Gln
 1               5                  10                  15

Thr Leu Ser Leu Thr Cys Ser Phe Ser Gly Phe Ser Leu Asn Thr Ser
                20                  25                  30
```

Gly Val Gly Val Gly Trp Ile Arg Gln Pro Ser Gly Lys Gly Leu Glu
            35                  40                  45

Trp Leu Ala His Ile Trp Trp Asp Asp Glu Arg Tyr Asn Pro Val
    50                  55                  60

Leu Lys Ser Arg Leu Thr Ile Ser Lys Asp Thr Ser Asn Gln Val
65                  70                  75                  80

Phe Leu Lys Ile Ala Asn Val Asp Thr Ala Asp Ser Ala Thr Tyr Tyr
                85                  90                  95

Cys Val Arg Ser Met Val Ala Trp Phe Pro Tyr Trp Gly Arg Gly Thr
                100                 105                 110

Leu Val Thr Val Ser Ala
        115

<210> SEQ ID NO 8
<211> LENGTH: 125
<212> TYPE: PRT
<213> ORGANISM: Mus musculus
<220> FEATURE:
<223> OTHER INFORMATION: heavy chain variable region (VH) of anti-CD30
      monoclonal antibody (MAb) control HeFi-I

<400> SEQUENCE: 8

Glu Val Lys Leu Val Glu Ser Gly Gly Gly Leu Val Gln Pro Gly Gly
1               5                   10                  15

Ser Leu Arg Leu Ser Cys Ala Thr Ser Gly Phe Thr Phe Ser Asp Tyr
            20                  25                  30

Tyr Met Asn Trp Val Arg Gln Pro Pro Gly Lys Ala Leu Glu Trp Leu
        35                  40                  45

Gly Phe Ile Arg Asn Lys Ala Asn Gly Tyr Thr Thr Glu Phe Ser Ala
    50                  55                  60

Ser Val Met Gly Arg Phe Thr Ile Ser Arg Asp Asp Ser Gln Ser Ile
65                  70                  75                  80

Leu Tyr Leu Gln Met Asn Thr Leu Arg Ala Glu Asp Ser Ala Thr Tyr
                85                  90                  95

Tyr Cys Ala Arg Asp Pro Pro Tyr Gly Asn Pro His Tyr Tyr Ala Met
                100                 105                 110

Asp Tyr Trp Gly Gln Gly Thr Ser Val Thr Val Ser Ser
        115                 120                 125

<210> SEQ ID NO 9
<211> LENGTH: 121
<212> TYPE: PRT
<213> ORGANISM: Mus musculus
<220> FEATURE:
<223> OTHER INFORMATION: heavy chain variable region (VH) of anti-CD30
      monoclonal antibody (MAb) CL2

<400> SEQUENCE: 9

Glu Val Gln Leu Lys Gln Ser Gly Thr Glu Leu Val Lys Pro Gly Ala
1               5                   10                  15

Ser Val Lys Leu Ser Cys Lys Ala Ser Gly Tyr Thr Phe Thr Ser Tyr
            20                  25                  30

Trp Met His Trp Val Lys Gln Arg Pro Gly Gln Gly Leu Glu Trp Ile
        35                  40                  45

Gly Asn Ile Asn Pro Ser Asn Gly Gly Thr Asn Tyr Asn Glu Lys Phe
    50                  55                  60

Lys Ser Lys Ala Thr Leu Thr Ile Asp Lys Ser Ser Ser Thr Ala Tyr
65                  70                  75                  80

```
Met Gln Leu Ser Ser Leu Thr Ser Glu Asp Ser Ala Val Tyr Tyr Cys
            85                  90                  95

Ala Arg Arg Thr Glu Thr Ala Gln Ala Ser Pro Phe Ala Tyr Trp Gly
            100                 105                 110

Gln Gly Thr Leu Val Thr Val Ser Ser
            115                 120

<210> SEQ ID NO 10
<211> LENGTH: 120
<212> TYPE: PRT
<213> ORGANISM: Mus musculus
<220> FEATURE:
<223> OTHER INFORMATION: heavy chain variable region (VH) of anti-CD30
      monoclonal antibody (MAb) Ki-4

<400> SEQUENCE: 10

Gln Val Lys Leu Gln Glu Ser Gly Thr Glu Leu Ala Lys Pro Gly Ala
1               5                   10                  15

Ala Val Lys Met Ser Cys Lys Ala Ser Gly Tyr Thr Phe Thr Asp Tyr
            20                  25                  30

Trp Met His Trp Val Lys Gln Arg Pro Gly Gln Gly Leu Glu Trp Ile
            35                  40                  45

Gly Tyr Ile Asn Pro Asn Thr Ala Tyr Thr Asp Tyr Asn Gln Lys Phe
        50                  55                  60

Lys Asp Lys Ala Thr Leu Thr Ala Asp Lys Ser Ser Ser Thr Ala Tyr
65                  70                  75                  80

Met Gln Leu Arg Ser Leu Thr Ser Glu Asp Ser Ala Val Tyr Tyr Cys
            85                  90                  95

Ala Lys Lys Thr Thr Gln Thr Thr Trp Gly Phe Pro Phe Trp Gly Gln
            100                 105                 110

Gly Thr Leu Val Thr Val Ser Ser
            115                 120

<210> SEQ ID NO 11
<211> LENGTH: 120
<212> TYPE: PRT
<213> ORGANISM: Mus musculus
<220> FEATURE:
<223> OTHER INFORMATION: heavy chain variable region (VH) of anti-CD30
      monoclonal antibody (MAb) T420

<400> SEQUENCE: 11

Gln Val Gln Leu Gln Gln Ser Gly Ala Glu Leu Ala Lys Pro Gly Ala
1               5                   10                  15

Ser Val Lys Met Ser Cys Lys Ala Ser Gly Tyr Thr Phe Thr Ser Tyr
            20                  25                  30

Trp Met His Trp Val Lys Gln Arg Pro Gly Gln Asp Leu Glu Trp Ile
            35                  40                  45

Gly Tyr Ile Asn Pro Ser Thr Asp Tyr Thr Asp Tyr Asn Gln Lys Phe
        50                  55                  60

Lys Asp Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Tyr Cys
            85                  90                  95

Ala Thr Arg His Tyr Gly Ser Ser Tyr Gly Phe Ala Tyr Trp Gly Gln
            100                 105                 110

Gly Thr Leu Val Thr Val Ser Ala
            115                 120
```

```
<210> SEQ ID NO 12
<211> LENGTH: 119
<212> TYPE: PRT
<213> ORGANISM: Mus musculus
<220> FEATURE:
<223> OTHER INFORMATION: heavy chain variable region (VH) of anti-CD30
      monoclonal antibody (MAb) T427

<400> SEQUENCE: 12

Gln Val Gln Leu Gln Gln Pro Gly Thr Glu Leu Val Arg Pro Gly Ala
  1               5                  10                  15

Ser Val Lys Leu Ser Cys Lys Ala Ser Gly Phe Ser Phe Thr Ser Tyr
             20                  25                  30

Trp Met Asn Trp Val Lys Gln Arg Pro Gly Gln Gly Leu Glu Trp Ile
         35                  40                  45

Gly Met Ile His Pro Ser Asp Ser Glu Thr Arg Leu Asn Gln Lys Phe
     50                  55                  60

Lys Asp Arg Ala Thr Leu Thr Val Asp Lys Ser Ser Thr Ala Tyr
 65                  70                  75                  80

Met Gln Leu Ser Ser Pro Thr Ser Glu Asp Ser Ala Val Tyr Tyr Cys
                 85                  90                  95

Ala Ser Glu Met Asp Tyr Tyr Phe Ala Met Asp Tyr Trp Gly Gln Gly
            100                 105                 110

Thr Ser Val Thr Val Ser Ser
        115

<210> SEQ ID NO 13
<211> LENGTH: 112
<212> TYPE: PRT
<213> ORGANISM: Mus musculus
<220> FEATURE:
<223> OTHER INFORMATION: heavy chain variable region (VH) of anti-CD30
      monoclonal antibody (MAb) T405

<400> SEQUENCE: 13

Gln Val Gln Leu Gln Gln Ile Gly Ala Glu Leu Val Arg Pro Gly Ala
  1               5                  10                  15

Ser Val Lys Leu Ser Cys Lys Ala Ser Gly Tyr Thr Phe Asn Asn Tyr
             20                  25                  30

Trp Ile Asn Trp Val Lys Gln Arg Pro Gly Gln Gly Leu Glu Trp Ile
         35                  40                  45

Gly Asn Ile Tyr Pro Ser Asp Ser Arg Ser Asn Tyr Asn Gln Lys Phe
     50                  55                  60

Lys Asp Lys Ala Thr Leu Thr Val Asp Lys Pro Ser Ser Thr Ala Tyr
 65                  70                  75                  80

Met Gln Leu Ser Ser Pro Thr Ser Glu Asp Ser Ala Val Tyr Tyr Cys
                 85                  90                  95

Thr Leu Gly Ser Tyr Trp Gly Gln Gly Thr Leu Val Thr Val Ser Ala
            100                 105                 110

<210> SEQ ID NO 14
<211> LENGTH: 121
<212> TYPE: PRT
<213> ORGANISM: Mus musculus
<220> FEATURE:
<223> OTHER INFORMATION: heavy chain variable region (VH) of anti-CD30
      monoclonal antibody (MAb) T105

<400> SEQUENCE: 14

Gln Val Thr Leu Lys Glu Ser Gly Pro Gly Ile Leu Gln Pro Ser Gln
```

-continued

```
                1               5              10              15
Thr Leu Ser Leu Thr Cys Ser Phe Ser Gly Phe Ser Leu Ser Thr Ser
                       20              25              30

Gly Met Gly Val Ser Trp Ile Arg Gln Pro Ser Gly Lys Asp Leu Glu
               35              40              45

Trp Leu Ala His Ile Tyr Trp Asp Asp Lys Arg Tyr Asn Pro Ser
        50              55              60

Leu Lys Ser Arg Leu Thr Ile Ser Lys Asp Thr Ser Ser Asn Gln Val
 65              70              75              80

Phe Leu Lys Ile Thr Ser Val Asp Thr Ala Asp Thr Ala Thr Tyr Tyr
                    85              90              95

Cys Ala Arg Arg Ala Asp Gly Leu Tyr Phe Tyr Leu Asp Val Trp Gly
                100             105             110

Ala Gly Thr Thr Val Thr Val Ser Ser
            115             120
```

<210> SEQ ID NO 15
<211> LENGTH: 109
<212> TYPE: PRT
<213> ORGANISM: Mus musculus
<220> FEATURE:
<223> OTHER INFORMATION: light chain variable region (VL) of anti-CD30
      monoclonal antibody (MAb) T6

<400> SEQUENCE: 15

```
Asp Ile Val Met Thr Gln Ser Gln Lys Phe Met Ser Thr Ser Val Gly
 1               5              10              15

Asp Arg Val Ser Val Thr Cys Lys Ala Ser Gln Asn Val Gly Thr Asn
                20              25              30

Val Ala Trp Tyr Gln Gln Lys Pro Gly Gln Ser Pro Lys Ala Leu Phe
                35              40              45

Tyr Ser Ala Ser Tyr Arg Tyr Ser Gly Val Pro Asp Arg Phe Ile Gly
        50              55              60

Ser Gly Ser Gly Thr Val Phe Thr Leu Thr Ile Ser Asn Val Gln Ser
 65              70              75              80

Glu Asp Leu Ala Glu Tyr Phe Cys Gln Gln Tyr Asn Thr Tyr Pro Leu
                    85              90              95

Thr Phe Gly Ser Gly Thr Lys Leu Glu Ile Glu Arg Ala
                100             105
```

<210> SEQ ID NO 16
<211> LENGTH: 114
<212> TYPE: PRT
<213> ORGANISM: Mus musculus
<220> FEATURE:
<223> OTHER INFORMATION: light chain variable region (VL) of anti-CD30
      monoclonal antibody (MAb) T7

<400> SEQUENCE: 16

```
Asp Ile Val Leu Thr Gln Ser Pro Ala Ser Leu Ala Val Ser Leu Gly
 1               5              10              15

Gln Arg Ala Thr Ile Ser Cys Arg Ala Ser Glu Ser Leu Glu Tyr Tyr
                20              25              30

Gly Thr Thr Leu Met Gln Trp Tyr Gln Gln Lys Pro Gly Gln Pro Pro
                35              40              45

Lys Leu Leu Ile Tyr Ala Ala Ser Asn Val Glu Ser Gly Val Pro Ala
        50              55              60

Arg Phe Ser Gly Ser Gly Ser Gly Thr Asp Phe Ser Leu Asn Ile His
```

```
              65                  70                  75                  80
Pro Val Glu Glu Asp Asp Ile Ala Met Tyr Phe Cys His Gln Ser Arg
                    85                  90                  95
Lys Val Pro Ser Thr Phe Gly Gly Thr Lys Leu Glu Ile Lys Arg
                100                 105                 110
Ala Asp

<210> SEQ ID NO 17
<211> LENGTH: 109
<212> TYPE: PRT
<213> ORGANISM: Mus musculus
<220> FEATURE:
<223> OTHER INFORMATION: light chain variable region (VL) of anti-CD30
      monoclonal antibody (MAb) T13

<400> SEQUENCE: 17

Asp Ile Val Met Thr Gln Ser His Lys Phe Met Ser Thr Ser Val Gly
 1               5                  10                  15
Asp Arg Val Thr Ile Thr Cys Lys Ala Ser Gln Asp Val Ser Thr Ala
                20                  25                  30
Val Ala Trp Tyr Gln Gln Lys Pro Gly His Ser Pro Lys Leu Leu Ile
            35                  40                  45
Tyr Trp Ala Ser Thr Arg His Thr Gly Val Pro Asp Arg Phe Thr Gly
        50                  55                  60
Ser Gly Ser Gly Thr Asp Tyr Thr Leu Thr Ile Ser Ser Val Gln Val
 65                 70                  75                  80
Glu Asp Leu Ala Leu Tyr Tyr Cys Gln Gln His Tyr Ser Thr Pro Phe
                85                  90                  95
Thr Phe Gly Ser Gly Thr Lys Leu Glu Ile Lys Arg Ala
                100                 105

<210> SEQ ID NO 18
<211> LENGTH: 115
<212> TYPE: PRT
<213> ORGANISM: Mus musculus
<220> FEATURE:
<223> OTHER INFORMATION: light chain variable region (VL) of anti-CD30
      monoclonal antibody (MAb) T14-A

<400> SEQUENCE: 18

Asp Val Val Met Thr Gln Thr Pro Leu Ser Leu Pro Val Ser Leu Gly
 1               5                  10                  15
Asp Gln Ala Ser Ile Ser Cys Arg Ser Ser Gln Asn Leu Ile His Ser
                20                  25                  30
Asn Gly Asn Ala Tyr Leu Gln Trp Tyr Leu Gln Lys Pro Gly Gln Ser
            35                  40                  45
Pro Lys Leu Leu Ile Tyr Lys Val Ser Asn Arg Phe Ser Gly Val Pro
        50                  55                  60
Asp Arg Phe Ser Gly Ser Gly Ser Gly Thr Asp Phe Ala Leu Lys Ile
 65                 70                  75                  80
Ile Arg Val Glu Ala Glu Asp Leu Gly Val Tyr Phe Cys Ser Gln Thr
                85                  90                  95
Thr His Val Pro Tyr Thr Phe Gly Gly Gly Thr Lys Leu Glu Ile Lys
                100                 105                 110
Arg Ala Asp
        115

<210> SEQ ID NO 19
```

<211> LENGTH: 114
<212> TYPE: PRT
<213> ORGANISM: Mus musculus
<220> FEATURE:
<223> OTHER INFORMATION: light chain variable region (VL) of anti-CD30
monoclonal antibody (MAb) T14-B

<400> SEQUENCE: 19

Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Leu Glu Tyr Tyr
            20                  25                  30

Gly Thr Thr Leu Met Gln Trp Tyr Gln Gln Lys Pro Gly Gln Pro Pro
        35                  40                  45

Lys Leu Leu Ile Tyr Ala Ala Ser Asn Val Glu Ser Gly Val Pro Ala
    50                  55                  60

Arg Phe Ser Gly Ser Gly Ser Gly Thr Asp Phe Ser Leu Asn Ile His
65                  70                  75                  80

Pro Val Glu Glu Asp Asp Ile Ala Met Tyr Phe Cys His Gln Ser Arg
                85                  90                  95

Lys Val Pro Ser Thr Phe Gly Gly Gly Thr Lys Leu Glu Ile Lys Arg
            100                 105                 110

Ala Asp

<210> SEQ ID NO 20
<211> LENGTH: 109
<212> TYPE: PRT
<213> ORGANISM: Mus musculus
<220> FEATURE:
<223> OTHER INFORMATION: light chain variable region (VL) of anti-CD30
monoclonal antibody (MAb) T21

<400> SEQUENCE: 20

Asp Ile Gln Met Asn Gln Ser Pro Ser Ser Leu Ser Ala Ser Leu Gly
1               5                   10                  15

Asp Thr Ile Thr Ile Thr Cys His Ala Ser Gln Asn Ile Asn Val Trp
            20                  25                  30

Leu Thr Trp Tyr Gln Gln Lys Pro Gly Asn Ile Pro Gln Leu Leu Ile
        35                  40                  45

Tyr Lys Ala Ser Asn Leu His Thr Gly Val Pro Ser Arg Phe Ser Gly
    50                  55                  60

Ser Gly Ser Gly Thr Gly Phe Thr Leu Thr Ile Ser Ser Leu Gln Pro
65                  70                  75                  80

Glu Asp Ile Ala Thr Tyr Tyr Cys Gln Gln Gly Gln Ser Tyr Pro Leu
                85                  90                  95

Thr Phe Gly Ala Gly Thr Lys Leu Glu Leu Lys Arg Ala
            100                 105

<210> SEQ ID NO 21
<211> LENGTH: 109
<212> TYPE: PRT
<213> ORGANISM: Mus musculus
<220> FEATURE:
<223> OTHER INFORMATION: light chain variable region (VL) of anti-CD30
monoclonal antibody (MAb) T24

<400> SEQUENCE: 21

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Asn Tyr

```
                         20                  25                  30

Leu Asn Trp Tyr Gln Gln Lys Pro Asp Gly Thr Val Lys Leu Leu Ile
                 35                  40                  45

Tyr Tyr Thr Ser Arg Leu His Ser Gly Val Pro Ser Arg Phe Ser Gly
         50                  55                  60

Ser Gly Ser Gly Thr Asp Tyr Ser Leu Thr Ile Ser Asn Leu Glu Gln
 65                  70                  75                  80

Glu Asp Ile Ala Thr Tyr Phe Cys Gln Gln Val Asn Thr Leu Pro Arg
                 85                  90                  95

Thr Phe Gly Gly Gly Thr Lys Leu Glu Ile Lys Arg Ala
                100                 105

<210> SEQ ID NO 22
<211> LENGTH: 116
<212> TYPE: PRT
<213> ORGANISM: Mus musculus
<220> FEATURE:
<223> OTHER INFORMATION: light chain variable region (VL) of anti-CD30
      monoclonal antibody (MAb) T25

<400> SEQUENCE: 22

Asp Ile Val Met Ser Gln Ser Pro Ser Ser Leu Ala Val Ser Val Gly
 1               5                  10                  15

Glu Lys Phe Thr Val Asn Cys Lys Ser Ser Gln Ser Leu Leu Tyr Ser
                 20                  25                  30

Ser Asn Gln Lys Asn Phe Leu Ala Trp Tyr Gln Gln Lys Pro Gly Gln
         35                  40                  45

Ser Pro Lys Leu Leu Ile Tyr Trp Ala Ser Thr Arg Glu Ser Gly Val
     50                  55                  60

Pro Asp Arg Phe Ile Gly Ser Gly Ser Gly Thr Asp Phe Thr Leu Thr
 65                  70                  75                  80

Ile Ser Ser Val Lys Ala Glu Asp Leu Ala Val Tyr Tyr Cys Gln Gln
                 85                  90                  95

His Tyr Arg Tyr Pro Trp Thr Phe Gly Gly Gly Thr Lys Leu Glu Ile
                100                 105                 110

Lys Arg Ala Arg
        115

<210> SEQ ID NO 23
<211> LENGTH: 113
<212> TYPE: PRT
<213> ORGANISM: Mus musculus
<220> FEATURE:
<223> OTHER INFORMATION: light chain variable region (VL) of anti-CD30
      monoclonal antibody (MAb) control HeFi-I

<400> SEQUENCE: 23

Asp Ile Val Leu Thr Gln Ser Pro Ala Ser Leu Ala Val Ser Leu Gly
 1               5                  10                  15

Gln Arg Ala Thr Ile Ser Cys Arg Ala Ser Lys Ser Val Ser Ala Ser
                 20                  25                  30

Gly Tyr Asn Tyr Met His Trp Tyr Gln Gln Lys Ala Gly Gln Pro Pro
         35                  40                  45

Lys Leu Leu Ile His Leu Ala Ser Asn Leu Glu Ser Gly Val Pro Ala
     50                  55                  60

Arg Phe Ser Gly Ser Gly Ser Gly Thr Asp Phe Thr Leu Asn Ile His
 65                  70                  75                  80

Pro Val Glu Glu Glu Asp Ala Ser Thr Tyr Tyr Cys Gln His Ser Gly
```

-continued

```
                     85                  90                  95
Glu Leu Pro Phe Thr Phe Gly Ser Gly Thr Lys Leu Glu Ile Lys Arg
                100                 105                 110
Ala

<210> SEQ ID NO 24
<211> LENGTH: 107
<212> TYPE: PRT
<213> ORGANISM: Mus musculus
<220> FEATURE:
<223> OTHER INFORMATION: light chain variable region (VL) of anti-CD30
      monoclonal antibody (MAb) CL2

<400> SEQUENCE: 24

Asp Ile Val Met Thr Gln Ser His Lys Phe Met Ser Thr Ser Val Gly
  1               5                  10                  15

Asp Arg Val Ser Val Thr Cys Lys Ala Ser Gln Asn Val Gly Thr Asn
             20                  25                  30

Val Ala Trp Tyr Gln Gln Lys Pro Gly Gln Ser Pro Lys Ala Leu Ile
         35                  40                  45

Tyr Ser Ala Ser Thr Arg Tyr Ser Gly Val Pro Asp Arg Phe Thr Gly
     50                  55                  60

Ser Gly Ser Gly Thr Asp Phe Thr Leu Thr Ile Ser Asn Val Gln Ser
 65                  70                  75                  80

Glu Asp Leu Ala Glu Tyr Phe Cys Gln Gln Tyr Asn Ser Tyr Pro Phe
                 85                  90                  95

Thr Phe Gly Ser Gly Thr Lys Leu Glu Ile Lys
                100                 105

<210> SEQ ID NO 25
<211> LENGTH: 107
<212> TYPE: PRT
<213> ORGANISM: Mus musculus
<220> FEATURE:
<223> OTHER INFORMATION: light chain variable region (VL) of anti-CD30
      monoclonal antibody (MAb) Ki-4

<400> SEQUENCE: 25

Asp Ile Val Leu Thr Gln Ser His Lys Ser Met Ala Met Ser Val Gly
  1               5                  10                  15

Glu Arg Val Thr Leu Ser Cys Lys Ala Ser Glu Asn Val Asp Ser Phe
             20                  25                  30

Val Ser Trp Tyr Gln Gln Lys Pro Gly Gln Ser Pro Lys Ala Leu Ile
         35                  40                  45

Tyr Gly Ala Ser Asn Arg His Ser Gly Val Pro Asp Arg Phe Ala Gly
     50                  55                  60

Ser Gly Ser Gly Arg Asp Phe Thr Leu Thr Ile Ser Ser Val Gln Ala
 65                  70                  75                  80

Glu Asp Leu Ala Asp Tyr His Cys Gln Gln Asn Tyr Arg Tyr Pro Leu
                 85                  90                  95

Thr Phe Gly Ala Gly Thr Lys Leu Glu Ile Lys
                100                 105

<210> SEQ ID NO 26
<211> LENGTH: 108
<212> TYPE: PRT
<213> ORGANISM: Mus musculus
<220> FEATURE:
<223> OTHER INFORMATION: light chain variable region (VL) of anti-CD30
      monoclonal antibody (MAb) T420
```

```
<400> SEQUENCE: 26

Asp Ile Val Met Thr Gln Ser His Lys Phe Met Ser Thr Ser Val Gly
 1               5                  10                  15

Asp Arg Val Ser Ile Thr Cys Lys Ala Ser Gln Asp Val Ser Thr Ala
             20                  25                  30

Val Ala Trp Tyr Gln Gln Lys Pro Gly Gln Ser Pro Lys Leu Leu Ile
         35                  40                  45

Tyr Trp Ala Ser Thr Arg His Thr Gly Val Pro Asp Arg Phe Thr Gly
     50                  55                  60

Ser Gly Ser Gly Thr Asp Tyr Ser Leu Thr Ile Ser Ser Val Gln Ala
 65                  70                  75                  80

Glu Asp Leu Ala Val Tyr Tyr Cys Gln Gln His Tyr Arg Thr Pro Phe
                 85                  90                  95

Thr Phe Gly Ser Gly Thr Lys Leu Glu Ile Lys Arg
            100                 105

<210> SEQ ID NO 27
<211> LENGTH: 112
<212> TYPE: PRT
<213> ORGANISM: Mus musculus
<220> FEATURE:
<223> OTHER INFORMATION: light chain variable region (VL) of anti-CD30
      monoclonal antibody (MAb) T427

<400> SEQUENCE: 27

Asp Ile Val Leu Thr Gln Ser Pro Thr Ser Leu Ala Val Ser Leu Gly
 1               5                  10                  15

Gln Arg Ala Thr Ile Ser Cys Arg Ala Ser Glu Ser Val Asp Ser Tyr
             20                  25                  30

Gly Asn Ser Phe Met His Trp Phe Gln Gln Lys Pro Gly Gln Pro Pro
         35                  40                  45

Lys Leu Leu Ile Tyr Arg Ala Ser Asn Leu Glu Ser Gly Ile Pro Ala
     50                  55                  60

Arg Phe Ser Gly Ser Gly Ser Trp Thr Asp Phe Thr Leu Thr Ile Asn
 65                  70                  75                  80

Pro Val Glu Ala Asp Asp Val Ala Thr Tyr Tyr Cys Gln Gln Ser Asn
                 85                  90                  95

Glu Asp Pro Arg Thr Phe Gly Gly Gly Thr Lys Leu Glu Ile Lys Arg
            100                 105                 110

<210> SEQ ID NO 28
<211> LENGTH: 113
<212> TYPE: PRT
<213> ORGANISM: Mus musculus
<220> FEATURE:
<223> OTHER INFORMATION: light chain variable region (VL) of anti-CD30
      monoclonal antibody (MAb) T405

<400> SEQUENCE: 28

Asp Val Val Met Thr Gln Thr Pro Leu Thr Leu Ser Val Thr Ile Gly
 1               5                  10                  15

Gln Pro Ala Ser Ile Ser Cys Lys Ser Ser Gln Ser Leu Ser Asp Ser
             20                  25                  30

Asp Gly Lys Thr Tyr Leu Asn Trp Leu Leu Gln Arg Pro Gly Gln Ser
         35                  40                  45

Pro Lys Arg Leu Ile Tyr Leu Val Ser Lys Leu Asp Ser Gly Val Pro
     50                  55                  60
```

```
Asp Arg Phe Thr Gly Ser Gly Ser Gly Thr Asp Phe Thr Leu Lys Ile
 65                  70                  75                  80

Ser Arg Val Glu Ala Glu Asp Leu Gly Val Tyr Tyr Cys Trp Gln Gly
             85                  90                  95

Ala His Phe Pro Arg Thr Phe Gly Gly Gly Thr Lys Leu Glu Ile Lys
            100                 105                 110

Arg

<210> SEQ ID NO 29
<211> LENGTH: 108
<212> TYPE: PRT
<213> ORGANISM: Mus musculus
<220> FEATURE:
<223> OTHER INFORMATION: light chain variable region (VL) of anti-CD30
      monoclonal antibody (MAb) T105

<400> SEQUENCE: 29

Asp Ile Val Met Thr Gln Ser Gln Lys Phe Met Ser Thr Ser Val Gly
  1               5                  10                  15

Asp Arg Val Ser Val Thr Cys Lys Ala Ser Gln Asn Val Asn Thr Asn
             20                  25                  30

Val Ala Trp Tyr Gln Gln Lys Pro Gly Gln Ser Pro Glu Ala Leu Ile
         35                  40                  45

Tyr Ser Ala Ser Tyr Arg Tyr Ser Gly Val Pro Asp Arg Phe Thr Gly
 50                  55                  60

Ser Gly Ser Gly Thr Asp Phe Thr Leu Thr Ile Ser Asn Val Gln Ser
 65                  70                  75                  80

Glu Asp Leu Ala Glu Tyr Phe Cys Gln Gln Tyr Asn Ser Tyr Pro Leu
             85                  90                  95

Thr Phe Gly Ser Gly Thr Lys Leu Glu Ile Lys Arg
            100                 105

<210> SEQ ID NO 30
<211> LENGTH: 4
<212> TYPE: PRT
<213> ORGANISM: Artificial Sequence
<220> FEATURE:
<223> OTHER INFORMATION: Description of Artificial Sequence:Pseudomonas
      exotoxin (PE) carboxyl terminus addition

<400> SEQUENCE: 30

Lys Asp Glu Leu
  1

<210> SEQ ID NO 31
<211> LENGTH: 4
<212> TYPE: PRT
<213> ORGANISM: Artificial Sequence
<220> FEATURE:
<223> OTHER INFORMATION: Description of Artificial Sequence:Pseudomonas
      exotoxin (PE) carboxyl terminus addition

<400> SEQUENCE: 31

Arg Glu Asp Leu
  1

<210> SEQ ID NO 32
<211> LENGTH: 24
<212> TYPE: DNA
<213> ORGANISM: Artificial Sequence
<220> FEATURE:
<223> OTHER INFORMATION: Description of Artificial Sequence:kappa Ig
      subclass-specific 3' end primer
```

<400> SEQUENCE: 32
gactgaggca cctccagatg ttaa                                            24

<210> SEQ ID NO 33
<211> LENGTH: 24
<212> TYPE: DNA
<213> ORGANISM: Artificial Sequence
<220> FEATURE:
<223> OTHER INFORMATION: Description of Artificial Sequence:gamma1 Ig
      subclass-specific 3' end primer

<400> SEQUENCE: 33
cagggtcacc atggagttag tttg                                            24

<210> SEQ ID NO 34
<211> LENGTH: 24
<212> TYPE: DNA
<213> ORGANISM: Artificial Sequence
<220> FEATURE:
<223> OTHER INFORMATION: Description of Artificial Sequence:gamma2b Ig
      subclass-specific 3' end primer

<400> SEQUENCE: 34
tccagagttc caagtcacag tcac                                            24

<210> SEQ ID NO 35
<211> LENGTH: 33
<212> TYPE: DNA
<213> ORGANISM: Artificial Sequence
<220> FEATURE:
<223> OTHER INFORMATION: Description of Artificial Sequence:kappa 5'
      end primer

<400> SEQUENCE: 35
ggatggtggg aagatggata cagttggtgc agc                                  33

<210> SEQ ID NO 36
<211> LENGTH: 30
<212> TYPE: DNA
<213> ORGANISM: Artificial Sequence
<220> FEATURE:
<223> OTHER INFORMATION: Description of Artificial Sequence:gamma1 5'
      end primer

<400> SEQUENCE: 36
aggggccagt ggatagacag atgggggtgt                                      30

<210> SEQ ID NO 37
<211> LENGTH: 30
<212> TYPE: DNA
<213> ORGANISM: Artificial Sequence
<220> FEATURE:
<223> OTHER INFORMATION: Description of Artificial Sequence:gamma2b 5'
      end primer

<400> SEQUENCE: 37
aggggccagt ggatagactg atgggggtgt                                      30

<210> SEQ ID NO 38
<211> LENGTH: 117
<212> TYPE: PRT
<213> ORGANISM: Mus musculus
<220> FEATURE:
<223> OTHER INFORMATION: heavy chain variable region (VH) of anti-CD30
      monoclonal antibody (MAb) T201

-continued

```
<400> SEQUENCE: 38

Gln Val Gln Leu Lys Glu Ser Gly Pro Gly Leu Val Ala Pro Ser Gln
  1               5                  10                  15

Ser Leu Ser Ile Thr Cys Thr Val Ser Gly Phe Ser Leu Ile Asp Tyr
             20                  25                  30

Gly Val Ser Trp Val Arg Gln Pro Pro Gly Lys Gly Leu Glu Trp Leu
         35                  40                  45

Gly Met Ile Trp Gly Asp Gly Asn Thr Asp Tyr Asn Ser Gly Leu Lys
     50                  55                  60

Ser Arg Leu Ser Ile Ser Lys Asp Asn Ser Lys Ser Gln Val Phe Leu
 65                  70                  75                  80

Lys Val Asn Ser Leu Gln Thr Asp Asp Thr Ala Arg Tyr Tyr Cys Ala
                 85                  90                  95

Arg Pro Ser Thr Gly Thr Leu Phe Ala Tyr Trp Gly Gln Gly Thr Leu
            100                 105                 110

Val Thr Val Ser Ala
        115

<210> SEQ ID NO 39
<211> LENGTH: 110
<212> TYPE: PRT
<213> ORGANISM: Mus musculus
<220> FEATURE:
<223> OTHER INFORMATION: light chain variable region (VL) of anti-CD30
      monoclonal antibody (MAb) T201

<400> SEQUENCE: 39

Glu Ile Val Leu Thr Gln Ser Pro Thr Thr Met Ala Ala Ser Pro Gly
  1               5                  10                  15

Glu Arg Ile Thr Phe Thr Cys Ser Ala Ser Ser Gly Ile Ser Ser Ile
             20                  25                  30

Tyr Leu His Trp Tyr Gln Gln Lys Pro Gly Phe Ser Pro Lys Leu Leu
         35                  40                  45

Ile Tyr Arg Thr Ser Asn Leu Ala Ser Gly Val Pro Pro Arg Phe Ser
     50                  55                  60

Gly Ser Gly Ser Gly Thr Ser Tyr Ser Leu Thr Ile Gly Thr Met Glu
 65                  70                  75                  80

Ala Glu Asp Val Ala Thr Tyr Tyr Cys Gln Gln Gly Ser Ser Ile Pro
                 85                  90                  95

Leu Thr Phe Gly Ala Gly Thr Lys Leu Glu Leu Lys Arg Ala
            100                 105                 110

<210> SEQ ID NO 40
<211> LENGTH: 112
<212> TYPE: PRT
<213> ORGANISM: Mus musculus
<220> FEATURE:
<223> OTHER INFORMATION: heavy chain variable region (VL) of anti-CD30
      monoclonal antibody (MAb) T408

<400> SEQUENCE: 40

Gln Val Gln Leu Gln Gln Pro Gly Ala Glu Leu Val Arg Pro Gly Ala
  1               5                  10                  15

Ser Val Lys Leu Ser Cys Lys Ala Ser Gly Tyr Thr Phe Thr Ser Tyr
             20                  25                  30

Trp Ile Asn Trp Val Lys Gln Arg Pro Gly Gln Gly Leu Glu Trp Ile
         35                  40                  45

Gly Asn Ile Tyr Pro Ser Asp Ser Tyr Ser Asn Tyr Asn Gln Lys Phe
```

-continued

```
                    50                     55                     60
Lys Asp Lys Ala Thr Leu Thr Val Asp Lys Ser Ser Thr Ala Tyr
 65                     70                     75                     80

Met Gln Leu Ser Ser Pro Thr Ser Glu Asp Ser Ala Val Tyr Tyr Cys
                    85                     90                     95

Thr Leu Gly Ser Tyr Trp Gly Gln Gly Thr Leu Val Thr Val Ser Ala
                   100                    105                    110

<210> SEQ ID NO 41
<211> LENGTH: 114
<212> TYPE: PRT
<213> ORGANISM: Mus musculus
<220> FEATURE:
<223> OTHER INFORMATION: light chain variable region (VL) of anti-CD30
      monoclonal antibody (MAb) T408

<400> SEQUENCE: 41

Asp Val Val Met Thr Gln Thr Pro Leu Thr Leu Ser Val Thr Ile Gly
  1               5                  10                  15

Gln Pro Ala Ser Ile Ser Cys Lys Ser Ser Gln Ser Leu Ser Asp Ser
             20                  25                  30

Asp Gly Lys Thr Tyr Leu Asn Trp Leu Leu Gln Arg Pro Gly Gln Ser
         35                  40                  45

Pro Lys Arg Leu Ile Tyr Leu Val Ser Lys Leu Asp Ser Gly Val Pro
     50                  55                  60

Asp Arg Phe Thr Gly Ser Gly Ser Gly Thr Asp Phe Thr Leu Lys Ile
 65                  70                  75                  80

Ser Arg Val Glu Ala Glu Asp Leu Gly Val Tyr Tyr Cys Trp Gln Gly
                 85                  90                  95

Ala His Phe Pro Arg Thr Phe Gly Gly Gly Thr Lys Leu Glu Ile Lys
            100                 105                 110

Arg Ala
```